(12) United States Patent
Carroll et al.

(10) Patent No.: US 8,981,102 B2
(45) Date of Patent: Mar. 17, 2015

(54) NICOTINIC RECEPTOR COMPOUNDS

(75) Inventors: Frank Ivy Carroll, Durham, NC (US); Pauline Wanjiku Ondachi, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 13/817,697

(22) PCT Filed: Aug. 19, 2011

(86) PCT No.: PCT/US2011/048470
§ 371 (c)(1),
(2), (4) Date: Feb. 19, 2013

(87) PCT Pub. No.: WO2012/024615
PCT Pub. Date: Feb. 23, 2012

(65) Prior Publication Data
US 2013/0150373 A1    Jun. 13, 2013

Related U.S. Application Data

(60) Provisional application No. 61/375,630, filed on Aug. 20, 2010.

(51) Int. Cl.
| | | |
|---|---|---|
| *C07D 401/00* | (2006.01) | |
| *C07D 409/14* | (2006.01) | |
| *C07D 487/08* | (2006.01) | |
| *A61K 31/407* | (2006.01) | |
| *C07D 401/14* | (2006.01) | |

(52) U.S. Cl.
CPC ............ *C07D 409/14* (2013.01); *C07D 487/08* (2013.01); *A61K 31/407* (2013.01); *C07D 401/14* (2013.01)
USPC ........................................................ 546/125

(58) Field of Classification Search
CPC .................................................. C07D 487/08
USPC ........................................................ 546/125
See application file for complete search history.

(56) References Cited

U.S. PATENT DOCUMENTS 6,538,010 B1 * 3/2003 Carroll ........................ 514/339

OTHER PUBLICATIONS

Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
Gao et al. Journal of Medicinal Chemistry, 2007, 50, 3814-3824.*
Gao et al. Journal of Medicinal Chemistry, 2008, 51, 4751-4764.*
Abdrakhmanova, et al. "2-Flouro-3-(4-nitro-phenyl) deschloreopibatidine is a Novel Potent Competitive Antagonist of Human Neuronal α4β2 nAChRs", *Molecular Pharmacology*, 2006, pp. 1945-1952, vol. 69, No. 6.
Billingsley et al., "Palladium-Catalyzed Borylation of Aryl Chlorides: Scope, Applications, and Computational Studies", *Angew. Chem. Int. Ed.*, 2007, pp. 5359-5363, vol. 46.
Brieaddy et al., "New Synthesis of 7-(*tert*-Butoxycabonly)-7-azabicyclo[2.2.1]hept-2-ene. A Key Intermediate in the Synthesis of Epibatidine and Analogs", *Tetrahedron Letters*, 1998, pp. 5321-5322, vol. 39.
Carroll et al., "Synthesis, Nicotinic Acetylcholine Receptor Binding, and Antinociceptive Properties of 2-*exo*-(2'-Substituted 5'-pyridinyl)-7-azabicyclo[2.2.1]-heptanes. Epibatidine Analogues". *J. Med. Chem.*2001, pp. 2229-2237, vol. 44.
Carroll et al., Synthesis, Nicotinic Acetylcholine Receptor Binding, and Antinocieptive Properties of 2-*exo* -2-(2'-Substituted 3'-phenyl-5'-pyridinyl)-7-azabicyclo[2.2.1]-heptanes. Novel Nicotinic Antagonist. *J. Med. Chem.*2001, pp. 4039-4041, vol. 44.
Fraley et al., "Optimization of a Pyrazolo[1,5-α]pyrimidine Class of KDR Kinase Inhibitors: Improvements in Physical Properties Enhance Cellular Activity and Pharmacokinetics", *Bioorganic& Medicinal Chemistry Letters*, 2002, pp. 3537-3541, vol.12.
Giantsidis et al., "Transition Metal Halide Salts of 2-Amino-5-Substituted-Pyridines: Synthesis, Crystal Structure and Magnetic Properties of Two Polymorphs of (5-IAP)$_2$ CuCl$_4$ [5-IAP = 2-Amino-5-Iodopyridinium]",*J. Coord. Chem.*, 2002, pp. 795-803, vol. 55, No.7.
Martin et al., "Highly Efficient Borylation Suzuki Coupling Process for 4-Bromo-2-Ketothiazoles: Straightforward Access to Micrococcinate and Saramycetate Esters", *Organic Letters*, 2009, pp. 3690-3693, vol. 11, No. 16.
Morgentin et al., "Strategic Studies in the Syntheses of Novel 6,7-substituted Quinolones and 7- or 6-substituted 1,6- and 1,7-naphthyridones", *Tetrahedron*, 2008, pp. 2772-2782, vol. 64.
Gao et al., "Derivatives of (–)-7-Methyl-2-(5-(pyridinyl)pyridine-3-yl)-7-azabicyclo[2.2.1]heptanes Are Potential Ligands for Positron Emission Tomography Imaging of Extrathalamic Nicotinic Acetylcholine Receptors", *J. Med. Chem.*, 2007, pp. 3814-3824, vol. 50.
Gao et al., "Discovery of (–)-Methyl-2-*exo*-[3'-(6-[$^{18}$F]fluoropyridin-2-yl)-5'—pyridinyl]-7-azabicyclo[2.2. 1]heptanes, a Radiolabeled Antagonist for Cerebral Nicotinic Acetylcholine Receptor 9α4β2-nAChR) with Optimal Positron Emission Tomography Imaging Properties", *J. Med. Chem.*, 2008, pp. 4751-4764, vol.51.
Gao et al., "Improved Syntheses of Precursors for PET Radioligands [$_{18}$F]XTRA and [$_{18}$F]AZAN", *Tetrahedron Letters*, 2010, pp. 5333-5335, vol. 51.

* cited by examiner

*Primary Examiner* — Nizal Chandrakumar
(74) *Attorney, Agent, or Firm* — Womble Carlyle Sandridge & Rice, LLP

(57) ABSTRACT

Provided herein are compounds and methods of preparation of compounds that are capable of functioning as agonists or antagonists of a nicotinic receptor. Also provided are pharmaceutical compositions comprising one or more of these compounds, which may further comprise one or more additional therapeutic agents. Further provided are methods of treatment of various conditions that may be responsive to such activity at the nicotinic receptors, such as nicotine dependence.

10 Claims, No Drawings

NICOTINIC RECEPTOR COMPOUNDS

CROSS-REFERENCE TO RELATED APPLICATIONS

The present application is a national stage entry of PCT international Application No. PCT/US2011/048470, filed Aug. 19, 2011, which claims the benefit of U.S. Provisional Application No. 61/375,630, filed Aug. 20, 2010. Both of these applications are incorporated by reference herein in their entireties.

FEDERALLY SPONSORED RESEARCH OR DEVELOPMENT

This invention was made with United States Government support under DA012001 awarded by the National Institutes of Health. The United States Government has certain rights in the invention.

FIELD OF THE INVENTION

The present application is directed to various compounds and methods of preparation of compounds that are capable of functioning as agonists or antagonists of the nicotinic receptors. The application is also directed to pharmaceutical compositions comprising one or more of these compounds, which may also comprise one or more additional therapeutic agents. It is further directed to methods of treatment of various conditions that may be responsive to modulation of the activation of nicotinic receptors, including methods directed to smoking cessation.

BACKGROUND OF THE INVENTION

Tobacco use is the leading preventable cause of disease, disability, and death in the United States. Cigarette smoking results in more than 400,000 premature deaths in the United States each year, accounting for about 1 in every 5 deaths according to the Centers for Disease Control 2008 Smoking and Tobacco Use Fact Sheet. Statistics from the U.S. Department of Health and Human Services show that, on average, adults who smoke die 14 years earlier than nonsmokers.

Cigarette smoking accounts for about one-third of all cancers, including 90% of lung cancer cases. Smoking also causes lung diseases such as chronic bronchitis and emphysema and increases the risk of stroke, heart attack, vascular disease, and aneurysm. In spite of these documented connections between tobacco use and disease, a large number of people continue to use tobacco products. In 2008, 28.6% of the U.S. population 12 years of age and older (70.9 million people) had used a tobacco product at least once in the month prior to being interviewed. This figure includes 3.1 million young people aged 12-17 (12.4% of this age group).

Nicotine is considered the main psychoactive component in tobacco smoke that causes people to use and continue to use tobacco products. The pharmacological and behavioral effects result from interaction with different nicotinic acetylcholine receptor (nAChR) subtypes. The subtypes are either homo or hetero pentameric ion channels, consisting of different combinations of genetically distinct subunits, ($\alpha 1$, $\alpha 2$-$\alpha 10$, $\beta 1$-$\beta 4$, $\gamma$, $\delta$, $\epsilon$). The predominant nAChR subtypes found in the brain are thought to be heteromeric $\alpha 4\beta 2$ nAChR or homomeric $\alpha 7$-nAChR; however, appreciable amounts of $\alpha 3\beta 4^*$ and $\alpha 6\beta 2^*$ nAChRs (where the * indicate that other subunits are known or possible assembly partners with those specified) also are in brain regions implicated in reward and drug dependence.

Nicotine exposure can stimulate activity of somatodendritic nAChRs to alter neuronal electrical activity and neurotransmitter release as a consequence of neuronal activation. However, by acting at nAChRs positioned on nerve terminals, nicotine also can increase neurotransmitter release as a consequence of local depolarization of the nerve terminal membrane potential and/or calcium ion mobilization in terminals. The integration of these effects is likely to contribute to nicotine's actions, including those that are presumably involved in its reinforcement of tobacco product use, such as effects in monoaminergic reward pathways.

Even though nicotine dependence has a huge impact on global health, pharmacotherapies for treating tobacco use are limited. Current treatments include nicotine-replacement therapies (NRTs), bupropion, and varenicline. Since only about one-fifth of smokers are able to maintain long-term (12 months) abstinence with any of the present pharmacotherapies, there is a need in the art for new and improved pharmaceutical compositions for treating drug addiction.

It is thought to be possible that specific subtypes of nAChRs mediate specific functions, especially as this relates to nicotine addiction. Thus, it would be beneficial to provide a variety of ligands that bind with high affinity and selectivity for each nAChR subtype. Both agonists and antagonists of the various subtypes of nAChRs are desirable since the role of nAChRs in addiction is not known. A number of compounds having activity at one or more nAChR subtype have been studied as potential smoking cessation agents. For example, epibatidine is a nicotinic agonist whose biological effects appear to be mediated by $\alpha_4\beta_2$ nAChRs. However, epibatidine exhibits toxicity that precludes its use in humans. Some analogs of epibatidine have been prepared and studied in an attempt to maintain the activity of epibatidine but eliminate its toxicity (see for example, U.S. Pat. No. 6,538,010 and U.S. Pat. No. 7,615,567, incorporated herein by reference). However, there exists a need for additional such analogs, which may be potent and/or selective for specific nAChRs (e.g., the $\alpha_4\beta_2$ nAChR), and which could therefore provide alternative therapeutics for the treatment of nicotine dependence.

BRIEF SUMMARY OF THE INVENTION

The present invention relates generally to compounds that may be useful as agonists and/or antagonists of the nicotine receptors. It also relates to pharmaceutical formulations of such compounds and to methods of using such compounds or formulations thereof to treat nicotine dependence or other various conditions that may be responsive to modulation of the activation of nicotinic receptors.

In one aspect of the invention is provided a compound according to the following structure:

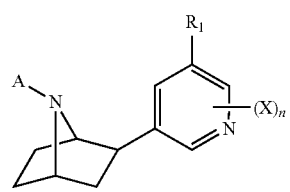

wherein:
A is —R, —N(R)$_2$, —C(=NR)N(R)$_2$, or —OR,
each R is, independently, H, alkyl, alkenyl, alkynyl, aryl, or aralkyl;

each X is, independently, H, halo, alkyl, alkenyl, alkynyl, aralkyl, —OR, —CH$_2$—CO$_2$R, —C(O)R, —CO$_2$R, —N(R)$_2$, —NR—C(O)R, —C(O)N(R)$_2$, —NR—CO$_2$R, —SO$_3$CF$_3$, —NO$_2$, —N$_3$, —CF$_3$, —CH=CHY, or —CN;

Y is halo;

n is an integer from 0-3; and

R$_1$ is an optionally substituted heteroaryl;

or a pharmaceutically acceptable ester, amide, salt, solvate, prodrug, or isomer thereof.

In certain embodiments, a compound is provided wherein R$_1$ is selected from the group consisting of optionally substituted thiophene, pyrrole, furan, oxazole, pyrazole, imidazole, thiazole, purine, triazole, thiadiazole, pyridine, quinoline, isoquinoline, phenanthrine, 5,6-cycloheptenopyridine, pyridazine, cinnoline, phthalazine, pyrazine, pyrimidine, quinazoline, and 1,3,5-triazine. In certain embodiments, R$_1$ is pyrimidine. For example, in one particular embodiment, R$_1$ is pyrimidine, X is halo, n=1, and A is H.

In certain embodiments, a compound of the following structure is provided:

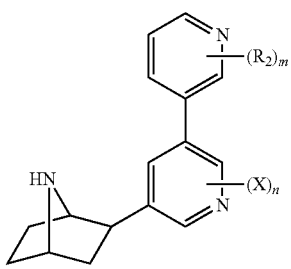

wherein:

each X is, independently, H or a halo substituent;

n is an integer from 0-3;

each R$_2$ is independently selected from the group consisting of H, C1-6 alkoxy, amino, halo, hydroxyl, amide, CN, CH$_3$SO$_2$, and CF$_3$SO$_2$; and m is an integer from 0-4;

or a pharmaceutically acceptable ester, amide, salt, solvate, prodrug, or isomer thereof.

In other certain embodiments, a compound of the following structure is provided:

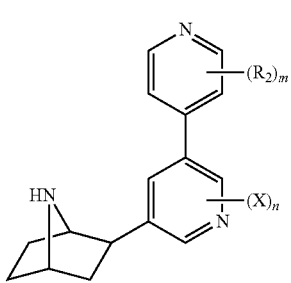

wherein:

each X is, independently, H or a halo substituent;

n is an integer from 0-3;

each R$_2$ is independently selected from the group consisting of H, C1-6 alkoxy, amino, halo, hydroxyl, amide, CN, CH$_3$SO$_2$, and CF$_3$SO$_2$; and m is an integer from 0-4;

or a pharmaceutically acceptable ester, amide, salt, solvate, prodrug, or isomer thereof.

In further embodiments, a compound of the following structure is provided:

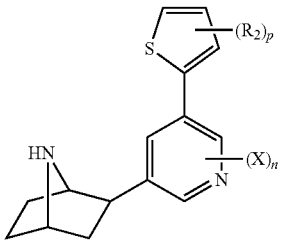

wherein:

each X is, independently, H or a halo substituent;

n is an integer from 0-3;

each R$_2$ is independently selected from the group consisting of H, C1-6 alkoxy, amino, halo, hydroxyl, amide, CN, CH$_3$SO$_2$, and CF$_3$SO$_2$; and p is an integer from 0-3;

or a pharmaceutically acceptable ester, amide, salt, solvate, prodrug, or isomer thereof.

In still further embodiments of the invention, a compound of the following structure is provided:

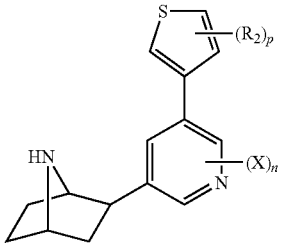

wherein:

each X is, independently, H or a halo substituent;

n is an integer from 0-3;

each R$_2$ is independently selected from the group consisting of H, C1-6 alkoxy, amino, halo, hydroxyl, amide, CN, CH$_3$SO$_2$, and CF$_3$SO$_2$; and p is an integer from 0-3;

or a pharmaceutically acceptable ester, amide, salt, solvate, prodrug, or isomer thereof.

In certain embodiments, specific compounds are provided, wherein the compounds are selected from the group consisting of:

2-exo-[2'-Fluoro-3'-(2-fluoropyridin-4-yl)-5'-pyridinyl]-7-azabicyclo[2.2.1]heptane;

2-exo-[2'-Fluoro-3'-(2-chloropyridin-4-yl)-5'-pyridinyl]-7-azabicyclo[2.2.1]heptane;

2-exo-[2'-Fluoro-3'-(6-fluoropyridin-3-yl)-5'-pyridinyl]-7-azabicyclo[2.2.1]heptane;

2-exo-[2'-Fluoro-3'-(6-chloropyridin-3-yl)-5'-pyridinyl]-7-azabicyclo[2.2.1]heptane;

2-exo-[2'-Fluoro-3'-(pyridin-4-yl)-5'-pyridinyl]-7-azabicyclo[2.2.1]heptane;

2-exo-[2'-Fluoro-3'-(pyridin-3-yl)-5'-pyridinyl]-7-azabicyclo[2.2.1]heptane;

2-exo-[2'-Fluoro-3'-(6-methoxypyridin-3-yl)-5'-pyridinyl]-7-azabicyclo[2.2.1]heptane; 2'-Fluoro-3'-(2"-amino-5"-pyridinyl)deschloroepibatidine;

2-exo-[2'-Fluoro-3'-(2-methoxypyridin-4-yl)-5'-pyridinyl]-7-azabicyclo[2.2.1]heptane;
2-Fluoro-3-(2'-amino-4'-pyridinyl)deschloroepibatidine;
2-exo-[3'-(2-Chloropyridin-4-yl)-5'-pyridinyl]-7-azabicyclo[2.2.1]heptane;
2-exo-[3'-(2-Fluoropyridin-4-yl)-5'-pyridinyl]-7-azabicyclo[2.2.1]heptane;
2-exo-[3'-(Pyridin-4-yl)-5'-pyridinyl]-7-azabicyclo[2.2.1]heptane;
2-exo-[3'-(2-Aminopyridin-4-yl)-5'-pyridinyl]-7-azabicyclo[2.2.1]heptane;
2-exo-[3'-(2-Methoxypyridin-4-yl)-5'-pyridinyl]-7-azabicyclo[2.2.1]heptane;
2-exo-[2'-Fluoro-3'-(pyrimidin-3-yl)-5'-pyridinyl]-7-azabicyclo[2.2.1]heptane;
2-exo-[2'-Chloro-3'-(pyrimidin-5-yl)-5'-pyridinyl]-7-azabicyclo[2.2.1]heptane;
2-exo-[3'-(Pyrimidin-5-yl)-5'-pyridinyl]-7-azabicyclo[2.2.1]heptane;
2-exo-[2'-Fluoro-3'-(pyridazin-4-yl)-5'-pyridinyl]-7-azabicyclo[2.2.1]heptane;
2-exo-[2'-Chloro-3'-(pyridazin-4-yl)-5'-pyridinyl]-7-azabicyclo[2.2.1]heptane;
2-exo-[3'-(Pyridazin-4-yl)-5'-pyridinyl]-7-azabicyclo[2.2.1]heptane;
2-exo-[2'-Fluoro-3'-(thiophen-2-yl)-5'-pyridinyl]-7-azabicyclo[2.2.1]heptane;
2-exo-[2'-Fluoro-3'-(5-fluorothiophen-2-yl)-5'-pyridinyl]-7-azabicyclo[2.2.1]heptane;
2-exo-[2'-Fluoro-3'-(5-chlorothiophen-2-yl)-5'-pyridinyl]-7-azabicyclo[2.2.1]heptane;
2-exo-[2'-Fluoro-3'-(5-aminothiophen-2-yl)-5'-pyridinyl]-7-azabicyclo[2.2.1]heptane;
2-exo-[2'-Fluoro-3'-(5-methoxythiophen-2-yl)-5'-pyridinyl]-7-azabicyclo[2.2.1]heptane;
2-exo-[2'-Fluoro-3'-(4-fluorothiophen-2-yl)-5'-pyridinyl]-7-azabicyclo[2.2.1]heptane;
2-exo-[2'-Fluoro-3'-(4-chlorothiophen-2-yl)-5'-pyridinyl]-7-azabicyclo[2.2.1]heptane;
2-exo-[2'-Fluoro-3'-(4-aminothiophen-2-yl)-5'-pyridinyl]-7-azabicyclo[2.2.1]heptane;
2-exo-[2'-Fluoro-3'-(4-methoxythiophen-2-yl)-5'-pyridinyl]-7-azabicyclo[2.2.1]heptane;
2-exo-[2'-Fluoro-3'-(thiophen-3-yl)-5'-pyridinyl]-7-azabicyclo[2.2.1]heptane;
2-exo-[2'-Fluoro-3'-(5-fluorothiophen-3-yl)-5'-pyridinyl]-7-azabicyclo[2.2.1]heptane;
2-exo-[2'-Fluoro-3'-(5-chlorothiophen-3-yl)-5'-pyridinyl]-7-azabicyclo[2.2.1]heptane;
2-exo-[2'-Fluoro-3'-(5-aminothiophen-3-yl)-5'-pyridinyl]-7-azabicyclo[2.2.1]heptane;
2-exo-[2'-Fluoro-3'-(5-methoxythiophen-3-yl)-5'-pyridinyl]-7-azabicyclo[2.2.1]heptane;
2-exo-[2'-Fluoro-3'-(6-fluoropyridin-3-yl)-5'-pyridinyl]-7-azabicyclo[2.2.1]heptane;
2-exo-[2'-Fluoro-3'-(6-chloropyridin-3-yl)-5'-pyridinyl]-7-azabicyclo[2.2.1]heptane;
2-Fluoro-3-(2'-fluoro-4'-pyridinyl)deschloroepibatidine;
2-Fluoro-3-(2'-chloro-4'-pyridinyl)deschloroepibatidine; and
2-Fluoro-3-(4'-pyridinyl)deschloroepibatidine.

In another aspect of the invention is provided a method for treating or delaying the progression of disorders that are alleviated by agonizing or antagonizing the nicotinic acetylcholine receptor by administering a therapeutically effective amount of at least one compound of the invention. In some embodiments, the disorder to be treated may be addiction (e.g, nicotine dependence), Alzheimer's disease, Parkinson's disease, pain (analgesic activity), depression, Tourette's syndrome, inflammatory bowel syndrome, schizophrenia, anxiety, epilepsy, attention-deficit hyperactivity disorder, ulcerative colitis, or obesity. In a still further aspect of the invention is provided a pharmaceutical composition comprising a compound of the invention and one or more pharmaceutically acceptable carriers.

DETAILED DESCRIPTION OF THE INVENTION

Many modifications and other embodiments of the inventions set forth herein will come to mind to one skilled in the art to which these inventions pertain having the benefit of the teachings presented herein. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. As used in the specification, and in the appended claims, the singular forms "a", "an", "the", include plural referents unless the context clearly dictates otherwise.

The present invention provides compounds that may function as agonists and/or antagonists of the nicotinic acetylcholine receptor (nAChR). The invention also provides methods of preparation and pharmaceutical compositions thereof. It also provides methods for using such compounds to treat a variety of disorders that may be responsive to modulation of the activation of nicotinic receptors (i.e., activation of the receptor or partial or complete deactivation of the receptor). Thus, the compounds of the present invention may interact with nicotinic receptors; for example, they may act as agonists and/or antagonists of the nicotinic receptors. In certain embodiments, the compounds may act as partial agonists, which may have both agonist and antagonist activity. In particular, the compositions and methods can be used to treat nicotine dependence (e.g., aid in smoking cessation). In some embodiments, treatment can comprise the use of a compound of the present invention as a single active agent. In other embodiments, treatment can comprise the use of a compound of the present invention in combination with one or more further active agents. The specific pharmaceutical composition (or compositions) used in the invention, and the methods of treatment provided by the invention, are further described below.

Definitions

The term "alkyl" as used herein means saturated straight, branched, or cyclic hydrocarbon groups. In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), 1 to 4 carbon atoms ("C1-4 alkyl"), or 1 to 3 carbon atoms ("C1-3 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl includes alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy;

aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms (C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "aryl" as used herein means a stable monocyclic, bicyclic, or tricyclic carbon ring of up to 8 members in each ring, wherein at least one ring is aromatic as defined by the Hückel 4n+2 rule.

The term "heteroaryl" as used herein means an aryl group containing from one or more (particularly one to four) non-carbon atom(s) (particularly N or S) or a combination thereof, which heteroaryl group is optionally substituted at one or more carbon or nitrogen atom(s) with alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

The term "halo" or "halogen" as used herein means fluorine, chlorine, bromine, or iodine.

The term "alkylthio" as used herein means a thio group with one or more alkyl substituents, where alkyl is defined as above.

The term "acylamido" refers to an amide group with one or more acyl substituents, where acyl is as defined below.

The term "acyl" as used herein means a group formed by removing the hydroxyl group from a carboxylic acid, in which the non-carbonyl moiety of the group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, C1-6 alkyl or C1-6 alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl.

The terms "aralkyl" and "arylalkyl" as used herein mean an aryl group as defined above linked to the molecule through an alkyl group as defined above.

The term "amino" as used herein means a moiety represented by the structure $NR_2$, and includes primary amines, and secondary and tertiary amines substituted by alkyl (i.e., alkylamino). Thus, $R_2$ may represent, for example, two hydrogen atoms, two alkyl moieties, or one hydrogen atom and one alkyl moiety.

The term "cycloalkyl" means a non-aromatic, monocyclic or polycyclic ring comprising carbon and hydrogen atoms. Substituted cycloalkyl includes alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

"Optionally substituted" in reference to a substituent group refers to substituent groups optionally substituted with one or more moieties, for example, those selected from the group consisting of optionally substituted C1-10 alkyl (e.g., optionally substituted C1-6 alkyl); optionally substituted C1-10 alkoxy (e.g., optionally substituted C1-6 alkoxy); optionally substituted C2-10 alkenyl; optionally substituted C2-10 alkynyl; optionally substituted C6-C12 aryl; aryloxy; optionally substituted heteroaryl; optionally substituted heterocycle; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR_{12}H$, and $NR_{12}R_{13}$); alkylamino; arylamino; acyl; amido; CN; $NO_2$; $N_3$; $CH_2OH$; $CONH_2$; $CONR_{12}R_{13}$; $CO_2R_{12}$, $CH_2OR_{12}$; $NHCOR_{12}$; $NHCO_2R_{12}$; C1-3 alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R_{12}SO$; $R_{12}SO_2$; $CF_3S$; and $CF_3SO_2$; trialkylsilyl such as dimethyl-t-butylsilyl or diphenylmethylsilyl; and $R_{12}$ and $R_{13}$ are each independently selected from H or optionally substituted C1-10 alkyl.

The term "analogue," used interchangeably with the term "analog" herein, means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

Active Agents

The present invention provides compounds, methods of preparation of the compounds, pharmaceutical compositions, and methods of treatment of various conditions using such compounds and pharmaceutical compositions.

In certain embodiments, a compound of Formula I is provided:

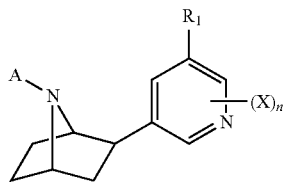

Formula I wherein:
A is —R, —N(R)$_2$, —C(=NR)N(R)$_2$, or —OR,
each R is, independently, H, alkyl, alkenyl, alkynyl, aryl, or aralkyl;
each X is, independently, H, halo, alkyl, alkenyl, alkynyl, aralkyl, —OR, —CH$_2$—CO$_2$R, —C(O)R, —CO$_2$R, —N(R)$_2$, —NR—C(O)R, amide (i.e., —C(O)N(R)$_2$), —NR—CO$_2$R, —SO$_3$CF$_3$, —NO$_2$, —N$_3$, —CF$_3$, —CH=CHY, or —CN;
Y is halo;
n is an integer from 0-3; and
R$_1$ is an optionally substituted heteroaryl;
or a pharmaceutically acceptable ester, amide, salt, solvate, prodrug, or isomer thereof.

In certain embodiments, n=1. In specific embodiments, the pyridyl ring is substituted at the carbon between the N and the carbon to which R$_1$ is attached. In certain embodiments, the substituent X is H, Cl, or F. In certain embodiments, the optionally substituted heteroaryl has one or more substituents. Substituents may include, but are not limited to, optionally substituted C1-10 alkyl (e.g., optionally substituted C1-6 alkyl); optionally substituted C1-10 alkoxy (e.g., optionally substituted C1-6 alkoxy); optionally substituted C2-10 alkenyl; optionally substituted C2-10 alkynyl; optionally substituted C6-C12 aryl; aryloxy; optionally substituted heteroaryl; optionally substituted heterocycle; halo (e.g., Cl, F, Br, and I); hydroxyl; halogenated alkyl (e.g., CF$_3$, 2-Br-ethyl, CH$_2$F, CH$_2$CF$_3$, and CF$_2$CF$_3$); amino (e.g., NH$_2$, NR$_{12}$H, and NR$_{12}$R$_{13}$); alkylamino; arylamino; acyl; amido; CN; NO$_2$; N$_3$; CH$_2$OH; CONH$_2$; CONR$_{12}$R$_{13}$; CO$_2$R$_{12}$; CH$_2$OR$_{12}$; NHCOR$_{12}$; NHCO$_2$R$_{12}$; C1-3 alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; R$_{12}$R$_{13}$NSO$_2$ (including H$_2$NSO$_2$); R$_{12}$SO; R$_{12}$SO$_2$; CF$_3$S; and CF$_3$SO$_2$; trialkylsilyl such as dimethyl-t-butylsilyl or diphenylmethylsilyl; and R$_{12}$ and R$_{13}$ are each independently selected from H or optionally substituted C1-10 alkyl. In specific embodiments, the optionally substituted heteroaryl has one substituent. In some preferred embodiments, the optionally substituted heteroaryl has one or more halo (e.g., F or Cl) substituents. In some preferred embodiments, the optionally substituted heteroaryl has one or more amino substituents. In some preferred embodiments, the optionally substituted heteroaryl has one or more alkoxy substituents. The optional substituents on the heteoaryl may further be substituted with any type of substituent as indicated above.

In certain embodiments, R$_1$ is an optionally substituted pyridine. The nitrogen of the pyridine may be at any position on the ring. For example, in some embodiments, the compound may be a compound of Formula Ia:

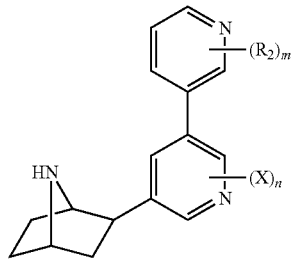

Formula Ia wherein:
each X is, independently, any of the substituents listed for X in Formula I, with preferred X substituents being H or halo;
n is an integer from 0-3;
each R$_2$ is, independently, any of the substituents set forth above, with preferred R$_2$ substituents H, C1-6 alkoxy, amino, halo, hydroxyl, amide, CN, CH$_3$SO$_2$, and CF$_3$SO$_2$; and
m is an integer from 0-4;
or a pharmaceutically acceptable ester, amide, salt, solvate, prodrug, or isomer thereof.

In some preferred embodiments of Formula Ia, m=1. In certain specific embodiments wherein m=1, the R$_2$ substituent is located on the carbon adjacent to the N of the ring and para to the remainder of the molecule.

In some other embodiments, the compound may be a compound of Formula Ib:

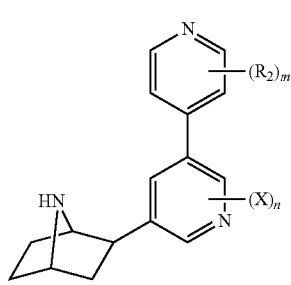

Formula Ib wherein:
each X is, independently, any of the substituents listed for X in Formula I, with preferred X substituents being H or halo;
n is an integer from 0-3;
each $R_2$ is, independently, any of the substituents set forth above, with preferred $R_2$ substituents H, C1-6 alkoxy, amino, halo, hydroxyl, amide, CN, $CH_3SO_2$, and $CF_3SO_2$; and
m is an integer from 0-4;
or a pharmaceutically acceptable ester, amide, salt, solvate, prodrug, or isomer thereof.

In preferred embodiments of Formula Ib, m=1. In certain specific embodiments wherein m=1, the $R_2$ substituent is located on a carbon adjacent to the N.

In certain embodiments, $R_1$ is an optionally substituted thiophene. The sulfur atom may be located at any position on the ring. For example, in some embodiments, the compound may be a compound of Formula Ic:

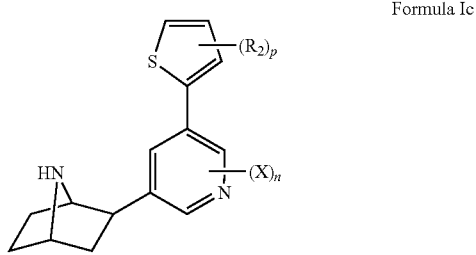

Formula Ic wherein:
each X is, independently, any of the substituents listed for X in Formula I, with preferred X substituents being H or halo;
n is an integer from 0-3;
each $R_2$ is, independently, any of the substituents set forth above, with preferred $R_2$ substituents H, C1-6 alkoxy, amino, halo, hydroxyl, amide, CN, $CH_3SO_2$, and $CF_3SO_2$; and
p is an integer from 0-3;
or a pharmaceutically acceptable ester, amide, salt, solvate, prodrug, or isomer thereof.

In some preferred embodiments of Formula Ic, p=1. In certain specific embodiments wherein p=1, the $R_2$ substituent is located on the carbon adjacent to the S. In certain specific embodiments wherein p=1, the $R_2$ substituent is located on the carbon that is neither adjacent to the S nor to the remainder of the molecule.

In some other embodiments, the compound may be a compound of Formula Id:

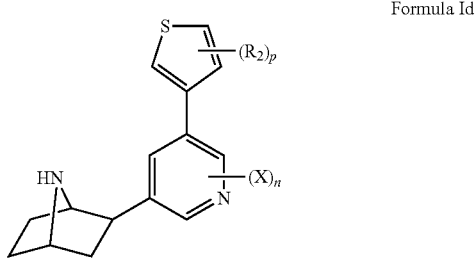

Formula Id wherein:
each X is, independently, any of the substituents listed for X in Formula I, with preferred X substituents being H or halo;
n is an integer from 0-3;
each $R_2$ is, independently, any of the substituents set forth above, with preferred $R_2$ substituents H, C1-6 alkoxy, amino, halo, hydroxyl, amide, CN, $CH_3SO_2$, and $CF_3SO_2$; and
p is an integer from 0-3;
or a pharmaceutically acceptable ester, amide, salt, solvate, prodrug, or isomer thereof.

In some preferred embodiments of Formula Id, p=1. In certain specific embodiments wherein p=1, the $R_2$ substituent is located on the carbon adjacent to the S but not to the remainder of the molecule.

In some embodiments of the present invention, therapeutically inactive prodrugs are provided. Prodrugs are compounds which, when administered to a mammal, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, may reduce polarity and allow for the compound's passage into cells. Examples of substituent groups that can replace one or more hydrogen atoms on a free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine. Any of these moieties can be used in combination with the disclosed active agents to achieve a desired effect.

In some embodiments, compounds with one or more chiral centers are provided. While racemic mixtures of compounds of the invention may be active, selective, and bioavailable, isolated isomers may be of interest as well.

The compounds disclosed herein as active agents may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular, to the extent of 95% or more, 96% or more, 97% or more, 98% or more, or 99% or more, including 100%.

The terms (R), (S), (R,R), (S,S), (R,S) and (S,R) as used herein mean that the composition contains a greater proportion of the named isomer of the compound in relation to other isomers. In a preferred embodiment, these terms indicate that the composition contains at least 90% by weight of the named isomer and 10% by weight or less of the one or more other isomers; or more preferably about 95% by weight of the named isomer and 5% or less of the one or more other isomers. In some embodiments, the composition may contain at least 99% by weight of the named isomer and 1% or less by weight of the one or more other isomers, or may contain 100% by weight of the named isomer and 0% by weight of the one of more other isomers. These percentages are based on the total amount of the compound of the present invention present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from an anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

Some representative, non-limiting compounds of the present invention include the following 4-pyridine-substituted epibatidine compounds according to Formula Ia.

TABLE 1

Representative compounds of Formula Ia

| X | $R_2$ |
|---|---|
| H | H |
| H | F |
| H | Cl |
| H | Br |
| H | $NH_2$ |
| H | $N(CH_3)H$ |
| H | $N(CH_3)_2$ |
| H | $N(CH_2CH_3)H$ |
| H | $N(CH_2CH_3)_2$ |
| H | $CH_3O$ |
| H | $CH_3CH_2O$ |
| H | $CH_3CH_2CH_2O$ |
| H | $CH_3SO_2$ |
| H | $CF_3SO_2$ |
| H | CN |
| H | $H_2NSO_2$ |
| F | H |
| F | F |
| F | Cl |
| F | Br |
| F | $NH_2$ |
| F | $N(CH_3)H$ |
| F | $N(CH_3)_2$ |
| F | $N(CH_2CH_3)H$ |
| F | $N(CH_2CH_3)_2$ |
| F | $CH_3O$ |
| F | $CH_3CH_2O$ |
| F | $CH_3CH_2CH_2O$ |
| F | $CH_3SO_2$ |
| F | $CF_3SO_2$ |
| F | CN |
| F | $H_2NSO_2$ |

Other representative, non-limiting compounds of the present invention include the following 3-pyridine-substituted epibatidine compounds according to Formula Ib.

TABLE 2

Representative compounds of Formula Ib

| X | R₂ |
|---|---|
| H | H |
| H | F |
| H | Cl |
| H | Br |
| H | NH$_2$ |
| H | N(CH$_3$)H |
| H | N(CH$_3$)$_2$ |
| H | N(CH$_2$CH$_3$)H |
| H | N(CH$_2$CH$_3$)$_2$ |
| H | CH$_3$O |
| H | CH$_3$CH$_2$O |
| H | CH$_3$CH$_2$CH$_2$O |
| H | CH$_3$SO$_2$ |
| H | CF$_3$SO$_2$ |
| H | CN |
| H | H$_2$NSO$_2$ |
| F | H |
| F | F |
| F | Cl |
| F | Br |
| F | NH$_2$ |
| F | N(CH$_3$)H |
| F | N(CH$_3$)$_2$ |
| F | N(CH$_2$CH$_3$)H |
| F | N(CH$_2$CH$_3$)$_2$ |
| F | CH$_3$O |
| F | CH$_3$CH$_2$O |
| F | CH$_3$CH$_2$CH$_2$O |
| F | CH$_3$SO$_2$ |
| F | CF$_3$SO$_2$ |
| F | CN |
| F | H$_2$NSO$_2$ |

TABLE 3

Representative compounds of Formula Ic

| X | R₂ |
|---|---|
| H | H |
| H | F |
| H | Cl |
| H | Br |
| H | NH$_2$ |
| H | N(CH$_3$)H |
| H | N(CH$_3$)$_2$ |
| H | N(CH$_2$CH$_3$)H |
| H | N(CH$_2$CH$_3$)$_2$ |
| H | CH$_3$O |
| H | CH$_3$CH$_2$O |
| H | CH$_3$CH$_2$CH$_2$O |
| H | CH$_3$SO$_2$ |
| H | CF$_3$SO$_2$ |
| H | CN |
| H | H$_2$NSO$_2$ |
| F | H |
| F | F |
| F | Cl |
| F | Br |
| F | NH$_2$ |
| F | N(CH$_3$)H |
| F | N(CH$_3$)$_2$ |
| F | N(CH$_2$CH$_3$)H |
| F | N(CH$_2$CH$_3$)$_2$ |
| F | CH$_3$O |
| F | CH$_3$CH$_2$O |
| F | CH$_3$CH$_2$CH$_2$O |
| F | CH$_3$SO$_2$ |
| F | CF$_3$SO$_2$ |
| F | CN |
| F | H$_2$NSO$_2$ |

Further representative, non-limiting compounds of the present invention include the following 2-thiophene-substituted epibatidine compounds according to Formula Ic.

Further representative, non-limiting compounds of the present invention include the following 2-thiophene-substituted epibatidine compounds according to Formula Ic.

TABLE 4

Representative compounds of Formula Ic

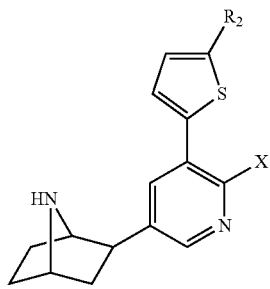

| X | R₂ |
|---|---|
| H | H |
| H | F |
| H | Cl |
| H | Br |
| H | $NH_2$ |
| H | $N(CH_3)H$ |
| H | $N(CH_3)_2$ |
| H | $N(CH_2CH_3)H$ |
| H | $N(CH_2CH_3)_2$ |
| H | $CH_3O$ |
| H | $CH_3CH_2O$ |
| H | $CH_3CH_2CH_2O$ |
| H | $CH_3SO_2$ |
| H | $CF_3SO_2$ |
| H | CN |
| H | $H_2NSO_2$ |
| F | H |
| F | F |
| F | Cl |
| F | Br |
| F | $NH_2$ |
| F | $N(CH_3)H$ |
| F | $N(CH_3)_2$ |
| F | $N(CH_2CH_3)H$ |
| F | $N(CH_2CH_3)_2$ |
| F | $CH_3O$ |
| F | $CH_3CH_2O$ |
| F | $CH_3CH_2CH_2O$ |
| F | $CH_3SO_2$ |
| F | $CF_3SO_2$ |
| F | CN |
| F | $H_2NSO_2$ |

Further representative, non-limiting compounds of the present invention include the following 3-thiophene-substituted epibatidine compounds according to Formula Id.

TABLE 5

Representative compounds of Formula Id

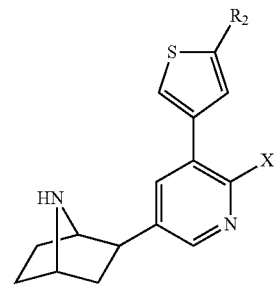

| X | R₂ |
|---|---|
| H | H |
| H | F |
| H | Cl |
| H | Br |
| H | $NH_2$ |
| H | $N(CH_3)H$ |
| H | $N(CH_3)_2$ |
| H | $N(CH_2CH_3)H$ |
| H | $N(CH_2CH_3)_2$ |
| H | $CH_3O$ |
| H | $CH_3CH_2O$ |
| H | $CH_3CH_2CH_2O$ |
| H | $CH_3SO_2$ |
| H | $CF_3SO_2$ |
| H | CN |
| H | $H_2NSO_2$ |
| F | H |
| F | F |
| F | Cl |
| F | Br |
| F | $NH_2$ |
| F | $N(CH_3)H$ |
| F | $N(CH_3)_2$ |
| F | $N(CH_2CH_3)H$ |
| F | $N(CH_2CH_3)_2$ |
| F | $CH_3O$ |
| F | $CH_3CH_2O$ |
| F | $CH_3CH_2CH_2O$ |
| F | $CH_3SO_2$ |
| F | $CF_3SO_2$ |
| F | CN |
| F | $H_2NSO_2$ |

The compounds of the present invention may display different types of biological activities. In some embodiments, the compounds of the present invention may be capable of acting as agonists and/or antagonists of one or more nicotinic acetylcholine receptors. For example, in some embodiments, the compounds may function as agonists by binding to nAChRs. For example, in other embodiments, the compounds may function as antagonists by binding either to the active site or to an alternative site on the receptor, inhibiting the ability of agonists (e.g., nicotine) to interact with the receptor. In certain embodiments, the compounds of the present invention may show enhanced selectivity for one or more types of nicotinic receptor. In some embodiments, the compounds may be selective for $\alpha_4\beta_2$ nAChRs. In certain specific embodiments, some compounds of the invention may act as noncompetitive functional antagonists at the $\alpha_4\beta_2$ nAChRs.

Methods of Preparation

The present invention also encompasses methods of preparing compounds with structures encompassed by Formula I, including but not limited to compounds with structures according to Formulae Ia, Ib, Ic, and Id. Representative synthetic procedures for preparing compounds of the present invention are provided in Schemes 1-18 in the Experimental section. One of skill in the art would be able to adapt these methods as required to accommodate various functional groups that may affect the chemistry of the synthesis.

Compositions

While it is possible for the compounds of the present invention to be administered in the raw chemical form, it is preferred for the compounds to be delivered as a pharmaceutical formulation. Accordingly, there are provided by the present invention pharmaceutical compositions comprising at least one compound capable of acting as an agonist or antagonist of the nicotinic receptors. As such, the formulations of the present invention comprise a compound of any of the formulas noted herein, as described above, or a pharmaceutically acceptable ester, amide, salt, or solvate thereof, together with one or more pharmaceutically acceptable carriers therefor, and optionally, other therapeutic ingredients.

By "pharmaceutically acceptable carrier" is intended a carrier, adjuvant, accessory, or excipient that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Adjuvants or accessory ingredients for use in the formulations of the present invention can include any pharmaceutical ingredient commonly deemed acceptable in the art, such as fillers, stabilizers, diluents, buffers, binders, disintegrants, thickeners, lubricants, preservatives (including antioxidants), flavoring and coloring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Exemplary excipients include water, saline, dextrose, glycerol, ethanol, and combinations thereof. Other exemplary pharmaceutical excipients and/or additives suitable for use in the compositions according to the invention are listed in Remington: The Science & Practice of Pharmacy, 21$^{st}$ ed., Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and crosslinked polymers.

Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated. However, in preferred embodiments, the formulation is for oral delivery, as oral administration may provide the drug while maintaining abuse resistance.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula I according to the present invention (or a pharmaceutically acceptable ester, amide, salt, or solvate thereof), with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The amount of the compound of any one of the formulas disclosed herein contained in the formulation will vary depending the specific compound or prodrug selected, dosage form, target patient population, and other considerations, and will be readily determined by one skilled in the art. The amount of the compound in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds of the present invention comprise one or more compounds generally recognized as useful for treating the conditions discussed herein. In one embodiment, the use of two or more drugs, which may be of different therapeutic classes, may enhance efficacy and/or reduce adverse effects associated with one or more of the drugs.

For example, in certain embodiments, the present invention provides compositions for treating nicotine dependence, comprising a combination of a compound of the present invention and one or more known nicotine dependence drugs. For example, a compound of the present invention may be used in combination with bupropion and/or varenicline. The compounds disclosed herein may also be used in combination with one or more type of nicotinic replacement therapy (NRT). For example, in certain embodiments, the compounds of the present invention may be used in combination with a nicotine patch, nicotine inhaler, nasal spray, gum, sublingual tablet, and/or lozenge).

In certain embodiments, a compound of Formula I may also be combined with one or more nicotinic drugs. One particular class of nicotinic drugs that may be used with compounds of the present invention encompasses $\alpha4$-$\beta2$ nicotinic receptor partial agonists, including varenicline (CHANTIX®). Another nicotinic drug approved for the treatment of nicotine dependence, bupropion (ZYBAN®), which is an $\alpha3$-$\beta4$ nicotinic receptor antagonist, may be combined with any of the compounds provided herein.

In some embodiments, other compounds that have demonstrated off-label success for smoking cessation may be combined with compounds of Formula I. Other drug therapies that may be prescribed and used in nicotine dependence in combination with the compounds of the present invention include nortriptyline and doxepin, both tricyclic antidepressants. Additionally, fluoxetine (PROZAC®) and buspirone (BUSPAR®) have been used to treat nicotine addiction. Clonidine, an $\alpha2$-noradrenergic agonist used to treat hypertension, has also shown beneficial effects in nicotine addiction and studies suggest that mecamylamine may also aid in treatment for nicotine addiction. Immunotherapy may also be used in conjunction with compounds of the present invention, as recent studies have demonstrated a prototype vaccine against nicotine that may induce the production of antibodies that bind nicotine in the blood, preventing it from reaching the nicotine receptors.

In some embodiments, compounds of the present invention are used in conjunction with behavioral treatment. For example, psychological treatment (including, but not limited to, psychological counseling, group therapy, and/or behavior therapy), skills training to deal with high-risk situations as well as an exercise regimen may prove effective at treating nicotine dependence when used in combination with treatment using a compound of the present invention.

Combinations of compounds of the present invention with other therapeutic agents are also included in the present invention, wherein the condition to be treated is responsive to a change in the activation of the nicotinic acetylcholine receptors. For example, it may relate to treatment of Alzheimer's disease, Parkinson's disease, pain (analgesic activity), depression, Tourette's syndrome, inflammatory bowel syndrome, schizophrenia, anxiety, epilepsy, attention-deficit hyperactivity disorder, ulcerative colitis and obesity. Accordingly, the present invention also provides compositions for treating these conditions that may comprise a combination of a compound of the present invention and one or more additional compounds. All combinations of compounds or drugs of the present invention with other therapeutic agents are included in the present invention, wherein the condition to be treated is any condition that may be responsive to modulation of activation of nicotinic receptors.

For example, in some embodiments, the present invention provides a method and compositions for treating depression, comprising administering a combination of a compound of the present invention and one or more known antidepressants. Antidepressants useful according to the invention comprise selective serotonin reuptake inhibitors (SSRIs), tricyclics, serotonin norepinephrine reuptake inhibitors (5-HT-NE dual reuptake inhibitors), and norepinephrine and dopamine reuptake inhibitors (NDRIs).

In one embodiment, compounds or prodrugs of the present invention may be combined with one or more compounds that are serotonin reuptake inhibitors. Serotonin reuptake inhibitors increase the extracellular level of the serotonin by inhibiting its reuptake into the presynaptic cell, which increases the level of serotonin available to bind to and stimulate the postsynaptic receptor. Examples of SSRIs include fluoxetine (PROZAC®) paroxetine (PAXIL®), sertraline (ZOLOFT®), citalopram (CELEXA®), escitalopram (LEXAPRO®), nefazodone (SERZONE®) and fluvoxamine (LUVOX®).

In another embodiment, compounds of the present invention may be combined with one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination. There are two isoforms of monoamine oxidase inhibitors, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-B isoform preferentially deaminates phenylethylamine and trace amines. Dopamine is equally deaminated by both isoforms. MAOIs may by reversible or non-reversible and may be selective for a specific isoform. For example, the MAOI moclobemide (also known as Manerix or Aurorix) is known to be approximately three times more selective for MAO-A than MAO-B. Any compound generally recognized as being an MAOI may be useful according to the present invention. Non-limiting examples of MAOIs useful in combination with compounds of the present invention according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or 1-deprenyl); lazabemide; nialamide; iproniazid (marsilid, iprozid, ipronid, rivivol, or propilniazida); iproclozide; toloxatone; harmala; brofaromine (Consonar); benmoxin (Neuralex); and certain tryptamines, such as 5-MeO-DMT (5-Methoxy-N,N-dimethyltryptamine) or 5-MeO-AMT (5-methoxy-α-methyltryptamine).

According to still another embodiment of the invention, compounds of any one of the formulas disclosed herein may be combined with one or more compounds that is a norepinephrine reuptake inhibitor (NRI). NRIs are also known as noradrenaline reuptake inhibitors (NARIs) and generally function to elevate the level of norepinephrine in the central nervous system (CNS) by inhibiting reuptake of norepinephrine from the synaptic cleft into the presynaptic neuronal terminal. Norepinephrine is a catecholamine and phenylethylamine that functions as a neurotransmitter and is known to affect many conditions. Any compound typically recognized as inhibiting the reuptake of norepinephrine in the CNS can be used according to the present invention. Non-limiting examples of NRIs useful according to the invention comprise atomoxetine (STRATTERA®), reboxetine (EDRONAX®, VESTRA®, or NOREBOX®), viloxazine (EMOVIT®, VIVALAN®, VIVARINT®, or VIVILAN®), maprotiline (DEPRILEPT®, LUDIOMIL®, or PSYMION®), bupropion (WELLBUTRIN® or ZYBAN®), and radafaxine.

Further non-limiting examples of specific antidepressants useful according to the invention include tricyclics such as amitriptyline, nortriptyline, and desipramine; serotonin-norepinephrine reuptake inhibitors such as venlafaxine (EFFEXOR®), duloxetine (CYMBALTA®), and milnacipran; tetracyclics such as maprotiline and mirtazapine; and other classes of compounds, including triazolopyridines such as trazodone.

The above compounds and classes of compounds are only examples of the types of active agents that can be used in combination with a compound of the present invention for the treatment of mood disorders, sleep disorders, or attention deficit disorders and are not intended to be limiting of the invention. Rather, various further active agents can be combined with one or more compounds of the present invention according to the invention. For example, any drug generally recognized as being an antidepressant, antinarcoleptic, or ADHD treatment can be used in combination with one or more compounds of the present invention. Moreover, it is possible according to the invention to combine two or more additional active agents with a compound of the present invention for the treatment of the noted conditions.

Non-limiting examples of further active agents that can be combined with compounds of the present invention include: mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonist (5-HT2 and 5-HT3 antagonists) (such as ondansetron, tropisetron, katenserin, methysergide, cyproheptadine, and pizotifen); serotonin receptor agonists (5-HT1A receptor agonists) (such as buspirone); stimulants [such as caffeine, ADDERALL®, methylphenidate (METADATE®, RITALIN®, or CONCERTA®), pemoline (CYLERT®), or modafinil (PROVIGIL®)]; and gamma-hydroxybutyrate (GHB) (XYREM®). Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with compounds of the present invention for treating the conditions described herein.

The compounds of any of the formulas disclosed herein and the optional one or more other therapeutic agents may be contained within a single composition or alternatively may be administered concurrently or sequentially (consecutively) in any order. For sequential administration, each of the compound of the formulas disclosed herein and the one or more other therapeutic agents can be formulated in its own pharmaceutical composition, each of which is to be administered sequentially, in any order. Alternatively, the compound of the formulas disclosed herein and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for preventing, treating, or delaying the progression of disorders that are alleviated by the modulation of activation of the nAChRs of a patient, the method comprising administering a therapeutically effective amount of at least one compound of the formulas disclosed herein to the patient. In certain embodiments, administration of the compound results in the formation of one or more active metabolites.

In particular, the present invention relates to the field of treating nicotine dependence in animals, particularly humans and other mammals, and associated effects of these conditions. Dependence has its common meaning, e.g., the condition that exists when an individual persists in the use of a substance despite impairment or distress related to the use of the substance. While not wishing to be bound by theory, it is believed that by nicotine dependence may be successfully treated by blocking some of the pharmacological effects of nicotine, while also dissociating some of the reinforcing effects of nicotine. As used herein, a patient in need of treatment for nicotine dependence is a person who uses nicotine-containing products on a regular basis and is either unable or unwilling to terminate this use. In certain embodiments of the present invention, the method relates to administration of a compound disclosed herein, concurrent with or in advance of the use of nicotine. Accordingly, the patient addicted to nicotine would also be subject to the effects of the compounds while using the nicotine product, which can be beneficial in dissociating the reinforcing effects of smoking from the act of nicotine use itself.

In certain embodiments, the present invention is directed to a method of preventing nicotine dependence, by administering a compound of the present invention. A person in need of preventing nicotine dependence may be a non-user of nicotine products or an occasional user, who is concerned about the possibility of developing a dependence on nicotine products. The method of preventing nicotine dependence may be practiced by administering a compound of the present invention prophylactically, preferably in advance of the act of using a nicotine product. In this fashion, the patient will not develop a strong association of the act of smoking with the reinforcing effects of smoking. The present invention may further relate to a method of preventing nicotine dependence by administering a compound of the present invention to a person who is in the process of controlling his/her nicotine dependence in order to prevent a relapse.

In some embodiments, the invention may relate to the treatment of other conditions that may benefit from modulation of nAChR activation. For example, it may relate to treatment of Alzheimer's disease, Parkinson's disease, pain (analgesic activity), depression, Tourette's syndrome, inflammatory bowel syndrome, schizophrenia, anxiety, epilepsy, attention-deficit hyperactivity disorder, ulcerative colitis and obesity. For example, the compounds of the present invention may also be applicable to treating depression and depressive conditions in animals, particularly humans and other mammals, and associated effects of these conditions. Depression has its common meaning, e.g., a common mental disorder that presents with depressed mood, loss of interest or pleasure, feelings of guilt or low self-worth, disturbed sleep or appetite, low energy, and poor concentration or a mental state characterized by a pessimistic sense of inadequacy and a despondent lack of activity. Physical changes, such as insomnia, anorexia, weight loss, and decreased energy and libido can also occur as a result of depression. Depression includes dysthymic disorder or dysthymia, defined as a chronic low-grade depression and major depression as well as other stages or levels of depression. It also includes postpartum depression.

The method of treatment generally includes administering a therapeutically effective amount of a compound of a formula disclosed herein, optionally in a pharmaceutical composition including one or more pharmaceutically acceptable carriers. The therapeutically effective amount is preferably sufficient to interact with and cause a change in the level of activation one or more nAChRs (i.e., to cause activation of the receptor (agonist) or to deactivate the receptor (antagonist)). The therapeutically effective amount is further preferably sufficient to cause some relief to the patient in the symptoms of the disorder for which the patient is being treated.

For example, in one embodiment, a method of treating nicotine dependence is provided. In such methods, a therapeutically effective amount of a compound of the present invention to treat a patient with nicotine addiction may be that amount capable of exerting some effect on the nicotinic receptors. In another embodiment, a method of treating depression is provided. A therapeutically effective amount of a compound or prodrug of the present invention to treat a patient with depression may be that amount capable of providing some relief from symptoms such as changes in mood, feelings of intense sadness and despair, mental slowing, loss of concentration, pessimistic worry, agitation, and self-deprecation and/or from physical changes such as insomnia, anorexia and weight loss, and decreased energy and libido.

The therapeutically effective dosage amount of any specific formulation will vary somewhat from drug to drug, patient to patient, and will depend upon factors such as the condition of the patient and the route of delivery. It may further be dependent on the presence of other agonists and antagonists present in the subject's system and on the degree of binding or inhibition of binding desired. When administered conjointly with other pharmaceutically active agents, even less of the compound of the invention may be therapeutically effective. Furthermore, the therapeutically effective amount may vary depending on the specific condition to be treated. Precise amounts of active ingredient required to be administered depend on the judgment of the practitioner and are peculiar to each individual. However, suitable dosages may range from about 0.01 to about 1,000, preferably about 0.25 to about 500, and more preferably 10 to 50 milligrams of active ingredient per kilogram body weight of individual per day and depend on the route of administration. For oral administration, 1 to 100 milligrams of active ingredient per kilogram body weight of individual per day is a preferred dose. However, the exact dosage must be determined by factoring in certain variables, including but not limited to, the rate of degradation in the stomach, absorption from the stomach, and other medications administered.

Possible routes of delivery include buccally, subcutaneously, transdermally, intramuscularly, intravenously, orally, or by inhalation. The compounds of the invention can be administered once or by intermittent administration (e.g., once a day or several times a day). The daily dose can be administered either by a single dose in the form of an individual dosage unit or several smaller dosage units or by multiple administration of subdivided dosages at certain intervals. In certain embodiments, there may be an initial administration followed by repeated doses at one or more hour intervals by a subsequent injection or other administration. Alternatively, continuous intravenous infusion sufficient to maintain appropriate concentrations in the blood is contemplated.

In certain other embodiments, appropriately labeled compound represented by Formula I may be useful in a variety of other applications. For example, the labeled compounds may be used for imaging drug and neurotransmitter receptors by PET or SPECT. The labeled compounds may also be useful in ligand binding assays. Since little is known about the in vivo disposition of nAChRs both before and after chronic nicotine exposure, such labeled compounds would be very useful in the study of nAChRs. The labeled compounds of the present invention may be useful radio-labeled ligands for imaging the nicotinic receptor in vivo by PET or SPECT.

For use in imaging and tracer applications, the compounds of the present invention may be labeled with any detectable label. Accordingly, the present invention includes compounds represented by Formula I which are labeled with at least one labeling atom. Preferably, the label is a radioactive element. Examples of suitable radioactive elements include $^3$H, $^{11}$C, $^{14}$C, $^{32}$P, $^{35}$S, $^{18}$F, $^{36}$Cl, $^{51}$Cr, $^{57}$Co, $^{19}$Fe, $^{90}$Y, $^{123}$I, $^{125}$I, and $^{131}$I. Preferred radioactive elements include $^3$H, $^{11}$C, $^{18}$F, and $^{123}$I. In certain embodiments, the labeled compound may be represented by Formula I in which one or more hydrogen atom in the formula is replaced with $^3$H and/or one or more carbon atoms is replaced with $^{11}$C and/or $^{14}$C.

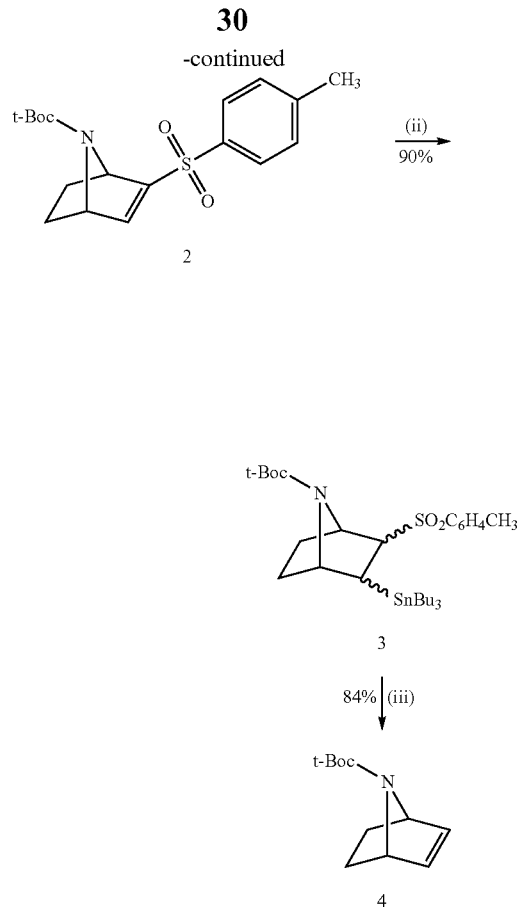

Reagents and conditions for Scheme 1: (i) Ni$_2$B, EtOH, HCl, rt, overnight; (ii) Bu$_3$SnH, AIBN, benzene, reflux; (iii) Bu$_4$NF, THF, reflux;

EXAMPLES

Example 1

Synthesis of Various Epibatidine Analogues

The synthetic route to the desired analogues commenced with preparation of the intermediate 7-tert-butoxycarbonyl-2-(p-toylsulfonyl)-7-azabicyclo[2.2.1]hepta-2,5-diene, 1, obtained via a Diels-Alder reaction between N-Boc pyrrole and p-toylsulfonylacetylene. Scheme 1 below outlines a multi-gram reaction to prepare the monoolefin 4 in 3 steps starting from 70 grams of diene 1 using a similar protocol as previously reported in earlier work (see Brieaddy, L. E. et al., *Tetrahedron Lett.* 1998, 38, 5321-5322, incorporated herein by reference).

Scheme 1.

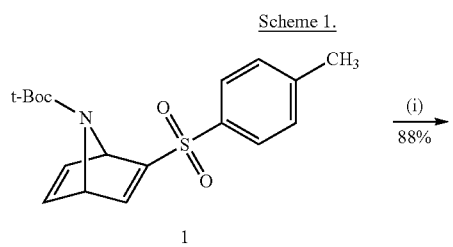

The route used in the synthesis of fumarate salts 12a-b and 13a-b is shown in Scheme 2. A Heck cross-coupling of olefin 4 with 2-amino-5-iodopyridine (5) prepared according to a reported procedure (Giantsidis, J. et al., *J. Coord. Chem.*, 2002, 55, 795-803, incorporated herein by reference), provided intermediate 6 in a 60% yield upon heating at 100° C. for 3 days under conditions previously reported (see Carroll, F. I. et al., *J. Med. Chem.*, 2001, 44, 2229-2237, incorporated herein by reference). Bromination of 6 was accomplished through the use of bromine in glacial acetic acid to provide the bromo derivative 7 in 83% yield. The bromo intermediate 7 was subjected to Suzuki cross-coupling reactions with the respective pyridinyl boronic acids in the presence of Pd(OAc)$_2$ and P(o-tolyl)$_3$ as the catalytic system, Na$_2$CO$_3$ as the base, DME as solvent, and a catalytic amount of water and was heated at 80° C. for 5 h to furnish the bipyridine derivatives 8a (see Gao, Y. et al., *J. Med. Chem.*, 2007, 50, 3814-3824, incorporated herein by reference), 8b, 9a and 9b in modest to good yields. Introduction of the fluorine and simultaneous removal of the BOC protecting group were performed through diazotization reactions using 70% HF in pyridine to furnish the free base amine derivatives 10a, 10b, 11a and 11b respectively. Finally, the fumarate salts of the respective amines were prepared and recrystallized from MeOH/ether to furnish the epibatidine analogues as fumarate salts 12a, 12b, 13a, and 13b respectively.

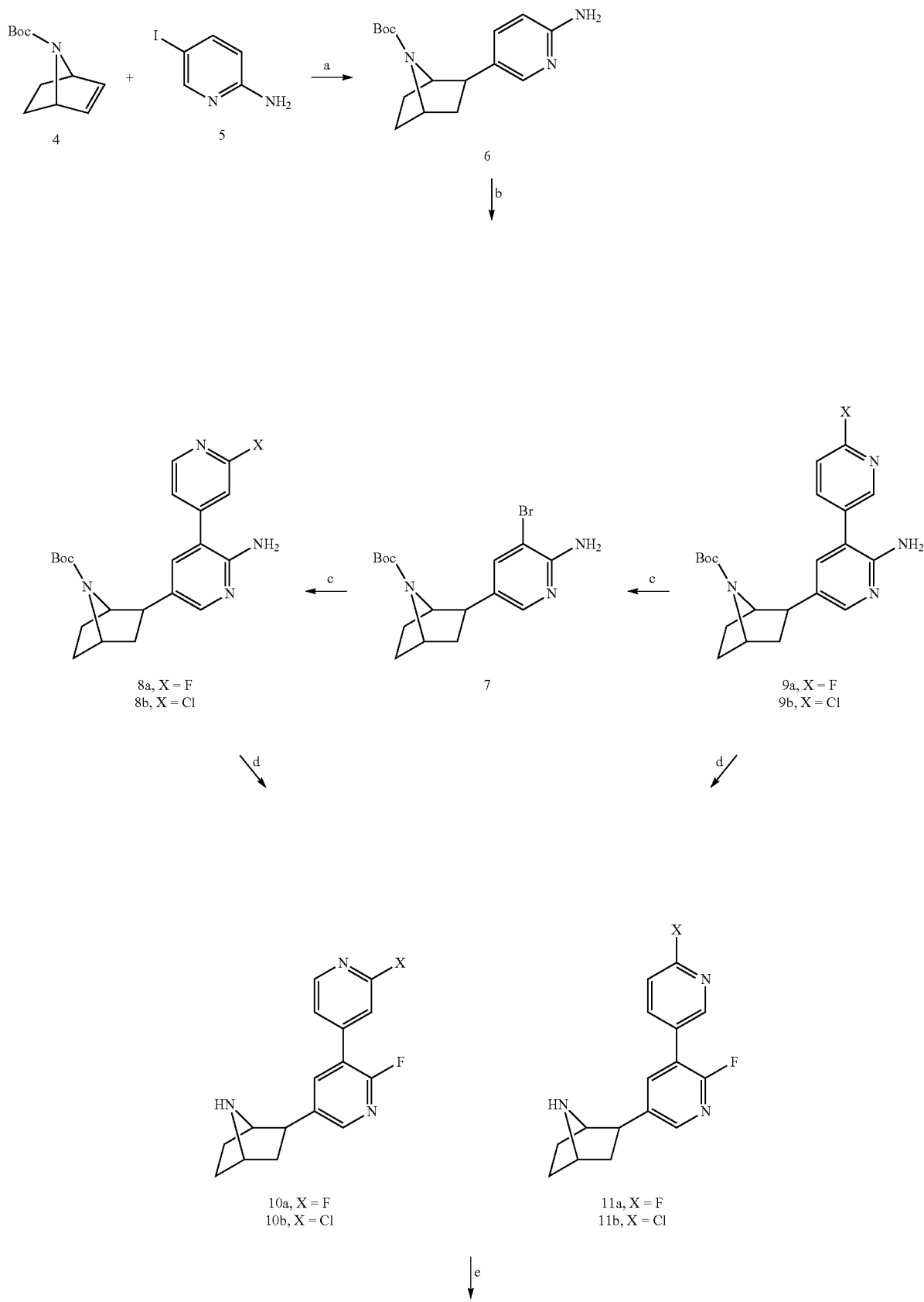
Scheme 2.

-continued

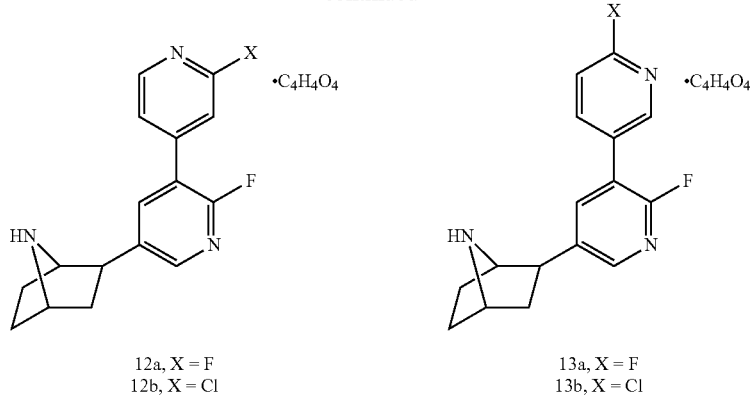

12a, X = F
12b, X = Cl

13a, X = F
13b, X = Cl

Reagents and conditions for Scheme 2: (a) Pd(OAc)₂, KO₂CH, (n-Bu)₄NCl, DMF, 100° C., 3 d, (b) Br₂, AcOH, NEt₃, CH₂Cl₂ 0° C. to rt overnight (c) Pd(OAc)₂, P(o-tolyl)₃, substituted pyridinyl boronic acid, Na₂CO₃, DME, H₂O, 80° C., 5 h (d) 70% HF-pyridine, NaNO₂ (e) Fumaric acid (1.3 equiv), MeOH/Et₂O

Experimental Procedure

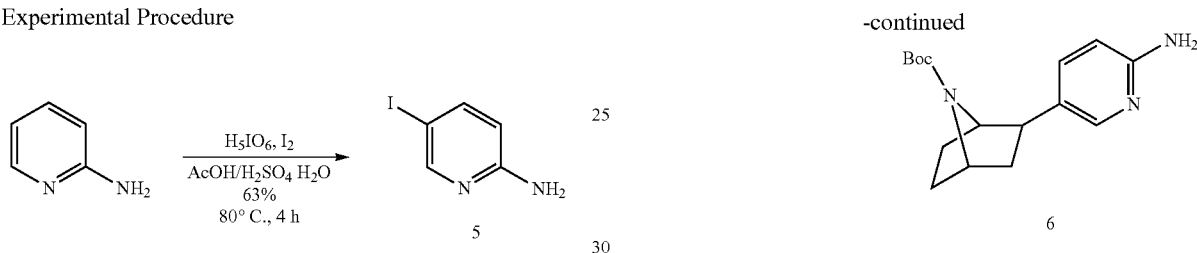

Preparation of 2-amino-5-iodopyridine (5)

To a solution of 2-aminopyridine (10.2 g, 10.8 mol) in glacial acetic acid (65 mL) and water (13 mL), was added periodic acid (4.92 g, 21.6 mol) and iodine (11.0 g, 43.2 mol). The mixture was treated with H₂SO₄ (1.9 mL) dropwise and stirred at 80° C. for 4 h. The reaction mixture was allowed to cool to room temperature and diluted with a saturated aqueous solution of sodium thiosulfate. The solution was basified with NH₄OH to pH 8-9 and extracted with ether (3×50 mL). The combined organic extracts were dried over MgSO₄, filtered, and concentrated in vacuo. The residue was purified by flash chromatography through an ISCO column (SiO₂, ethyl acetate/hexanes, 20/80 to 40/60) to give the expected 5 (15 g, 63%) as a yellow solid.

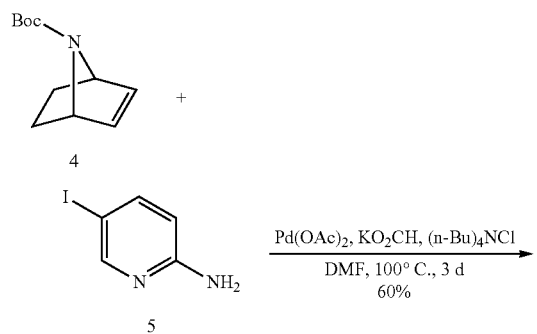

7-tert-Butoxycarbonyl-2-exo-(2'-amino-5'-pyridinyl)-7-azabicyclo[2.2.1]heptane (6)

The azabicyclo intermediate 6 was prepared through a Heck cross-coupling reaction as reported (see Carroll, F. I. et al., *J. Med. Chem.,* 2001, 44, 2229-2237, incorporated herein by reference).

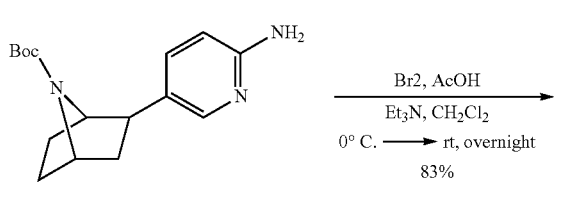

7-tert-Butoxycarbonyl-2-exo-(2'-amino-3'-bromo-5'-pyridinyl)-7-azabicyclo[2.2.1]heptane (7)

The bromination of 6 was performed using bromine in acetic acid as reported previously to provide the brominated intermediate 7 (see Carroll, F. I. et al., *J. Med. Chem.,* 2001, 44, 4039-4041, incorporated herein by reference).

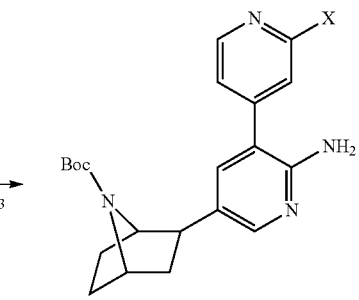
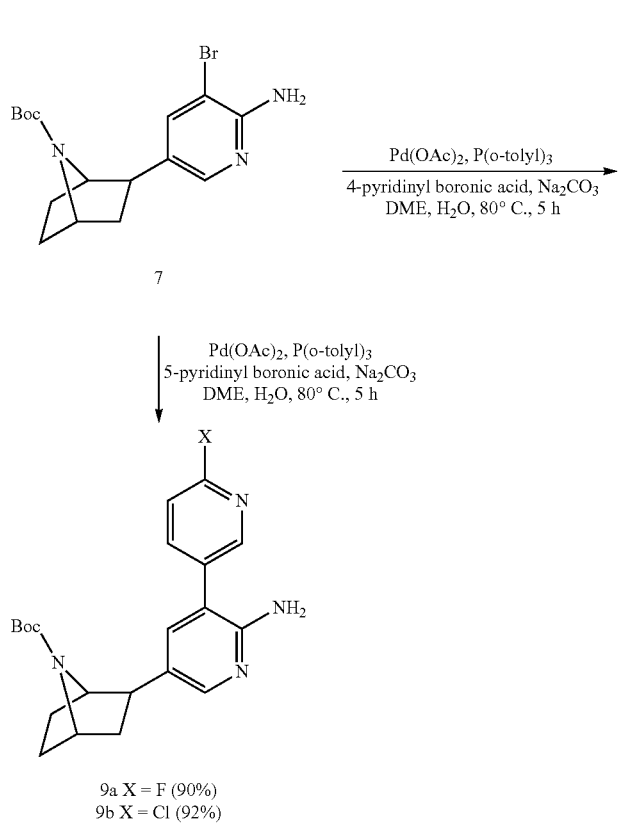

General Procedure for the Suzuki Cross-coupling Reaction (Compounds 8a, 8b, 9a and 9b).

To a resealable reaction vessel under nitrogen was added 1.0 equiv of the bromo derivative 7, Pd(OAc)$_2$ (0.1 equiv), P(o-tolyl)$_3$ (0.2 equiv), sodium carbonate (2.0 equiv) and the respective pyridinyl boronic acid (1.6 equiv), DME (6 mL) and water (0.7 mL). The mixture was degassed through bubbling nitrogen and heated at 80° C. for 5 h. The mixture was cooled, poured into 20 mL of a saturated aqueous solution of NaHCO$_3$ and extracted with EtOAc (3×30 mL). The combined organic layers were dried over MgSO$_4$, filtered through Celite and the solvent removed under reduced pressure. The resultant residue was purified by flash chromatography (CHCl$_3$/MeOH, 50/1 to 10/1).

7-tert-Butoxycarbonyl-2-exo-[2'-amino-3'-(2-fluoropyridin-4-yl)-5'-pyridinyl]-7-azabicyclo[2.2.1]heptane (8a)

The reagents were compound 7 and 2-fluoropyridine-4-boronic acid. $^1$H NMR (300 MHz, CDCl$_3$) δ 1.4 (br s, 9H), 1.52-1.59 (m, 2H), 1.82-1.84 (m, 3H), 1.94-1.98 (m, 1H), 2.79-2.84 (m, 1H), 4.16 (s, 1H), 4.36 (br s, 1H), 4.77 (s, 2 NH), 7.06 (s, 1H), 7.34 (ddd, J=1.6, 5.13, 8.4 Hz, 1H), 7.41 (d, J=2.3 Hz, 1H), 8.0 (d, J=2.3 Hz, 1H), 8.26 (d, J=5.16 Hz, 1H); MS (ESI) m/z 385.3 (M+H)$^+$.

7-tert-Butoxycarbonyl-2-exo-[2'-amino-3'-(2-chloropyridin-4-yl)-5'-pyridinyl]-7-azabicyclo[2.2.1]heptane (8b)

The reagents were compound 7 and 2-chloropyridine-4-boronic acid. $^1$H NMR (300 MHz, CDCl$_3$) δ 1.41 (br s, 9H), 1.49-1.61 (m, 2H), 1.77-1.83 (m, 3H), 1.94-2.00 (m, 1H), 2.78-2.83 (m, 1H), 4.16 (s, 1H), 4.36 (br s, 1H), 4.54 (s, 2 NH), 7.37 (dd, J=1.4, 5.13 Hz, 1H), 7.40 (d, J=2.22 Hz, 1H), 7.45 (s, 1H), 8.0 (d, J=2.22 Hz, 1H), 8.44 (d, J=5.10 Hz, 1H); $^{13}$C NMR (CDCl$_3$) δ 28.3 (3C), 28.8, 29.7, 40.5, 44.8, 55.9, 62.1, 79.6, 117.4, 122.0, 123.8, 132.4, 136.5, 147.8, 149.6, 150.2, 152.4, 153.8, 154.9; MS (ESI) m/z 401.3 (M+H)$^+$.

7-tert-Butoxycarbonyl-2-exo-[2'-amino-3'-(6-fluoropyridin-3-yl)-5'-pyridinyl]-7-azabicyclo[2.2.1]heptane (9a)

The reagents were compound 7 and 5-fluoropyridine-4-boronic acid. $^1$H NMR (300 MHz, CDCl$_3$) δ 1.39 (br s, 9H), 1.51-1.59 (m, 2H), 1.81-1.85 (m, 3H), 1.94-2.00 (m, 1H), 2.79-2.84 (m, 1H), 4.16 (s, 1H), 4.35 (br s, 1H), 4.70 (s, 2 NH), 7.02 (dd, J=2.9, 8.4 Hz, 1H), 7.34 (d, J=2.25 Hz, 1H), 7.91 (ddd, J=2.5, 8.4, 16 Hz, 1H), 7.96 (d, J=2.25 Hz, 1H), 8.28 (d, J=2.4 Hz, 1H); $^{13}$C NMR (CDCl$_3$) δ 28.2 (3C), 28.8, 29.7, 40.3, 44.8, 55.9, 62.1, 79.5, 109.5, 116.8, 132.0, 136.9, 141.5, 146.8, 147.5, 154.6, 154.9, 161.3, 164.5; MS (ESI) m/z 385.5 (M+H)$^+$.

7-tert-Butoxycarbonyl-2-exo-[2'-amino-3'-(6-chloropyridin-3-yl)-5'-pyridinyl]-7-azabicyclo[2.2.1]heptane (9b)

The reagents were compound 7 and 5-chloropyridine-4-boronic acid. $^1$H NMR (300 MHz, CDCl$_3$) δ 1.31 (br s, 9H), 1.43-1.50 (m, 2H), 1.72-1.76 (m, 3H), 1.85-1.92 (m, 1H), 2.70-2.74 (m, 1H), 4.06 (s, 1H), 4.26 (br s, 1H), 4.60 (s, 2 NH), 7.25 (d, J=2.25 Hz, 1H), 7.30 (d, J=8.2 Hz, 1H), 7.71

(dd, J=2.5, 8.2 1H), 7.88 (d, J=2.2 Hz, 1H), 8.38 (d, J=2.2 Hz, 1H); $^{13}$C NMR (CDCl$_3$) δ 28.3 (3C), 28.8, 29.7, 40.3, 44.8, 55.9, 62.1, 79.5, 116.7, 124.2, 132.2, 133.1, 136.9, 139.0, 147.0, 149.5, 150.6, 154.4, 155.0; MS (ESI) m/z 401.5 (M+H)$^+$.

General Procedure for Diazotization and Simultaneous Removal of the Boc Protecting Group (Compounds 10a, 10b, 11a and 11b).

A solution of the respective amino derivative (8a, 8b, 9a or 9b) in 70% HF-pyridine (1.5 mL) in a plastic reaction vessel was stirred at 0° C. for 30 min Sodium nitrite (10 equiv) was then added in small portions and the mixture stirred at room temperature for 1 h. The mixture was then poured into a solution of 1:1 NH$_4$OH/H$_2$O (40 mL) and extracted with EtOAc. The combined organic layers were dried over MgSO$_4$, filtered through Celite and concentrated in vacuo. The residue was purified by flash chromatography using CHCl$_3$/MeOH (10:1).

2-exo-[2'-Fluoro-3'-(2-fluoropyridin-4-yl)-5'-pyridinyl]-7-azabicyclo[2.2.1]heptane (10a)

Obtained in a 70% yield as a colorless oil. $^1$H NMR (300 MHz, CDCl$_3$) δ 1.56-1.68 (m, 6H), 1.92-1.98 (dd, J=9.1, 11.2 Hz, 1H), 2.81-2.86 (m, 1H), 3.60 (s, 1H), 3.83 (br s 1H), 7.17 (d, J=1.0 Hz, 1H), 7.43 (ddd, J=1.6, 4.9, 6.9 Hz, 1H), 8.15-8.19 (m, 2H), 8.23 (d, J=5.3 Hz, 1H); $^{13}$C NMR (CDCl$_3$) δ 30.4, 31.5, 40.7, 44.2, 56.4, 62.9, 109.0, 119.4, 121.1, 139.6, 141.5, 147.5, 157.1, 160.3, 162.6, 162.7; MS (ESI) m/z 288.3 (M+H)$^+$.

2-exo-[2'-Fluoro-3'-(2-chloropyridin-4-yl)-5'-pyridinyl]-7-azabicyclo[2.2.1]heptane (10b)

Obtained in an 87% yield as a colorless oil. $^1$H NMR (300 MHz, CDCl$_3$) δ 1.54-1.67 (m, 6H), 1.92-1.98 (dd, J=9.1, 11.2 Hz, 1H), 2.81-2.86 (m, 1H), 3.60 (s, 1H), 3.83 (br s 1H), 7.46 (dd, J=1.2, 5.2 Hz, 1H), 7.56 (s, 1H), 8.12-8.15 (m, 2H), 8.47 (d, J=5.2 Hz, 1H); $^{13}$C NMR (CDCl$_3$) δ 30.4, 31.5, 40.7, 44.3, 56.4, 62.9, 119.4, 122.1, 139.6, 141.5, 145.1, 147.2, 149.9, 152.1, 157.1, 160.3; MS (ESI) m/z 304.3 (M+H)$^+$.

2-exo-[2'-Fluoro-3'-(6-fluoropyridin-3-yl)-5'-pyridinyl]-7-azabicyclo[2.2.1]heptane (11a)

Obtained in a 66% yield as a colorless oil. $^1$H NMR (300 MHz, CDCl$_3$) δ 1.54-1.70 (m, 6H), 1.92-1.99 (dd, J=9.0, 11.2 Hz, 1H), 2.82-2.87 (m, 1H), 3.61 (s, 1H), 3.83 (br s 1H), 7.04 (dd, J=3.0, 8.4 Hz, 1H), 7.99-8.09 (m, 2H), 8.14 (br s, 1H), 8.42 (d, J=0.8 Hz, 1H); $^{13}$C NMR (CDCl$_3$) δ 30.4, 31.5, 40.6, 44.3, 56.4, 62.9, 109.3, 118.5, 139.5, 141.3, 145.8, 147.5, 157.3, 160.4, 161.7, 164.9; MS (ESI) m/z 288.3 (M+H)$^+$.

2-exo-[2'-Fluoro-3'-(6-chloropyridin-3-yl)-5'-pyridinyl]-7-azabicyclo[2.2.1]heptane (11b)

Obtained in a 62% yield as a colorless oil. $^1$H NMR (300 MHz, CDCl$_3$) δ 1.54-1.71 (m, 6H), 1.92-1.98 (dd, J=9.1, 11.2 Hz, 1H), 2.81-2.86 (m, 1H), 3.61 (s, 1H), 3.81 (br s 1H), 7.42 (dd, J=0.6, 8.3 Hz, 1H), 7.88 (ddd, J=0.8, 4.1, 8.3 Hz, 1H), 8.06 (dd, J=2.4, 9.6 Hz, 1H), 8.15 (br s, 1H), 8.58 (br s, 1H); $^{13}$C NMR (CDCl$_3$) δ 30.4, 31.5, 40.6, 44.3, 56.4, 62.9, 118.5, 124.1, 129.2, 139.5, 141.3, 146.1, 149.2, 151.2, 157.3, 160.5; MS (ESI) m/z 304.3 (M+H)$^+$.

General Procedure for Fumarate Salt Formation (Analogues 12a, 12b, 13a and 13b).

A solution of the respective amine (10a, 10b, 11a or 11b) in ether (3 mL) in a vial was treated with a 1.3 equiv of fumaric acid (0.65 M) in MeOH and allowed to stand in a refrigerator overnight. The excess ether was then removed under reduced pressure and the residue salt was redissolved in a minimal amount of MeOH. The fumarate salts were recrystallized from MeOH using diethyl ether.

2'-Fluoro-3'-(2"-fluoro-4"-pyridinyl)deschloroepibatidine fumarate (12a)

Obtained in a 55% yield as a white crystalline solid after recrystallization: mp. 203-205° C.; $^1$H NMR (500 MHz, CD$_3$OD) δ 1.87-2.20 (m, 5H), 2.45-2.50 (dd, J=9.3, 13.2 Hz, 1H), 3.50-3.53 (m, 1H), 4.34-4.35 (br s, 1H), 4.56 (d, J=3.9 Hz, 1H), 6.64 (s, 2H), 7.41 (s, 1H), 7.61-7.63 (m, 1H), 8.21 (dd, J=2.4, 9.3 Hz, 1H), 8.28 (d, J=1.0 Hz, 1H), 8.32 (d, J=5.3 Hz, 1H); $^{13}$C NMR (CD$_3$OD) δ 25.8, 27.8, 36.5, 42.2, 59.0, 62.8, 109.4, 121.6, 135.0, 136.5, 140.1, 147.2, 147.8, 158.3, 160.2, 163.4, 165.3, 170.2; MS (ESI) m/z 288.3 [(M-fumaric)$^+$, M=C$_{16}$H$_{15}$F$_2$N$_3$·C$_4$H$_4$O$_4$]; Anal. (C$_{20}$H$_{19}$F$_2$N$_3$O$_4$) C, H, N.

2'-Fluoro-3'-(2"-chloro-4"-pyridinyl)deschloroepibatidine fumarate (12b)

Obtained in a 42% yield as a white crystalline solid after recrystallization: mp. 193-194° C.; $^1$H NMR (500 MHz, CD$_3$OD) δ 1.87-2.21 (m, 5H), 2.45-2.50 (dd, J=9.2, 13.2 Hz, 1H), 3.50-3.53 (m, 1H), 4.34-4.35 (br s, 1H), 4.56 (d, J=3.9 Hz, 1H), 6.63 (s, 2H), 7.67 (dd, J=1.4, 9.3 Hz, 1H), 7.80 (s, 1H), 8.21 (dd, J=2.4, 9.3 Hz, 1H), 8.28 (d, J=2.4 Hz, 1H), 8.48 (d, J=4.9 Hz, 1H); $^{13}$C NMR (CD$_3$OD) δ 25.7, 27.8, 36.5, 42.2, 59.0, 62.9, 119.4, 122.7, 135.0, 136.6, 140.1, 145.4, 147.3, 149.9, 151.8, 158.3, 160.3, 170.1; MS (ESI) m/z 304.0 [(M-fumaric)$^+$, M=C$_{16}$H$_{15}$ClFN$_3$·C$_4$H$_4$O$_4$]; Anal. (C$_{20}$H$_{19}$ClFN$_3$O$_4$·0.25H$_2$O)C, H, N.

2'-Fluoro-3'-(2"-fluoro-5"-pyridinyl)deschloroepibatidine hemifumarate (13a)

Obtained in a 33% yield as a white crystalline solid after recrystallization: mp. 197-199° C.; $^1$H NMR (500 MHz, CD$_3$OD) δ 1.81-2.15 (m, 5H), 2.38-2.43 (dd, J=9.3, 13.2 Hz, 1H), 3.42-3.46 (m, 1H), 4.43 (br s, 1H), 6.57 (s, 1H), 7.21 (dd, J=2.4, 8.3 Hz 1H), 8.14 (dd, J=2.4, 8.2 Hz, 1H), 8.21-8.25 (m, 2H), 8.48 (br s, 1H); $^{13}$C NMR (CD$_3$OD) δ 27.5, 29.5, 38.3, 43.8, 59.9, 64.1, 111.0, 120.5, 129.6, 137.0, 138.4, 141.4, 143.8, 147.2, 148.8, 159.7, 161.6, 164.1, 166.0, 174.0; MS (ESI) m/z 288.3 [(M-fumaric)$^+$, M=C$_{16}$H$_{15}$F$_2$N$_3$·0.5C$_4$H$_4$O$_4$]; Anal. (C$_{18}$H$_{17}$F$_2$N$_3$O$_2$) C, H, N.

2'-Fluoro-3'-(2"-chloro-5"-pyridinyl)deschloroepibatidine fumarate (13b)

Obtained in a 55% yield as a white crystalline solid after recrystallization: mp. 194-195° C.; $^1$H NMR (500 MHz, CD$_3$OD) δ 1.89-2.20 (m, 5H), 2.45-2.49 (dd, J=9.2, 13.2 Hz, 1H), 3.49-3.52 (dd, J=3.5, 9.5 Hz, 1H), 4.34 (br s, 1H), 4.56 (d, J=3.5 Hz, 1H), 6.63 (s, 2H), 7.60 (d, J=8.5 Hz, 1H), 8.09-8.15 (m, 2H), 8.23 (d, J=2.4 Hz, 1H), 8.64 (br s, 1H); $^{13}$C NMR (CD$_3$OD) δ 27.1, 29.1, 37.8, 43.5, 60.3, 64.2, 120.4, 125.8, 130.6, 136.3, 137.8, 141.3, 147.4, 150.6, 152.6, 159.8, 161.7, 171.5; MS (ESI) m/z 304.5 [(M-fumaric)$^+$, M=C$_{16}$H$_{15}$ClFN$_3$·C$_4$H$_4$O$_4$]; Anal. (C$_{20}$H$_{19}$ClFN$_3$O$_4$) C, H, N.

Example 2

Synthesis of 2'-(Pyridinyl and Methoxypyridinyl Substituted) Epibatidine Analogues These exemplary procedures relate to the synthesis of fumarate salts of analogues, containing pyridinyl ring substitution and 2-methoxy pyridinyl ring substitution. The brominated intermediate, 7, (7-tert-butoxycarbonyl-2-exo-(2'-amino-3'-bromo-5'-pyridinyl)-7-azabicyclo[2.2.1]heptane) was prepared as previously described in Example 1 and the references therein. Scheme 3 outlines the route to the analogues discussed in this example. Suzuki cross-coupling reactions of bromo intermediate 7 with the respective pyridinyl boronic acids, in the presence of Pd(PPh$_3$)$_4$ as the catalyst, K$_2$CO$_3$ as the base and toluene (15 mL), ethanol (1.5 mL) and water (1.5 mL) as solvents, heated at reflux for 24 h in a sealed tube provided the cross-coupled products (14a, 14b, 15a, 15b and 16) in good yields. Diazotization reactions using 70% HF in pyridine successfully converted the amine to a fluoro group with simultaneous removal of the BOC group in the case of the pyridinyl and 2-methoxypyridinyl analogues furnishing the free base amine derivatives (17a, 17b, 18a, 18b, and 19), in good yields. The fumarate salts of the respective amines were prepared and recrystallized from MeOH/ ether to furnish the epibatidine analogues as fumarate salts 20a, 20b and 21 respectively.

Scheme 3.

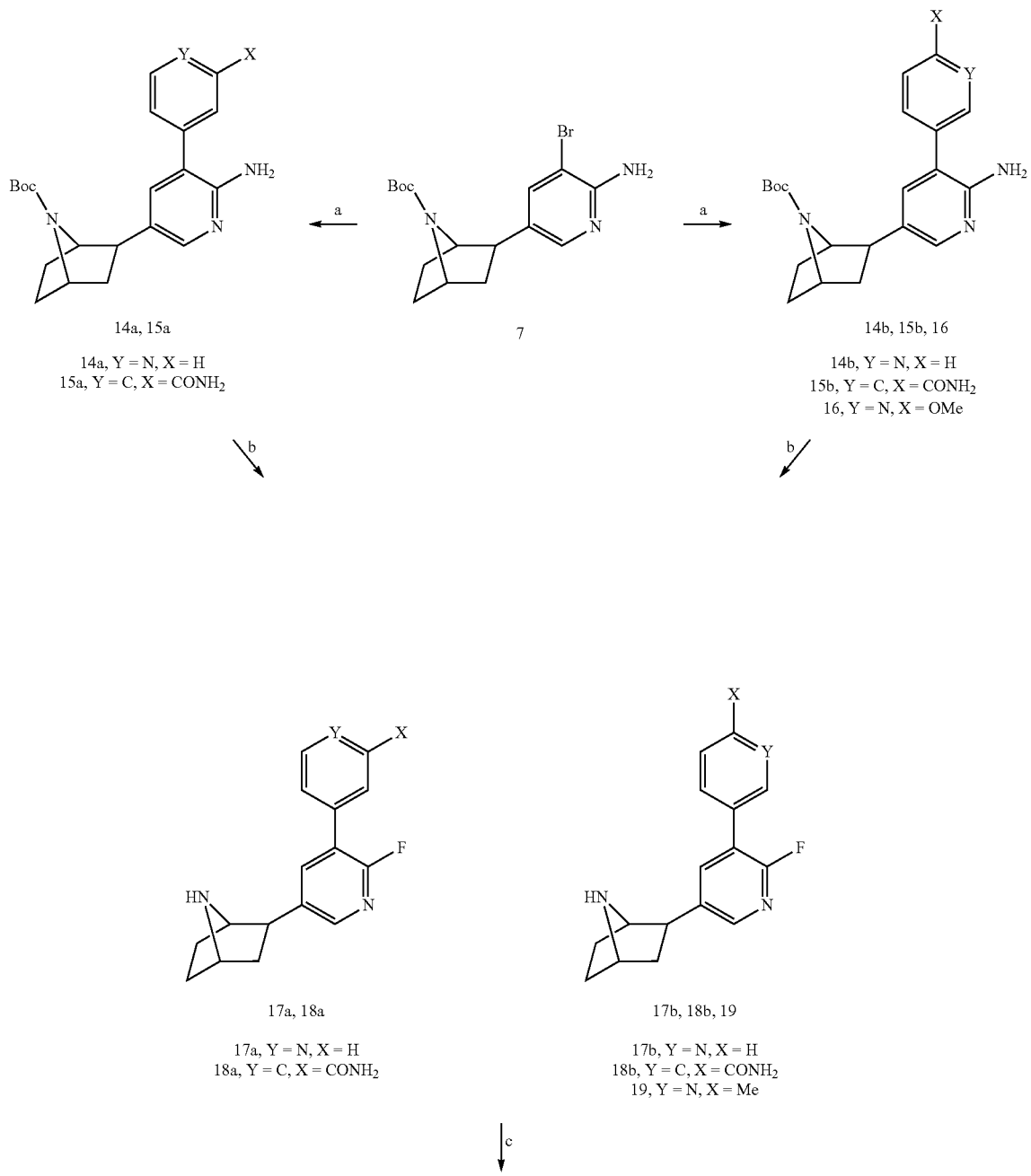

-continued

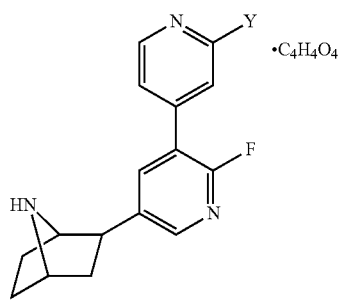

20a

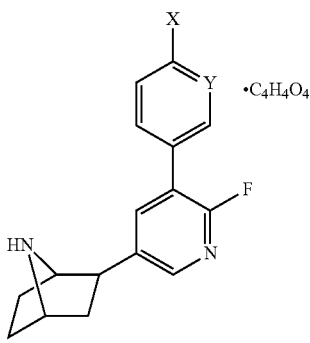

20b, 21

20a, 20b, Y = N, X = H
21, Y = N, X = OMe

Reagents and conditions for Scheme 3: (a) Pd(PPh3)4, RB(OH)2, K2CO3, toluene, EtOH, H2O, reflux, 24 h (b) 70% HF-pyridine, NaNO2 (c) Fumaric acid (1.1 equiv), MeOH/Et2O Experimental Procedure

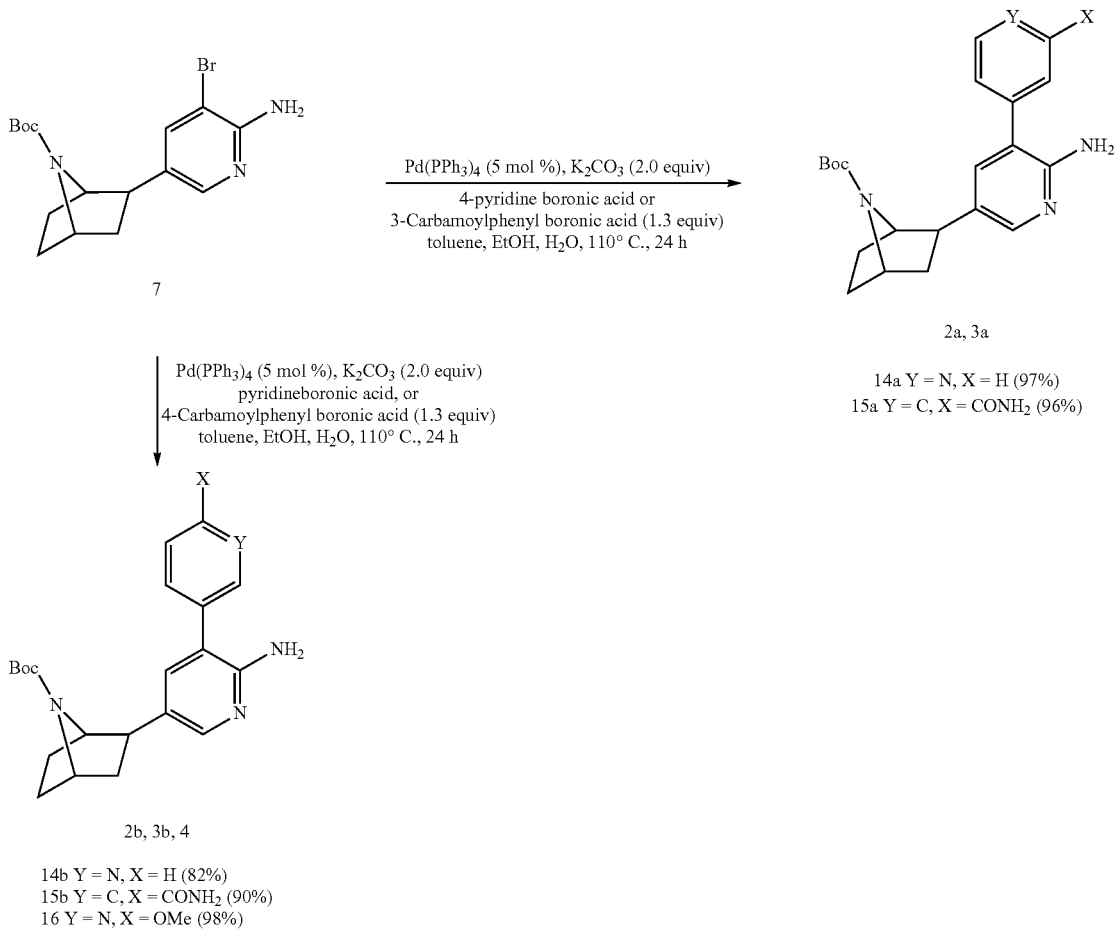

14a Y = N, X = H (97%)
15a Y = C, X = CONH2 (96%)

14b Y = N, X = H (82%)
15b Y = C, X = CONH2 (90%)
16 Y = N, X = OMe (98%)

General Procedure for the Synthesis of 14a, 14b, 15a, 15b and 16.

To a resealable reaction vessel under nitrogen was added 1.0 equiv of 7, Pd(PPh3)4, K2CO3 (2.0 equiv) and the respective boronic acid (1.3 equiv), toluene (12 mL), ethanol (1.5 mL) and water (1.5 mL). The mixture was degassed through bubbling nitrogen and heated at 110° C. After 24 h, the mixture was cooled, poured into 30 mL of H2O and extracted with EtOAc (3×30 mL). The combined organic layers were dried over MgSO4, filtered through Celite and the solvent was

7-tert-Butoxycarbonyl-2-exo-[2'-amino-3'-(pyridin-4-yl)-5'-pyridinyl]-7-azabicyclo[2.2.1]heptane (14a)

The reagents were compound 7 and pyridine-4-boronic acid. $^1$H NMR (300 MHz, CDCl$_3$) δ 1.39 (br s, 9H), 1.44-1.59 (m, 2H), 1.81-1.84 (m, 3H), 1.93-2.00 (m, 1H), 2.79-2.84 (dd, J=3.8, 5.0 Hz, 1H), 4.16 (s, 1H), 4.36 (br s, 1H), 4.67 (s, 2 NH), 7.39-7.43 (m, 3H), 7.99 (d, J=2.3 Hz, 1H), 8.66 (dd, J=6.0, 1.5 Hz, 1H); $^{13}$C NMR (CDCl$_3$) 6; 28.3 (3C), 40.4, 44.8, 55.8, 62.1, 79.5, 118.7, 123.4, 132.2, 136.5, 146.4, 147.2, 150.5, 153.9, 154.9; MS (ESI) m/z 367.6 (M+H)$^+$.

7-tert-Butoxycarbonyl-2-exo-[2'-amino-3'-(pyridin-3-yl)-5'-pyridinyl]azabicyclo[2.2.1]heptane (14b)

The reagents were compound 7 and pyridine-3-boronic acid. $^1$H NMR (300 MHz, CDCl$_3$) δ 1.41 (br s, 9H), 1.48-1.61 (m, 2H), 1.75-1.86 (m, 3H), 1.96-2.04 (m, 1H), 2.79-2.83 (dd, J=3.8, 5.0 Hz, 1H), 4.16 (s, 1H), 4.35 (br s, 1H), 4.66 (s, 2 NH), 7.34 (d, J=2.5 Hz, 1H), 7.38 (d, J=4.9 Hz, 1H), 7.80 (dt, J=7.9, 1.9 Hz, 1H), 7.96 (d, J=2.2 Hz, 1H), 8.59 (dd, J=4.9, 1.6 Hz, 1H), 8.69 (d, J=1.8 Hz, 1H); $^{13}$C NMR (CDCl$_3$) δ 28.3 (3C), 28.8, 29.7, 40.3, 44.9, 55.9, 62.2, 79.5, 118.0, 123.6, 132.1, 134.1, 136.2, 136.9, 146.6, 148.9, 149.7, 154.5, 154.9; MS (ESI) m/z 367.6 (M+H)$^+$.

7-tert-Butoxycarbonyl-2-exo-[2'-amino-3'-(3-aminocarbonylphenyl)-5'-pyridinyl]-7-azabicyclo[2.2.1]heptane (15a)

The reagents were compound 7 and 3-carbamoylphenyboronic acid. $^1$H NMR (300 MHz, CD$_3$OD) δ 1.37 (br s, 9H), 1.49-1.59 (m, 2H), 1.74-1.88 (m, 3H), 1.90-1.97 (m, 1H), 2.91-2.96 (dd, J=4.0, 4.7 Hz, 1H), 4.16 (s, 1H), 4.33 (br s, 1H), 7.40 (d, J=2.3, Hz, 1H), 7.56 (t, J=7.6 Hz, 1H), 7.65 (dt, J=7.8, 1.5 Hz, 1H), 7.86 (d, J=2.2 Hz, 1H), 7.91 (dt, J=7.6, 1.6 Hz, 1H), 7.96 (t, J=1.5 Hz 1H); $^{13}$C NMR (CD$_3$OD) δ 28.6 (3C), 29.8, 30.5, 40.9, 45.9, 57.2, 63.6, 66.9, 81.2, 122.8, 128.4, 129.1, 130.4, 132.7, 133.2, 136.0, 138.8, 139.8, 145.9, 156.2, 156.4, 172.0; MS (ESI) m/z 409.6 (M+H)$^+$.

7-tert-Butoxycarbonyl-2-exo-[2'-amino-3'-(4-aminocarbonylphenyl)-5'-pyridinyl]-7-azabicyclo[2.2.1]heptane (15b)

The reagents were compound 7 and 4-carbamoylphenylboronic acid. $^1$H NMR (300 MHz, CDCl$_3$) δ 1.38 (br s, 9H), 1.51-1.58 (m, 2H), 1.81-1.86 (m, 3H), 1.93-2.03 (m, 1H), 2.78-2.83 (dd, J=3.8, 4.9 Hz, 1H), 4.11 (s, 1H), 4.35 (br s, 1H), 4.6 (s, 2NH), 6.32-6.44 (br s, H, 2H), 7.37 (d, J=2.3, Hz, 1H), 7.53 (dt, J=8.4, 1.9 Hz, 2H), 7.92 (td, J=8.4, 1.7 Hz, 2H), 7.95 (d, J=2.3 Hz, 1H); $^{13}$C NMR (CDCl$_3$) δ 28.4 (3C), 29.0, 29.9, 40.4, 45.1, 56.0, 60.5, 62.3, 79.7, 120.6, 128.3, 129.0, 132.1, 132.9, 136.8, 142.1, 146.3, 154.4, 155.1, 169.3; MS (ESI) m/z 409.6 (M+H)$^+$.

7-tert-Butoxycarbonyl-2-exo-[2'-amino-3'-(6-methoxypyridin-3-yl)-5'-pyridinyl]-7-azabicyclo[2.2.1] heptane (16)

The reagents were compound 7 and 2-methoxy-5-pyridineboronic acid. $^1$H NMR (300 MHz, CDCl$_3$) δ 1.39 (br s, 9H), 1.50-1.59 (m, 2H), 1.76-1.88 (m, 3H), 1.91-1.98 (m, 1H), 2.77-2.81 (dd, J=3.7, 5.0 Hz, 1H), 3.94 (s, 3H), 4.16 (s, 1H), 4.34 (br s, 1H), 4.78 (s, 2 NH), 6.79 (d, J=8.5 Hz, 1H), 7.30 (d, J=2.3 Hz, 1H), 7.65 (dd, J=8.4, 2.4 Hz, 1H), 7.93 (d, J=2.3 Hz, 1H) 8.22 (d, J=2.3 Hz, 1H); $^{13}$C NMR (CDCl$_3$) δ 28.1 (3C), 28.4, 28.6, 40.1, 44.8, 53.3, 55.3, 62.1, 79.3, 110.8, 118.1, 126.9, 128.4, 131.8, 136.7, 138.9, 145.8, 146.6, 154.8, 163.5; MS (ESI) m/z 397.5 (M+H)$^+$.

General Procedure for Diazotization and Simultaneous Removal of the Boc Protecting Group (Compounds 17a, 17b, 18a, 18b and 19).

A solution of the respective amino derivative (14a, 14b, 15a, 15b or 16) in 70% HF-pyridine (1.5 mL) in a plastic reaction vessel was stirred at 0° C. for 30 min. Sodium nitrite (10 equiv) was then added in small portions and the mixture stirred at room temperature. After 1 h, the mixture was poured into a 1:1 aqueous solution of NH$_4$OH/H$_2$O (40 mL) and extracted with EtOAc (3×40 mL). The combined organic layers were dried over MgSO$_4$, filtered through Celite and concentrated in vacuo. The resultant residue was purified by flash chromatography using CHCl$_3$/MeOH (10:1).

2-exo-[2'-Fluoro-3'-(pyridin-4-yl)-5'-pyridinyl]-7-azabicyclo[2.2.1]heptane (17a)

Obtained in a 69% yield as a colorless oil. $^1$H NMR (300 MHz, CD$_3$OD) δ 1.50-1.78 (m, 6H), 2.01-2.08 (dd, J=9.0, 11.2 Hz, 1H), 3.02-3.07 (dd, J=8.7, 5.2 Hz, 1H), 3.66 (s, 1H), 3.77 (br 1H), 7.70-7.73 (m, 2H), 8.13 (dd, J=2.4, 9.4 Hz, 1H), 8.18 (s, 1H), 8.64 (d, J=1.5 Hz, 1H), 8.65 (d, J=1.5 Hz, 1H); $^{13}$C NMR (CD$_3$OD) δ 30.0, 31.8, 41.1, 45.7, 57.9, 63.7, 121.2, 125.1, 141.3, 142.1, 144.2, 147.8, 148.0, 150.6, 158.6, 161.7; MS (ESI) m/z 270.2 (M+H)$^+$.

2-exo-[2'-Fluoro-3'-(pyridin-3-yl)-5'-pyridinyl]-7-azabicyclo[2.2.1]heptane (17b)

Obtained in 70% yield as a colorless oil. $^1$H NMR (300 MHz, CD$_3$OD) δ 1.49-1.79 (m, 6H), 2.01-2.08 (dd, J=9.1, 11.2 Hz, 1H), 3.02-3.07 (dd, J=3.3, 5.4 Hz, 1H), 3.67 (s, 1H), 3.77 (br s 1H), 7.54 (dd, J=2.6, 7.8 Hz, 1H), 8.08-8.15 (m, 3H), 8.58-8.60 (d, 2H), 8.58 (d, J=1.4 Hz, 1H), 8.80 (s, 1H); $^{13}$C NMR (CD$_3$OD) δ 29.9, 31.8, 40.6, 41.1, 45.7, 57.8, 63.9, 121.1, 125.2, 138.4, 141.4, 142.0, 147.0, 149.9, 150.1, 158.7, 161.8; MS (ESI) m/z 270.3 (M+H)$^+$.

2-exo-[2'-Fluoro-3'-(6-methoxypyridin-3-yl)-5'-pyridinyl]-7-azabicyclo[2.2.1]heptane (19)

Obtained in a 73% yield as a colorless oil. $^1$H NMR (300 MHz, CD$_3$OD) δ 1.48-1.76 (m, 6H), 1.94-2.05 (m, 2H), 2.96-3.01 (dd, J=3.4, 5.5 Hz, 1H), 3.65 (s, 1H), 3.77 (br s 1H), 6.83 (d, J=8.7 Hz, 1H), 7.88 (tt, J=0.7, 1.7, 8.7 Hz, 1H), 7.99 (dd, J=2.4, 9.6 Hz, 1H), 8.04 (d, J=0.8 Hz, 1H), 8.34 (d, J=1.6 Hz, 1H); $^{13}$C NMR (CD$_3$OD) δ 29.9, 31.7, 40.9, 45.7, 54.3, 57.7, 63.7, 111.7, 121.3, 124.5, 140.8, 141.6, 145.8, 147.9, 158.6, 161.8, 165.5; MS (ESI) m/z 300.3 (M+H)$^+$.

Example 3

Synthesis of Epibatidine Analogs—Pyridinyl, Methoxy Pyridinyl and Carbamoyl Phenyl Substituted Analogs Heck cross-coupling of monoolefin 4 with 2-amino-5-iodopyridine, 5, was done as reported in earlier examples to provide intermediate 6 which was subsequently subjected to bromination at the C-3 position ortho to the amino group to provide 7 (7-tert-butoxycarbonyl-2-exo-(2'-amino-3'-bromo-5'-pyridinyl)-7-azabicyclo[2.2.1]heptane). For the synthesis of the pyridinyl and methoxy pyridinyl analogs, 7 was subjected to the Suzuki cross-coupling reactions with the respective pyridinyl boronic acids in the presence of Pd(PPh$_3$)$_4$ as the catalyst, K$_2$CO$_3$ as the base and toluene (15 mL), ethanol (1.5 mL) and water (1.5 mL) as solvents as shown in the Scheme 4 below. The reactions were heated at reflux for 24 h in a sealed tube to provide the cross-coupled products in good yields. Diazotization reactions using 70% HF in pyridine successfully converted the amino to a fluoro group with simultaneous removal of the BOC group. The fumarate salts of the respective amines were prepared and recrystallized from MeOH/ether to furnish the epibatidine analogs as fumarate salts 20a, 20b and 21 respectively as discussed in Example 2 above.

In the case of carbamoyl phenyl analogs, the brominated intermediate 7, was first subjected to a diazonium reaction converting the amino group to a Fluoro group along with the simultaneous removal of the t-Boc group to provide the amine intermediate. The Suzuki cross-coupling of the amine intermediate with the respective carbamoyl phenyl boronic acids provided the amine analogs 18a and 18b. Hydrochloride salts of the amines were prepared to provide analogs 22a and 22b.

Scheme 4.

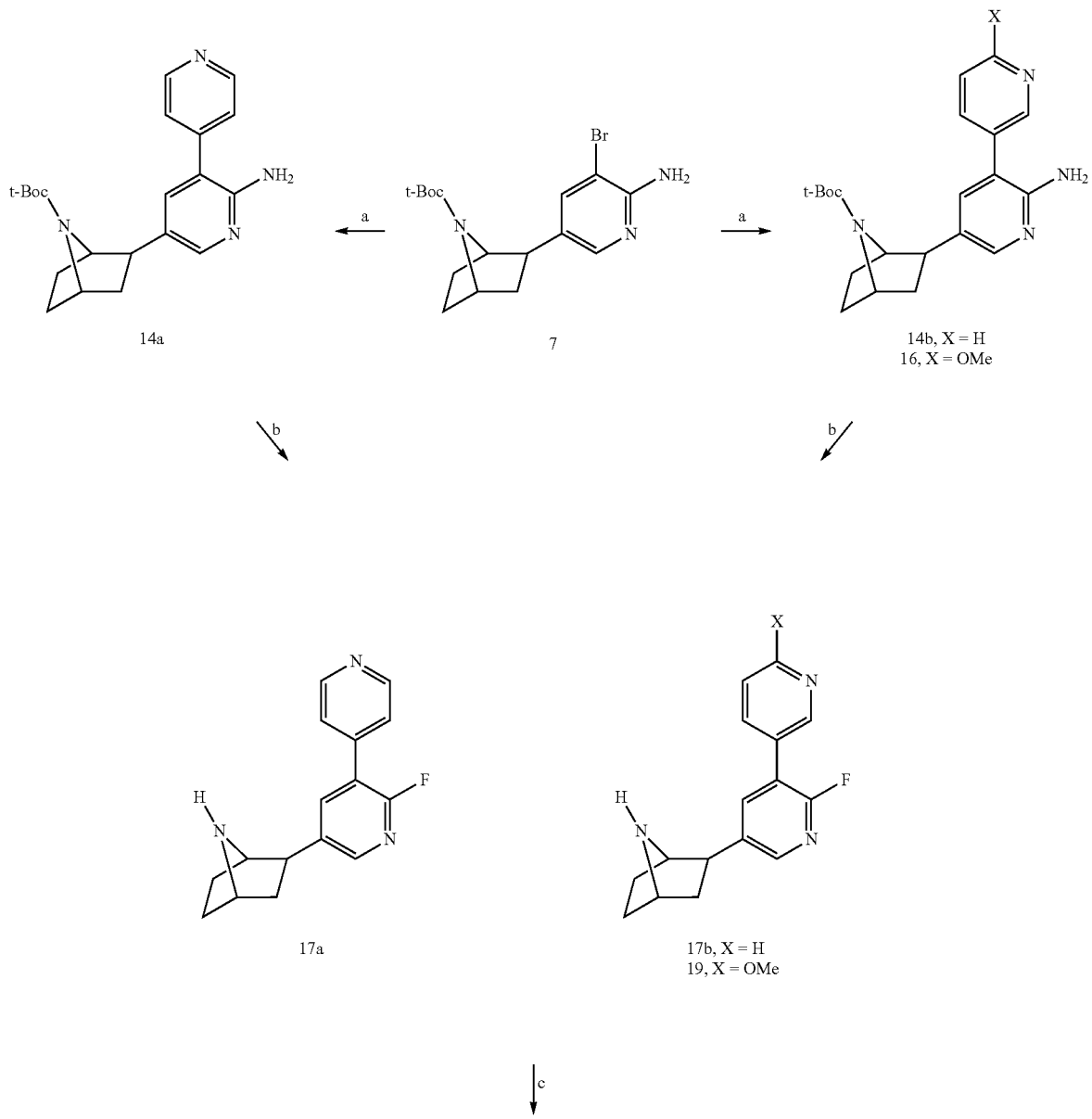

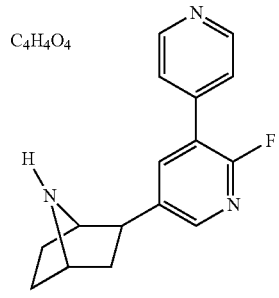

20a

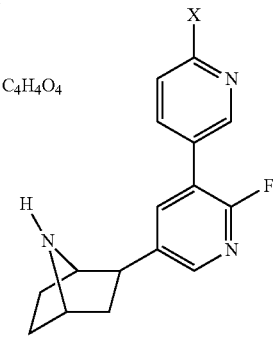

20b, X = H
21, X = OMe

Reagents and conditions for Scheme 4: (a) Pd(PPh₃)₄, Boronic acid, K₂CO₃, toluene, EtOH, H₂O, reflux, 24 h (b) 70% HF-pyridine, NaNO₂ (c) Fumaric acid (1.1 equiv), MeOH/Et₂O Experimental Procedure:

General Procedure for Fumarate Salt Formation (Analogues 20a, 20b and 21).

A solution of the respective amine (17a, 17b, or 19) in methanol (1 mL) in a vial was treated with a 1.1 equiv of fumaric acid (0.65 M) in MeOH and left standing overnight in a refrigerator. Excess ether was removed under reduced pressure and the resultant salt was redissolved in minimal amount of MeOH. The fumarate salts were recrystallized from MeOH using diethyl ether.

2'-Fluoro-3'-(4"-pyridinyl)deschloroepibatidine fumarate (20a)

Mp. 192-195° C. $^1$H NMR (300 MHz, CD$_3$OD) δ 1.86-2.22 (m, 6H), 2.44-2.51 (dd, J=9.0, 11.0 Hz, 1H), 3.50-3.55 (m, 1H), 4.35 (br s, 1H), 4.56 (d, J=3.9 Hz, 1H), 6.63 (s, 1H), 7.72-7.75 (m, 2H), 8.20 (dd, J=2.4, 9.0 Hz, 1H), 8.27 (d, J=2.4 Hz, 1H), 8.67 (m, 2H); $^{13}$C NMR (CD$_3$OD) δ 27.0, 29.0, 37.7, 43.4, 60.2, 64.1, 121.6, 125.1, 136.2, 137.6, 141.3, 147.8, 148.0, 150.7, 159.0, 162.2, 171.4; MS (ESI) m/z 270.1 [(M-fumaric)$^+$, M=C$_{16}$H$_{16}$FN$_3$·C$_4$H$_4$O$_4$]; Anal. (C$_{20}$H$_{20}$FN$_3$O$_4$·0.25H$_2$O) C, H, N.

2'-Fluoro-3'-(3"-pyridinyl)deschloroepibatidine hemifumarate (20b)

Mp. 155-159° C. $^1$H NMR (300 MHz, CD$_3$OD) δ 1.86-2.22 (m, 6H), 2.44-2.51 (dd, J=9.0, 11.0 Hz, 1H), 3.49-3.54 (dd, J=3.0, 5.1 Hz, 1H), 4.35 (br s, 1H), 4.56 (d, J=3.9 Hz, 1H), 6.63 (s, 1H), 7.56-7.60 (dd, J=2.3, 7.5 Hz, 1H), 8.12-8.16 (m, 2H), 8.23 (s, 1H), 8.61 (dd, J=1.4, 6.0 Hz, 1H), 8.81 (s, 1H); $^{13}$C NMR (CD$_3$OD) δ 27.4, 29.4, 38.2, 43.8, 59.8, 64.0, 121.0, 125.4, 136.8, 138.2, 138.5, 141.4, 147.0, 147.2, 150.0, 159.1, 162.3, 171.5; MS (ESI) m/z 270.2 [(M-fumaric)$^+$, M=C$_{16}$H$_{16}$FN$_3$·0.5C$_4$H$_4$O$_4$]; Anal. (C$_{18}$H$_{18}$FN$_3$O$_2$·0.5H$_2$O) C, H, N.

2'-Fluoro-3'-(2"-methoxy-5"-pyridinyl)deschloroepibatidine hemifumarate (21)

Mp. 193-195° C. $^1$H NMR (300 MHz, CD$_3$OD) δ 1.80-2.15 (m, 6H), 2.36-2.43 (dd, J=9.3, 13.2 Hz, 1H), 3.40-3.45 (m, 1H), 3.96 (s, 3H), 4.27 (br s, 1H), 4.42 (s, 1H), 6.61 (s, 1H), 6.91 (dd, J=0.7, 7.6 Hz 1H), 7.95 (dt, J=0.8, 2.4, 8.8 Hz, 1H), 8.06 (dd, J=1.9, 8.8 Hz, 1H), 8.14 (d, J=1.9 Hz, 1H), 8.41 (br s, 1H); $^{13}$C NMR (CD$_3$OD) δ 27.4, 29.4, 38.3, 43.8, 54.3, 59.8, 64.0, 111.7, 124.2, 136.8, 138.1, 140.76, 145.8, 148.0, 159.1, 162.2, 165.7, 176.3; MS (ESI) m/z 300.5 [(M-fumaric)$^+$, M=C$_{17}$H$_{18}$FN$_3$O·0.5C$_4$H$_4$O$_4$]; Anal. (C$_{19}$H$_{20}$FN$_3$O$_3$·0.25H$_2$O) C, H, N.

2-exo-[2'-Fluoro-3'-(4-aminocarbonylphenyl)-5'-pyridinyl]-7-azabicyclo[2.2.1]heptane (18a)

Obtained in a 78% yield as a colorless oil.

$^1$H NMR (300 MHz, CDCl$_3$) δ 1.53-1.72 (m, 5H), 1.91-1.98 (m, 3H), 2.82-2.86 (m, 1H), 3.61 (s, 1H), 3.80 (s, 1H), 6.58 (br s, 2H), 7.62-7.65 (m, 2H), 7.89-7.92 (m, 2H), 8.01 (dd, J=2.4, 9.6 Hz, 1H), 8.10 (s, 1H); $^{13}$C NMR (CDCl$_3$) δ 30.2, 40.5, 44.4, 56.4, 62.8, 122.2, 127.1, 129.0, 133.1, 137.8, 139.8, 140.8, 145.6, 160.5, 169.1; MS (ESI) m/z 312.6 (M+H)$^+$.

2-exo-[2-Fluoro-3'-(3-aminocarbonylphenyl)-5'-pyridinyl]-7-azabicyclo[2.2.1]heptane (18b)

Obtained in a 79% yield as a colorless oil.

$^1$H NMR (300 MHz, CD$_3$OD) δ 1.46-1.74 (m, 5H), 1.99-2.03 (m, 1H), 2.95-3.00 (m, 1H), 3.62 (s, 1H), 3.74 (s, 1H), 7.54 (t, J=7.8 Hz 1H), 7.77 (dt, J=1.2, 7.8 Hz, 1H), 7.91 (dt, J=1.1, 7.8 Hz, 1H), 8.01 (dd, J=2.3, 9.6 Hz, 1H), 8.06 (s, 1H), 8.11 (s, 1H); $^{13}$C NMR (CD$_3$OD) δ 29.9, 31.8, 41.1, 45.7, 57.8, 63.7, 123.6, 128.7, 129.2, 130.0, 133.3, 132.9, 135.6, 141.4, 146.3, 158.6, 161.8, 171.7; MS (ESI) m/z 312.6 (M+H)$^+$.

General Procedure for the Hydrochloride Salts Formation of the Benzamide Analogs 22a and 22b A solution of the amine benzamides (18a or 18b) in chloroform in a vial was treated with a 1.0 equivalent of HCl in diethyl ether. The excess solvent was removed in vacuo and the salt dried under vacuum.

2-exo-2-Fluoro-3-(4'-benzamide)deschloroepibatidine Hydrochloride (22a)

Obtained as a white solid in 99% yield. M.p 202-206° C. $^1$H NMR (300 MHz, CD$_3$OD) δ 1.91-2.20 (m, 5H), 2.46-2.54 (dd, J=3.8, 9.6 Hz, 1H), 3.51-3.56 (m, 1H), 4.35, (d, J=3.5 Hz, 1H), 4.60 (d, J=2.5 Hz, 1H), 7.77-7.74 (m, 2H), 7.99-8.02 (m, 2H), 8.10 (dd, J=2.4, 9.2 Hz, 1H), 8.20 (s, 1H); $^{13}$C NMR (CD$_3$OD) δ 26.8, 28.9, 37.6, 43.3, 60.5, 64.3, 123.8, 129.1, 130.2, 135.0, 137.2, 138.3, 141.4, 146.4, 159.1, 162.3, 171.6; MS (ESI) m/z 312.4 [(M−HCl)$^+$, M=C$_{18}$H$_{18}$FN$_3$O.HCl]; Anal. (C$_{18}$H$_{19}$ClFN$_3$O.1.75H$_2$O) C, H, N.

2-exo-2-Fluoro-3-(3'-benzamide)deschloroepibatidine Hydrochloride (22b)

Obtained in a 99% yield as a white solid. $^1$H NMR (300 MHz, CD$_3$OD) δ 1.99-2.24 (m, 5H), 2.45-2.53 (dd, J=3.8, 9.6 Hz, 1H), 3.51-3.56 (m, 1H), 4.36, (d, J=3.5 Hz, 1H), 4.60 (d, J=2.5 Hz, 1H), 7.59 (t, J=7.8 Hz 1H), 7.83 (dt, J=1.2, 7.8 Hz, 1H), 7.95 (dt, J=1.2, 7.8 Hz, 1H), 8.13-8.20 (m, 3H); $^{13}$C NMR (CD$_3$OD) δ 26.8, 28.9, 37.6, 43.3, 60.5, 64.3, 124.4, 128.8, 129.4, 130.0, 133.4, 135.4, 137.2, 141.4, 146.4, 159.1, 162.3, 171.7; MS (ESI) m/z 312.5 [(M−HCl)$^+$, M=C$_{18}$H$_{18}$FN$_3$O.HCl]. Anal. (C$_{18}$H$_{19}$ClFN$_3$O.2.5H$_2$O) C, H, N.

Example 4

Synthesis of Epibatidine Analogues—Pyridinyl, Methoxy Pyridinyl, and Amino Pyridinyl Substituted Analogues In the exemplary procedures discussed in this example, the brominated intermediate 7, was first subjected to a diazonium/Sandmeyer reaction using HF in pyridine to convert the amino group to a Fluoro group along with the simultaneous removal of the t-Boc group to provide the intermediate 23. The synthesis of the amino pyridinyl analogue was achieved via a Miyaura cross-coupling reaction between intermediate 23 and the commercially available 2-amino pyridine-5-pinacol boronic ester, 24 (Scheme 5). The cross-coupling was accomplished using Pd(PPh$_3$)$_4$ as a catalyst, K$_2$CO$_3$ as the base, dioxane as the solvent with catalytic amounts of water and heated at 110° C. in a sealed tube overnight to provide the diamine 25 in a 67% yield. The diamine 25 was converted into the HCl salt 26 using HCl in diethyl ether.

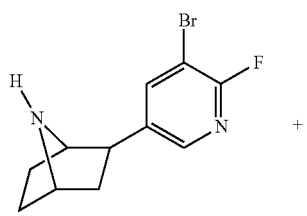

23

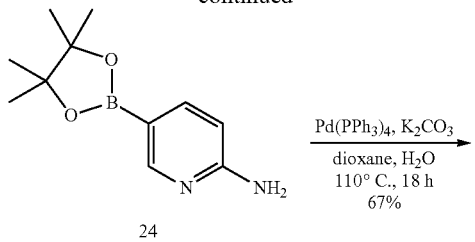

24

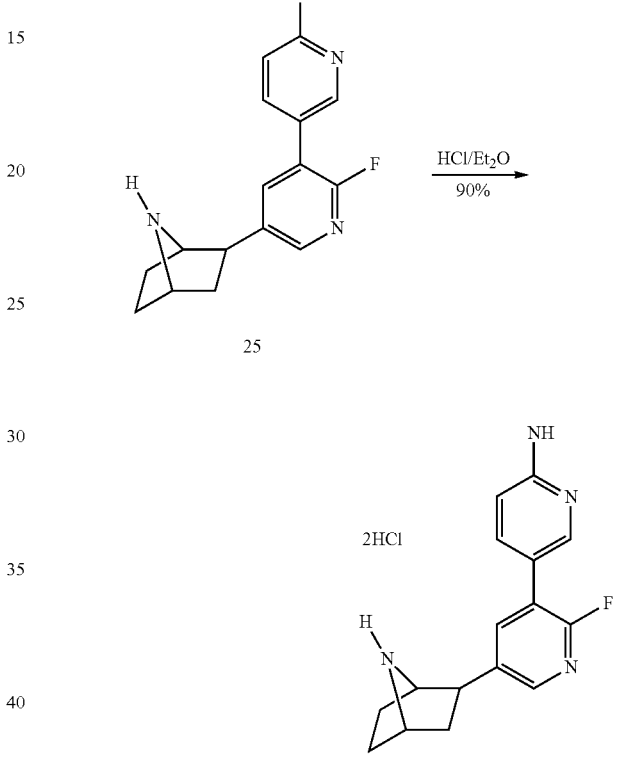

There are two possible routes for the preparation of 2-methoxypyridine-4-pinacol boronic ester, 32, a known compound, as shown in Schemes 6 (see Fraley, M. E. et al., Bioorg. Med. Chem. Lett. 2002, 12, 3537-3541, incorporated herein by reference) and 7 (see Morgentin, R. et al., Tetrahedron, 2008, 64, 2772-2780, incorporated herein by reference). The alternate route for the synthesis of 4-amino-2-methoxypyridine, 30, (Scheme 7) was sought due to the low yields obtained in the nitration step of Scheme 6. Cross-coupling of 34 with bis(pinacolata)diborane in the presence of potassium acetate as the base and PdCl$_2$(dppf) as the catalyst and heated in DMF at 80° C. overnight provided the boronic ester 32 in a 74% yield.

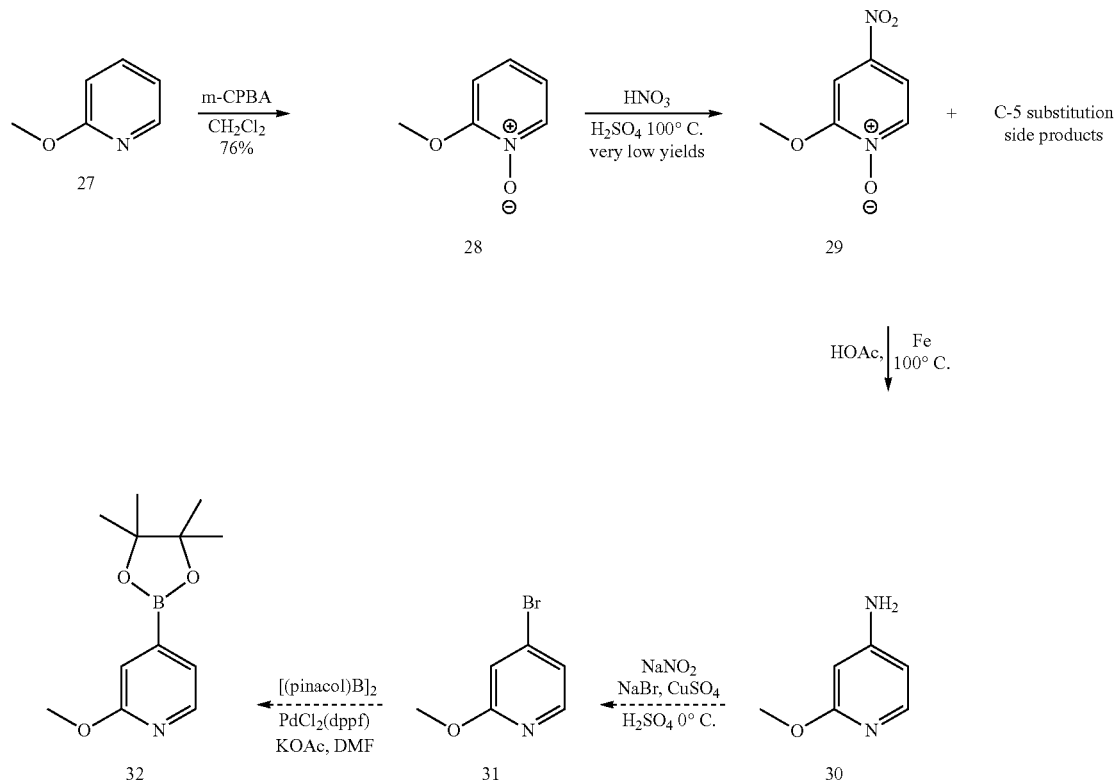
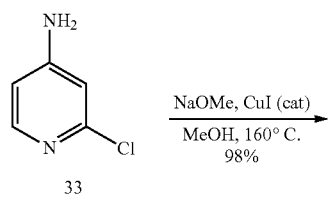
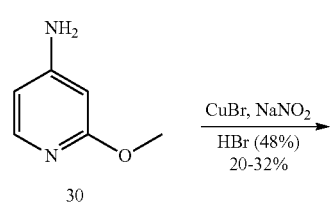
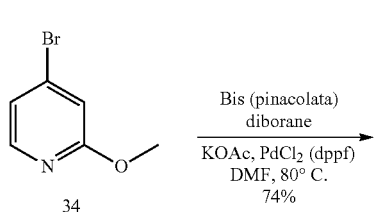
The methoxy substituted analogue 35 was obtained from the cross-coupling of 23 and the boronic ester 32 (Scheme 8 below) in a 50% yield. The amine analogue 35 was converted to the fumarate salt 36, using fumaric acid in MeOH and recrystallized using diethylether.
Scheme 8.
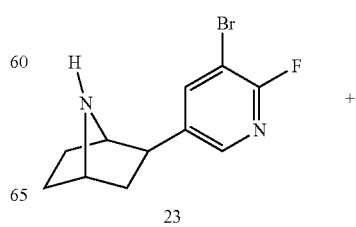

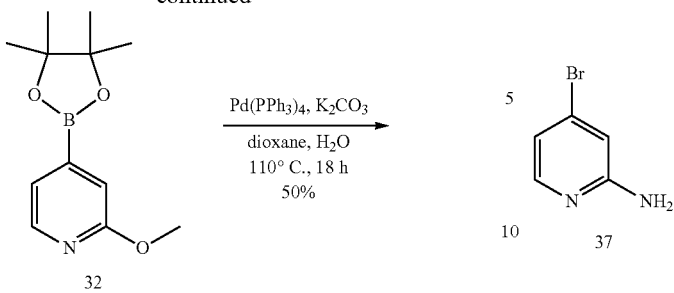

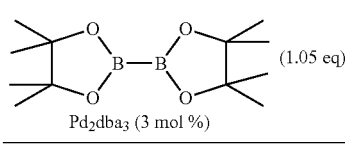

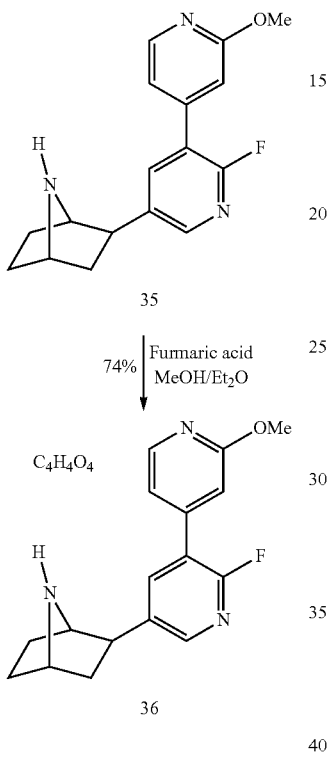

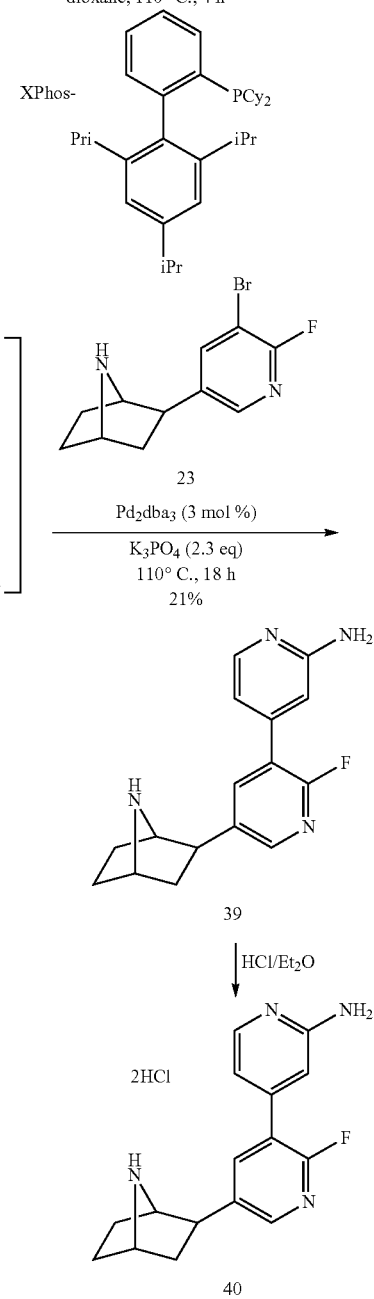

Several different conditions for the synthesis of 38 were investigated and the successful synthesis involved a "one-pot" reaction protocol that combined the borylation and the Suzuki-Miyaura using Buchwald's ligand, Xphos (2-Dicyclohexylphosphino-2',4',6'-triisopropylbiphenyl) (see Billingsley, K. L. et al., *Angew. Chem. Int. Ed.*, 2007, 46, 5359-5363; Martin, T. et al., *Org. Lett.*, 2009, 11, 3690-3693, both incorporated herein by reference). Following a protocol similar to the cited reference, the borylation reaction was accomplished by cross-coupling of commercially available 2-amino-4-bromopryidine (37) and bis(pinacolata)diborane, XPhos, and $Pd_2 dba_3$ as catalyst. The reaction was heated at 110° C. in dioxanes in the presence of 3.0 equivalents of KOAc and monitored by TLC and until all the starting material was converted to the boronic ester after 4 hours. The boronic ester was carried on to the next step directly by addition of 23, $K_3PO_4$ as base and an additional 3 mol % of $Pd_2 dba_3$. The reaction was heated at 110° C. for an additional 18 h to provide the desired product 39 in 21% yield (Scheme 9). The amine was converted to the hydrochloride salt using HCl in diethylether to furnish 40 in a quantitative yield.

Experimental Procedures:
Procedure for Diazotization/Sandmeyer Reactions and Simultaneous Removal of the Boc Protecting Group (Compound 23).

A solution of the respective amino derivative 7, in 70% HF-pyridine (1.5-3 mL) in a plastic reaction vessel was stirred at 0° C. for 30 min. Sodium nitrite (10 equiv) was then added in small portions and the mixture stirred at room temperature for 1 h. The mixture was then poured into a solution of 1:1 NH₄OH/H₂O (60 mL) and extracted with CHCl₃. The combined organic layers were dried over MgSO₄, filtered through Celite and concentrated in vacuo. The residue was purified by flash chromatography using CHCl₃/MeOH (10:1).

2-exo-[2'-Fluoro-3'-bromo-5'-pyridinyl]-7-azabicyclo[2.2.1]heptane, (23)

Obtained in a 90% yield as a colorless oil. ¹H NMR (300 MHz, CD₃OD) δ 1.47-1.68 (m, 6H), 1.96-2.03 (m, 2H), 2.92-2.96 (dd, J=3.4, 5.5 Hz, 1H), 3.59 (s, 1H), 3.75 (br s 1H), 8.06 (d, J=2.4 Hz, 1H), 8.17 (dd, J=2.4, 8.8 Hz, 1H); ¹³C NMR (CD₃OD) δ 30.1, 31.8, 41.2, 45.5, 57.8, 63.6 105.0, 143.2, 145.9, 147.9, 157.9, 161.0; MS (ESI) m/z 271.2, 273.3 (M+H)⁺.

Procedures for the Synthesis of Amino and Methoxy Substituted Compounds 25 and 35 and their Fumarate Salts 26 and 36.

To a resealable reaction pressure vessel under nitrogen was added 1.0 equiv of 2-exo-(2'-amino-3'-bromo)-7-azabicyclo[2.2.1]heptane, Pd(PPh₃)₄ (5 mol %), K₂CO₃ (2.0 equiv), dioxane (10 mL), water (0.80 mL), and the respective boronic ester (1.3 equiv). The mixture was degassed through bubbling nitrogen for 40 min and heated at 110° C. for 18 h. After cooling, the solvent was removed under reduced pressure and to the residue was added 20 mL of H₂O. The organic product was extracted using EtOAc (3×30 mL). The combined organic layers were dried over MgSO₄, filtered through Celite and the solvent removed in vacuo. Purification by flash chromatography using MeOH/ CHCl₃ provided the desired products 25 and 35 as colorless oils in yields of 67% and 50% respectively.

2'-Fluoro-3'-(2"-amino-5"-pyridinyl)deschloroepibatidine (25)

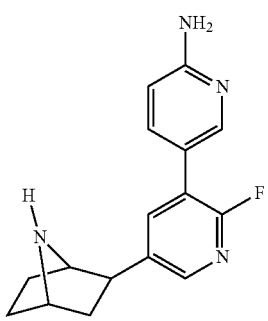

¹H NMR (300 MHz, CDCl₃) δ 1.47-1.67 (m, 5H), 1.85-1.92 (m, 2H), 2.76-2.80 (dd, J=3.8, 5.0 Hz, 1H), 3.56 (s, 1H), 3.75 (d, J=2.7 Hz, 1H), 4.82 (s, 2H), 6.53 (d, J=8.6 Hz, 1H), 7.63 (dt, J=1.9, 8.6 Hz, 1H), 7.87 (dd, J=2.3, 9.5 Hz, 1H), 7.98 (s, 1H), 8.23 (s, 1H); ¹³CNMR (CDCl₃) δ 30.2, 31.4, 40.5, 44.5, 56.4, 62.8, 108.2, 120.2, 138.0, 138.7, 140.7, 144.2, 147.9, 157.5, 158.3, 160.6; MS (ESI) m/z 285.7 (M+H)⁺.

2'-Fluoro-3'-(2"-amino-5"-pyridinyl)deschloroepibatidine hydrochloride (26)

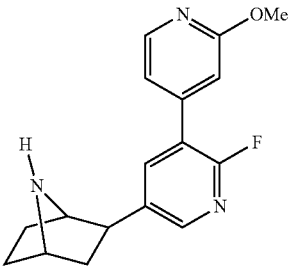

A solution of the diamine 25 in chloroform in a vial was treated with a 2.0 equivalents solution of HCl in diethyl ether and allowed to stand at room temperature. The excess solvent was filtered off and the obtained salt washed with ether and then dried to provide a 90% yield of the salt as a white solid. Mp. 202-205° C. ¹H NMR (300 MHz, CD₃OD) δ 1.88-2.24 (m, 5H), 2.44-2.52 (dd, J=3.8, 9.6 Hz, 1H), 3.51-3.56 (dd, J=3.1, 5.5 Hz, 1H), 4.37 (d, J=3.4 Hz, 1H), 4.58 (d, J=2.7 Hz, 1H), 7.11 (dd, J=1.9, 8.2 Hz, 1H), 8.18-8.28 (m 4H); ¹³CNMR (CD₃OD) δ 26.8, 28.9, 37.6, 43.3, 60.5, 64.4, 114.7, 119.3, 120.4, 137.6, 140.6, 145.1, 147.2, 155.8, 158.9, 162.1; MS (ESI) m/z 285.6 [(M−HCl)⁺, M=C₁₆H₁₇FN₄.2HCl]; Anal. (C₁₆H₁₉Cl₂FN₄.1.25H₂O) C, H, N.

2-exo-[2'-Fluoro-3'-(2-methoxypyridin-4-yl)-5'-pyridinyl]-7-azabicyclo[2.2.1]heptane (35)

¹H NMR (300 MHz, CDCl₃) δ 1.51-1.68 (m, 5H), 1.89-1.96 (dd, 3.8, 9.6 Hz, 1H), 1.98 (broad signal 1H), 2.79-2.84 (dd, J=3.4, 5.5 Hz, 1H), 3.59 (s, 1H), 3.81 (s, 1H), 3.96 (s, 3 H), 6.96 (s, 1H), 7.07-7.10 (dt, J=5.3, 1.5 Hz, 1H), 8.06 (dd, J=2.4, 9.6 Hz, 1H), 8.11 (s, 1H), 8.21 (d, J=5.3 Hz, 1H); ¹³C NMR (CDCl₃) δ 30.2. 31.4, 40.5, 44.3, 53.5, 56.4, 62.9, 110.5, 116.6, 139.6, 140.8, 144.6, 146.2, 146.4, 147.2, 160.5, 164.6; MS (ESI) m/z (300.4) (M+H)⁴.

2-Fluoro-3-(2'-methoxy-4'-pyridinyl)deschloroepibatidine fumarate (36)

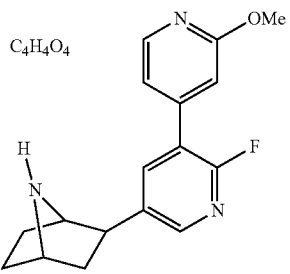

A solution of 35 in CH$_2$Cl$_2$ in a vial was treated with a 1.2 equiv of fumaric acid (0.65 M) in MeOH and the vial was allowed to stand in a refrigerator overnight. The excess solvent was then removed in vacuo from the salt and then redissolved in minimal amount of MeOH and the fumarates salt was recrystallized from MeOH using diethyl ether. Mp. 160-164° C. $^1$H NMR (300 MHz, CD$_3$OD) δ 1.85-2.19 (m, 5H), 2.43-2.50 (dd, J=9.3, 13.2 Hz, 1H), 3.48-3.53 (m, 1H), 3.96 (s, 3H), 4.34 (br s, 1H), 4.55 (s, 1H), 6.65 (s, 2H), 7.07 (s, 1H), 7.22 (dd, J=1.2, 4.1 Hz 1H), 8.12 (d, J=9.2 Hz, 1H), 8.22-8.23 (m 2H); $^{13}$C NMR (CD$_3$OD) δ 26.9, 29.0, 37.7, 43.4, 54.2, 60.2, 64.1, 111.6, 117.9, 136.1, 137.5, 141.2, 147.5, 147.6, 148.3, 166.2, 171.1; MS (ESI) m/z 300.3 [(M-fumaric)$^+$, M=C$_{17}$H$_{18}$FN$_3$O.C$_4$H$_4$O$_4$]; Anal. (C$_{21}$H$_{22}$FN$_3$O$_5$) C, H, N.

2-Fluoro-3-(2'-amino-4'-pyridinyl)deschloroepibatidine (39)

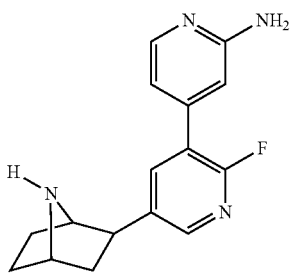

A solution of 2-amino-4-bromopyridine (1.16 mmol, 1.0 equiv), bispinacolata diborane (1.21 mmol, 1.05 equiv), Pd$_2$dba$_3$ (0.035 mmol, 3 mol %), Xphos (0.185 mmol, 16 mol %), and KOAc (2.77 mmol, 2.4 mmol) in dioxane, placed in a resealable pressure vessel was degassed through bubbling nitrogen for 40 min then heated at 110° C. for 4 h. A TLC check revealed that all the bromopyridine had been converted to the boronic ester. The reaction was allowed to cool to room temperature, and K$_3$PO$_4$ (2.89 mmol, 2.5 equiv), a solution of 23 (0.1 mmol, 0.87 equiv) in dioxanes, an additional 3 mol % of Pd$_2$dba$_3$ and H$_2$O (1 mL) were added to the reaction. The mixture was degassed for 30 min and heated for 18 h at 110° C. The reaction was cooled to room temperature and extracted with EtOAC (3×30 mL). The combined organic layers were dried over MgSO$_4$, filtered through Celite and the solvent was removed in vacuo. Two purifications of the residue by flash chromatography through an ISCO column using CHCl$_3$/MeOH (10:1) provided 60 mg (21%) of 39 as a colorless oil. $^1$H NMR (300 MHz, CDCl$_3$) δ 1.51-1.71 (m, 5H), 1.90-1.97 (m, 1H), 2.36 (br s, 1H), 2.80-2.85 (dd, J=3.8, 5.0 Hz, 1H), 3.61 (s, 1H), 3.81 (d, J=2.7 Hz, 1H), 4.66 (br s, 2H), 6.72 (s, 1H), 6.84 (d, J=5.3 Hz, 1H), 8.02 (dd, J=2.3, 9.5 Hz, 1H), 8.11 (s, 1H), 8.13 (d, J=5.7 Hz, 1H); $^{13}$CNMR (CDCl$_3$) δ 30.2, 31.4, 40.5, 44.3, 56.5, 62.9, 108.1, 113.9, 139.4, 140.6, 143.7, 145.9, 148.5, 157.4, 158.8, 160.6; MS (ESI) m/z 285.5 (M+H)$^+$.

2-Fluoro-3-(2'-amino-4'-pyridinyl)deschloroepibatidine hydrochloride (40)

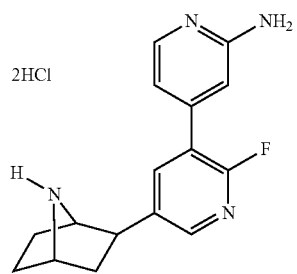

Prepared in similar protocol as compound 36 to provide 90% yield of the salt as a white solid. Mp. 205-208° C. $^1$H NMR (300 MHz, CD$_3$OD) δ 1.83-2.28 (m, 5H), 2.46-2.53 (dd, J=3.8, 9.6 Hz, 1H), 3.52-3.57 (dd, J=3.1, 5.5 Hz, 1H), 4.37 (d, J=3.6 Hz, 1H), 4.59 (d, J=2.7 Hz, 1H), 7.02-7.05 (dd, J=1.6, 6.1 Hz, 1H), 7.10 (s, 1H) 7.98 (d, J=6.1 Hz, 1H) 8.16 (dd, J=2.3, 9.2 Hz, 1H) 8.28 (s, 1H); $^{13}$CNMR (CD$_3$OD) δ 26.8, 28.9, 37.5, 43.3, 60.5, 64.2, 112.0, 113.8, 137.4, 141.3, 143.2, 148.0, 148.2, 158.8, 158.9, 162.1; MS (ESI) m/z 285.7 [(M-HCl)$^+$, M=C$_{16}$H$_{17}$FN$_4$.2HCl]; Anal. (C$_{16}$H$_{19}$Cl$_2$FN$_4$) C, H, N.

Example 5

Synthesis of Epibatidine Analogues 41-45

The analogues synthesized in the exemplary procedures discussed under this section differ from the analogues discussed under Examples 1 through 4 in that the fluoro group at the C-2' position is replaced with a hydrogen.

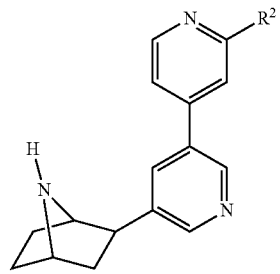

41, R$^2$ = Cl
42, R$^2$ = F
43, R$^2$ = H
44, R$^2$ = NH$_2$
45, R$^2$ = OMe

Syntheses of Analogues 41-43

The synthesis of the deschloroepibatidine analogues 41 to 43 started with the Heck cross coupling of 7-text-butoxycarbonylazabicyclo[2.2.1]heptene 4 and 3,5-dibromopyridine or 3-bromo-5-iodopyridine in the presence of Pd(OAc)$_2$, n-Bu$_4$NCl and potassium formate, heated in DMF at 100° C. for 48 h to provide 7-tert-butoxycarbonyl-2-exo-(3'-bromo-5'-pyridinyl)-7-azabicyclo[2.2.1]heptane, 48 in yields of between 40% and 59% (Scheme 10). For analogs 41 and 42, the substituted azabicyclo heptane 48 was subjected to Suzuki cross-coupling with the respective boronic acids in the presence of Pd(OAc)$_2$ and P(o-tolyl)$_3$ as the catalytic system, Na$_2$CO$_3$ as the base, DME as solvent with a catalytic amount of water and was heated at 80° C. for 5 h to furnish the bipyridine derivatives 49 and 50 (Scheme 11). In the case of analog 43, the Suzuki cross-coupling of 48 with 4-pyridine boronic acid in the presence of Pd(PPh$_3$)$_4$ and K$_2$CO$_3$ as base, heated at reflux in toluene (15 mL), ethanol (2 mL) and water (2 mL) for 24 h provided the desired product 51 in a 55% yield. Removal of the Boc in compounds 49-51 was accomplished using TFA in CH$_2$Cl$_2$ to provide the analogs 41, 42 and 43 which were then converted to the fumarate salts.

Scheme 10.

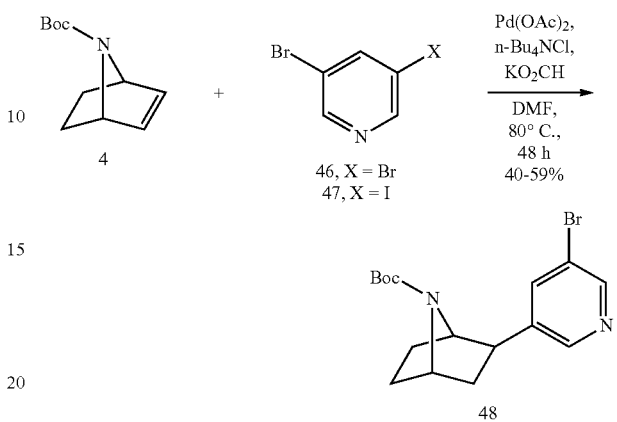

Scheme 11.

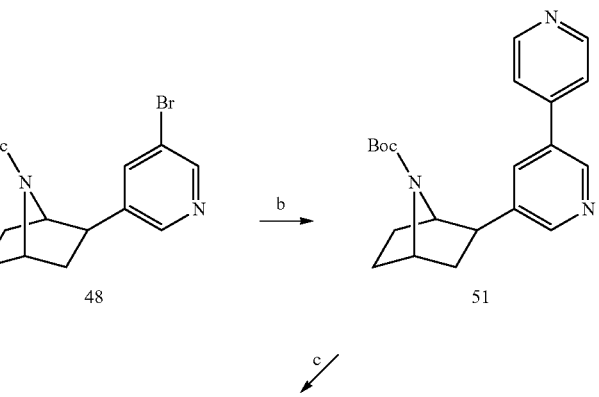

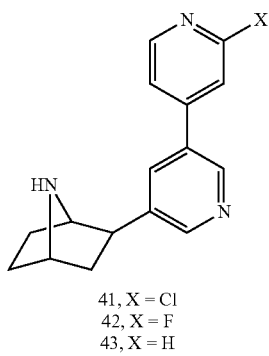

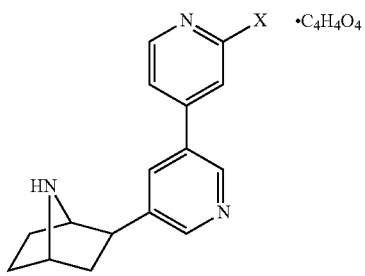

52, X = Cl
53, X = F
54, X = H

Reagents and condintions for Scheme 11: (a) Pd(OAc)₂, P(o-tolyl)₃, RB(OH)₂, Na₂CO₃, DME, H₂O, 80° C., 5 h (b) Pd(PPh₃)₄, C₅H₄NB(OH)₂, K₂CO₃, toluene, EtOH, H₂O, reflux, 18 h (c) TFA, CH₂Cl₂, rt, 3 h (d) Fumaric acid (1.3 equiv), MeOH/Et₂O Experimental Procedure 7-tert-butoxycarbonyl-2-exo-(3'-bromo-5'-pyridinyl)-7-azabicyclo[2.2.1]heptane (48)

A solution of 7-tert-butoxycarbonylazabicyclo[2.2.1]heptene (4) (2.16 g, 12.9 mmol, 1.0 equiv) in DMF (10 mL), 3,5-dibromopyridine (7.3 g, 25.8 mmol, 2.0 equiv), n-Bu₄NCl (900 mg, 3.22 mmol, 25 mol %) and Pd(OAc)₂ (145 mg, 0.65 mmol, 5 mol %) was placed in a resealable pressure vessel, degassed through bubbling nitrogen for 40 min and was then heated at 80° C. After 48 h, the mixture was cooled to rt, diluted with EtOAc, and filtered though Celite into a flask containing a 1:1 solution of NH₄OH/ H₂O (100 mL). The organic product was extracted with CHCl₃ (3×100 mL). The combined organic layers were dried over MgSO₄, filtered through Celite and solvent removed in vacuo. Purification of the residue by flash chromatography through an ISCO column provided 1.82 g (40%) of 48 as a white solid. ¹H NMR (300 MHz, CDCl₃) δ 1.45 (br s, 9H), 1.49-1.61 (m, 2H), 1.81-1.85 (m, 3H), 1.97-2.04 (m, 1H), 2.86-2.91 (m, 1H), 4.21 (s, 1H), 4.39 (br s, 1H), 7.81 (s, 1H), 8.42 (d, J=1.7 Hz, 1H), 8.49 (d, J=2.0 Hz, 1H); ¹³C NMR (CDCl₃) δ 28.2 (3C), 28.7, 29.6, 40.0, 45.2, 55.8, 61.6, 79.7, 120.7, 136.7, 142.8, 147.1, 148.6; MS (ESI) m/z 353.3 (M+H)⁺.

General Procedure for the Synthesis of 49 and 50.

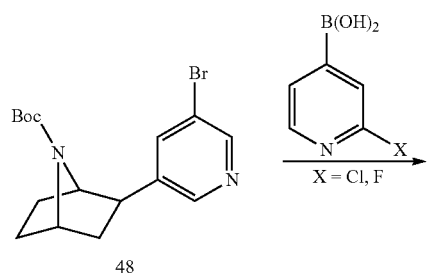

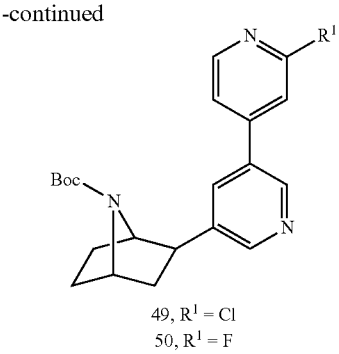

49, R¹ = Cl
50, R¹ = F

To a resealable reaction vessel under nitrogen was added 1.0 equiv of 48, Pd(OAc)₂ (0.1 equiv), P(o-tolyl)₃ (0.2 equiv), sodium carbonate (2.0 equiv) and the respective pyridinyl boronic acid (1.6 equiv), DME (6 mL) and water (0.7 mL). The mixture was degassed through bubbling nitrogen for 40 min and heated at 80° C. for 5 h. The mixture was cooled, poured into 20 mL of a saturated aqueous solution of NaHCO₃ (20 mL) and extracted with EtOAc (3×30 mL). The combined organic layers were dried over MgSO₄, filtered through Celite and the solvent removed under reduced pressure. The resultant residue was purified by flash chromatography (EtOAc/hexanes).

7-tert-Butoxycarbonyl-2-exo-[3'-(2-chloropyridin-4-yl)-5'-pyridinyl]-7-azabicyclo[2.2.1]heptane (49)

The reagents were compound 48 and 2-chloropyridine-4-boronic acid. ¹H NMR (300 MHz, CDCl₃) δ 1.45 (br s, 9H), 1.48-1.69 (m, 2H), 1.87-1.91 (m, 3H), 2.05-2.12 (m, 1H), 2.98-3.03 (m, 1H), 4.29 (s, 1H), 4.43 (br s, 1H), 4.54 (s, 2 NH), 7.46 (dd, J=1.5, 4.2 Hz, 1H), 7.55 (s, 1H), 7.94 (t, J=2.0 Hz, 1H), 8.47 (d, J=5.2 Hz, 1H), 8.58 (d, J=2.0 Hz, 1H), 8.71 (d, J=2.2 Hz, 1H); ¹³C NMR (CDCl₃) δ 28.3 (3C), 28.8, 29.7, 40.5, 45.3, 55.9, 61.7, 79.9, 120.3, 122.0, 132.4, 132.5, 141.7, 145.8, 148.5, 150.0, 150.2, 152.4, 154.9; MS (ESI) m/z 386.6 (M+H)⁺.

7-tert-Butoxycarbonyl-2-exo-[3'-(2-fluoropyridin-4-yl)-5'-pyridinyl]-7-azabicyclo[2.2.1]heptane (50)

The reagents were compound 48 and 2-fluoropyridine-4-boronic acid. ¹H NMR (300 MHz, CDCl₃) δ 1.44 (br s, 9H), 1.48-1.69 (m, 2H), 1.87-1.93 (m, 3H), 2.05-2.12 (dd, J=9.0

Hz, 1H), 2.99-3.03 (m, 1H), 4.29 (s, 1H), 4.43 (br s, 1H), 4.54 (s, 2 NH), 7.16 (s, 1H), 7.42-7.44 (dt, J=1.7, 5.2 Hz, 1H), 7.95 (t, J=2.0 Hz, 1H), 8.30 (d, J=5.3 Hz, 1H), 8.59 (d, J=2.0 Hz, 1H), 8.73 (d, J=2.2 Hz, 1H); $^{13}$C NMR (CDCl$_3$) δ 28.3 (3C), 28.8, 29.7, 40.5, 45.3, 56.0, 61.8, 79.9, 107.4, 119.4, 132.5, 141.6, 145.8, 148.2, 150.0, 150.9, 154.9, 162.9, 166.0; MS (ESI) m/z 386.6 (M+H)$^+$.

7-tert-Butoxycarbonyl-2-exo-[3'-(pyridin-4-yl)-5'-pyridinyl]-7-azabicyclo[2.2.1]heptane (51)

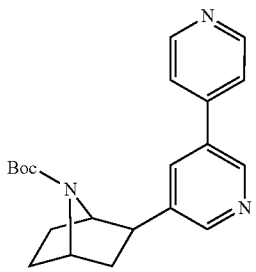

To a resealable reaction pressure vessel under nitrogen was added 48 (292 mg, 0.83 mmol, 1.0 equiv), Pd(PPh$_3$)$_4$ (48 mg, 0.041 mmol, 5 mol %), potassium carbonate (229 mg, 1.66 mmol, 2.0 equiv), pyridine 4-boronic acid (132 mg, 1.08 mmol, 1.3 equiv), toluene (15 mL), ethanol (2 mL) and water (2 mL). The mixture was degassed through bubbling nitrogen and heated at 110° C. for 24 h. After cooling to room temperature the mixture was poured into 30 mL of H$_2$O and extracted with EtOAc (3×30 mL). The combined organic layers were dried over MgSO$_4$, filtered through Celite and the solvent removed in vacuo. The resultant residue was purified by flash chromatography using hexanes/isopropanol to furnish 159 mg (55%) of 51 as an colorless oil. $^1$H NMR (300 MHz, CDCl$_3$) δ 1.43 (br s, 9H), 1.58-1.66 (m, 2H), 1.87-1.94 (m, 3H), 1.93-2.00 (m, 1H), 2.04-2.11 (dd, J=9.0 Hz, 1H), 2.97-3.02 (m, 1H), 4.29 (s, 1H), 4.43 (br s, 1H), 7.51-7.56 (m, 2H), 7.93 (d, J=1.9 Hz, 1H), 8.56 (d, J=1.9 Hz, 1H) 8.69-8.74 (m, 3H); $^{13}$C NMR (CDCl$_3$) δ; 28.3 (3C), 28.8, 29.8, 40.4, 45.4, 55.9, 61.8, 79.8, 121.5, 132.5, 133.5, 141.4, 145.3, 145.9, 149.4, 150.4, 154.8; MS (ESI) m/z 352.3 (M+H)$^+$.

General Procedure for Boc Removal in the Synthesis of Analogues 41-43.

A solution of the Boc protected analog in CH$_2$Cl$_2$ (5 mL) and TFA (1 mL) was stirred at rt for between 1 and 3 h. The solvent was removed under reduced pressure and the residual was and treated with a 20 mL solution of NH$_4$OH/ H$_2$O (3:1). The organic product was extracted with CHCl$_3$ (3×30 mL), dried over anhydrous sodium sulfate, filtered through Celite and concentrated in vacuo. Purification of the residual by flash chromatography through an ISCO column provided the amine analogs 41-43 in quantitative yields as colorless oils.

2-exo-[3'-(2-Chloropyridin-4-yl)-5'-pyridinyl]-7-azabicyclo[2.2.1]heptane (41)

$^1$H NMR (300 MHz, CDCl$_3$) δ 1.57-1.74 (m, 6H), 1.93-2.00 (dd, J=9.1, 11.2 Hz, 1H), 2.85-2.89 (m, 1H), 3.65 (s, 1H), 3.83 (br s 1H), 7.45 (dd, J=1.5, 5.2 Hz, 1H), 7.56 (s, 1H), 8.05 (t, J=2.1 Hz, 1H), 8.47 (d, J=5.2 Hz, 1H) 8.62 (d, J=2.0 Hz, 1H), 8.68 (d, J=2.2 Hz, 1H); $^{13}$C NMR (CDCl$_3$) δ 30.3, 31.6, 40.4, 45.1, 56.4, 62.8, 120.5, 122.1, 132.3, 133.1, 142.7, 145.6, 148.8, 150.2, 152.4; MS (ESI) m/z 286.5 (M+H)$^+$.

2-exo-[3'-(2-Fluoropyridin-4-yl)-5'-pyridinyl]-7-azabicyclo[2.2.1]heptane (42)

$^1$H NMR (300 MHz, CDCl$_3$) δ 1.50-1.75 (m, 6H), 1.82 (br s, 1H), 1.94-2.01 (dd, J=9.0, 11.2 Hz, 1H), 2.85-2.90 (dd, J=3.9, 6.9 Hz, 1H), 3.65 (s, 1H), 3.84 (br s 1H), 7.17 (s, 1H), 7.43 (dt, J=1.6, 5.2 Hz, 1H), 8.07 (t, J=2.1 Hz, 1H), 8.29 (d, J=5.2 Hz, 1H) 8.63 (d, J=2.0 Hz, 1H), 8.71 (d, J=2.2 Hz, 1H); $^{13}$C NMR (CDCl$_3$) δ 30.3, 31.5, 40.1, 45.1, 56.4, 62.8, 107.0, 119.5, 133.1, 142.7, 145.6, 148.2, 148.4, 151.2, 162.8, 166; MS (ESI) m/z 270.4 (M+H)$^+$.

2-exo-[3'-(Pyridin-4-yl)-5'-pyridinyl]-7-azabicyclo[2.2.1]heptane (43)

$^1$H NMR (300 MHz, CDCl$_3$) δ 1.50-1.88 (m, 7H), 1.93-2.00 (dd, J=9.0, 11.2 Hz, 1H), 2.85-2.90 (dd, J=3.9, 6.9 Hz, 1H), 3.65 (s, 1H), 3.82 (br s 1H), 7.53 (d, J=5.6 Hz, 2H), 8.04 (t, J=2.0 Hz, 1H), 8.60-8.71 (m, 4H); $^{13}$C NMR (CDCl$_3$) δ 30.2, 31.5, 40.4, 45.2, 56.4, 62.8, 121.6, 133.0, 133.5, 142.5, 145.6, 149.6, 150.4; MS (ESI) m/z 252.3 (M+H)$^+$.

General Procedure for the Preparation of the Fumarates Salts of Analogues 41, 42 and 43.

A solution of the amine in ether (2 mL) was treated with a solution of fumaric acid (1.2 equivalent) in MeOH. The mixture was left to stand in a refrigerator overnight. Filtration and washing of the filter cake with ether, followed by recrystallization from MeOH-ether provided fumarate salts 52, 53, and 54.2-exo-3'-(2"-Chloro-4"-pyridinyl)deschloroepibatidine fumarate (52).

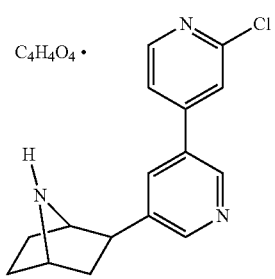

$^1$H NMR (500 MHz, METHANOL-d$_4$) δ 8.85 (d, J=1.95 Hz, 1H), 8.65 (d J=1.85 Hz, 1H), 8.48 (d, J=5.35 Hz, 1H), 8.20-8.23 (m, 1H), 7.90-7.93 (m, 1H), 7.77 (dd, J=1.66, 5.27 Hz, 1H), 6.69 (s, 2H), 4.61-4.64 (br s, 1H), 4.35-4.38 (br s, 1H), 3.53-3.59 (m, 1H), 2.47-2.55 (m, 1H), 2.21-2.21 (m, 1H), 2.07-2.11 (m, 1H), 1.98-2.07 (m, 1H), 1.89-1.97 (m, 1H); $^{13}$C NMR (500 MHz, METHANOL-d$_4$) δ 27.0, 29.1, 37.8, 44.0, 60.4, 64.0, 122.3, 123.7 134.3, 135.1, 136.0, 139.7, 147.4, 150.0, 150.7, 151.5, 153.5, 170.5; MS (ESI) m/z 286.5 [(M-fumarate)⁺, M=C₁₆H₁₆ClN₃.C₄H₄O₄]. Anal. (C₂₀H₂₀ClN₃O₄), C, H, N.

2-exo-3'-(2"-Fluoro-4"-pyridinyl)deschloroepibatidine fumarate (53)

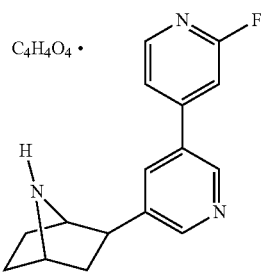

Mp. 210-214° C.; ¹H NMR (500 MHz, METHANOL-d₄) δ 8.87 (d, J=1.74 Hz, 1H), 8.65 (d, J=1.74 Hz, 1H), 8.33 (d, J=5.23 Hz, 1H), 8.22-8.23 (m, 1H), 7.72 (td, J=1.70, 5.32 Hz, 1H), 7.52 (s, 1H), 6.671 (s, 2H), 4.63 (br s, 1H), 4.35-4.37 (br s, 1H), 3.55-3.57 (m, 1H), 3.57 (d, J=5.93 Hz, 1H), 2.50 (d, J=9.76 Hz, 3H), 2.52 (d, J=9.76 Hz, 3H), 2.21 (s, 6H), 1.98-2.16 (m, 17H), 1.87-1.908 (m, 6H); ¹³C (500 MHz, METHANOL-d₄) δ 27.3, 29.1, 37.7, 44.0, 60.4, 64.0, 108.6, 121.2, 135.1, 136.0, 139.7, 147.3, 149.5, 149.6, 150.6, 170.5; MS (ESI) m/z 270.2 [(M-fumarate)⁺, M=C₁₆H₁₆FN₃.C₄H₄O₄]. Anal. (C₂₀H₂₀FN₃O₄.0.5H₂O), C, H, N.

2-exo-3'-(4"-Pyridinyl)deschloroepibatidine fumarate (54)

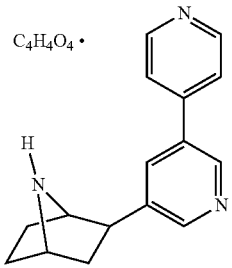

¹H NMR (500 MHz, METHANOL-d₄) δ 8.85 (d, J=1.74 Hz, 1H), 8.66-8.67 (m, 2H), 8.64 (d, J=2.1 Hz, 1H), 8.21-8.22 (m, 1H), 7.83-7.84 (m, 2H), 6.69 (s, 2H), 4.63 (d, J=3.83 Hz, 1H), 4.37 (br s, 1H), 3.57 (dd, J=6.10, 9.59 Hz, 1H), 2.52 (dd, J=9.59, 13.42 Hz, 1H), 2.15-2.26 (m, 1H), 1.97-2.15 (m, 4H), 1.82-1.97 (m, 1H); ¹³C NMR (500 MHz, METHANOL-d₄) δ 27.03, 29.07, 37.72, 44.01, 60.44, 64.00, 123.57, 135.07, 135.33, 135.90, 139.60, 147.17, 147.30, 150.14, 151.06, 170.06; MS (ESI) m/z 252.3 [(M-fumarate)⁺, M=C₁₆H₁₇N₃.C₄H₄O₄]. Anal. (C₂₀H₂₁N₃O₄), C, H, N.

Synthesis of Analogue 44 and 45.

The synthesis of the hydrochloride salt of 44 was accomplished as illustrated in Scheme 12. The bromo compound 48 was subjected to a borylation reaction through cross-coupling reaction with bis(pinacolato)diborane in the presence of potassium acetate as base and PdCl₂(dppf) as the catalyst and heated in dioxane at 110° C. overnight to provide the boronic ester 55 in a 84% yield upon purification. The boronic ester was then subjected to a Suzuki-Miyaura cross-coupling reaction with 2-amino-4-bromopyridine (37) to provide compound 56 in a 74% yield. Removal of the Boc protecting group was accomplished by stirring 56 in TFA/ CH₂Cl₂ at room temperature for 1 h. The amine 44 obtained was converted to a hydrochloride salt 57 using a solution of HCl in diethyl ether.

Scheme 12.

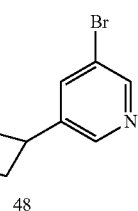

48

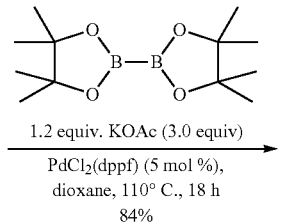

1.2 equiv. KOAc (3.0 equiv)
PdCl₂(dppf) (5 mol %),
dioxane, 110° C., 18 h
84%

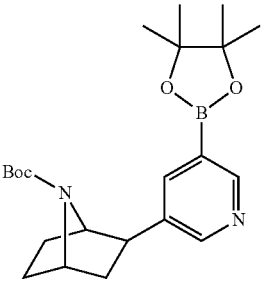

55

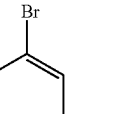

37

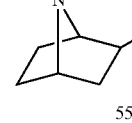

55

Pd(PPh₃)₄ (5 mol %),
K₂CO₃ (2.0 equiv)
dioxane, H₂O,
110° C., overnight
74%

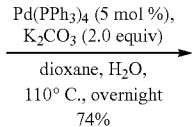

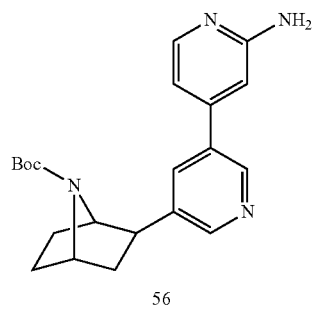

56

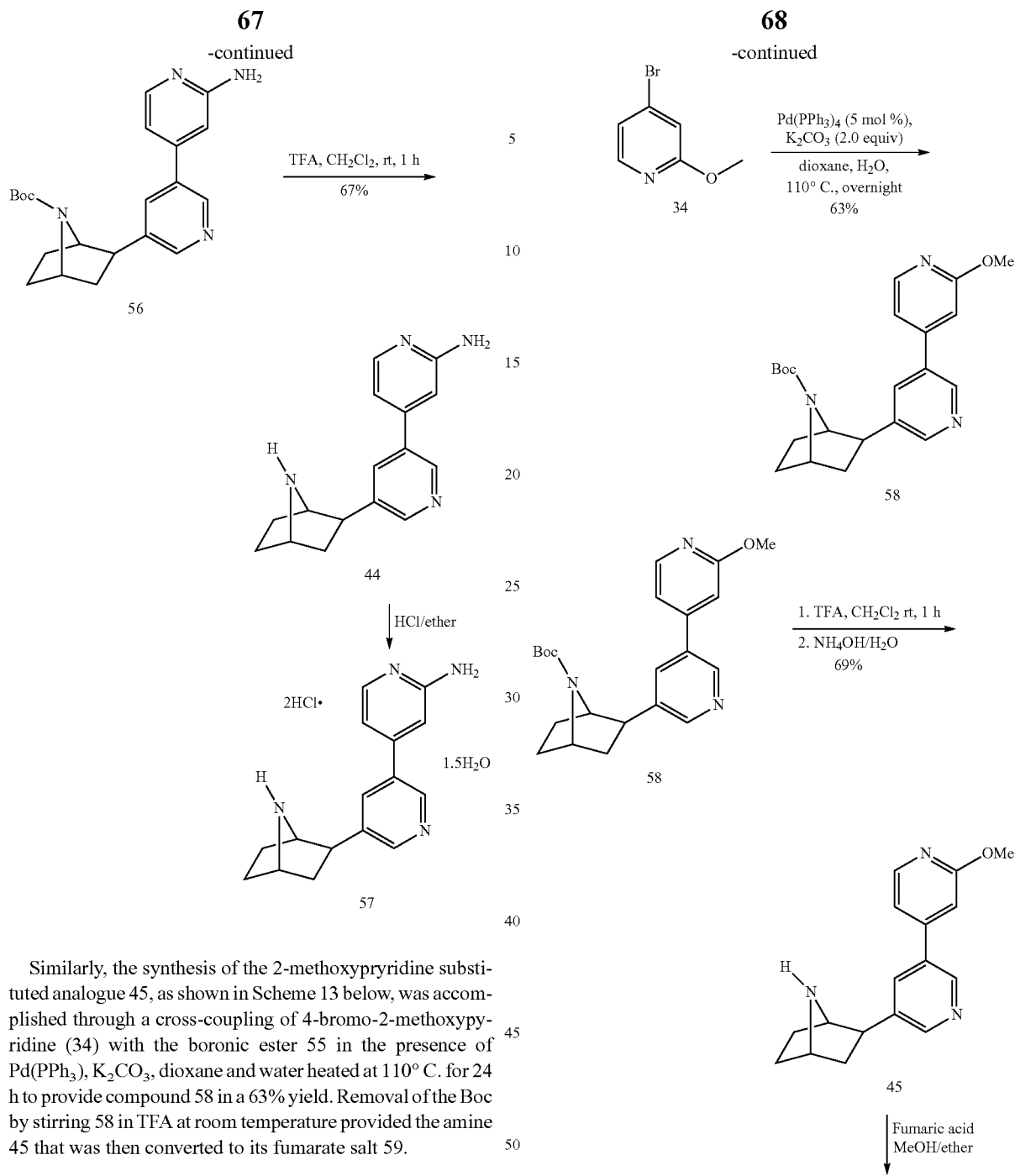

Similarly, the synthesis of the 2-methoxypryridine substituted analogue 45, as shown in Scheme 13 below, was accomplished through a cross-coupling of 4-bromo-2-methoxypyridine (34) with the boronic ester 55 in the presence of Pd(PPh$_3$), K$_2$CO$_3$, dioxane and water heated at 110° C. for 24 h to provide compound 58 in a 63% yield. Removal of the Boc by stirring 58 in TFA at room temperature provided the amine 45 that was then converted to its fumarate salt 59.

Scheme 13.

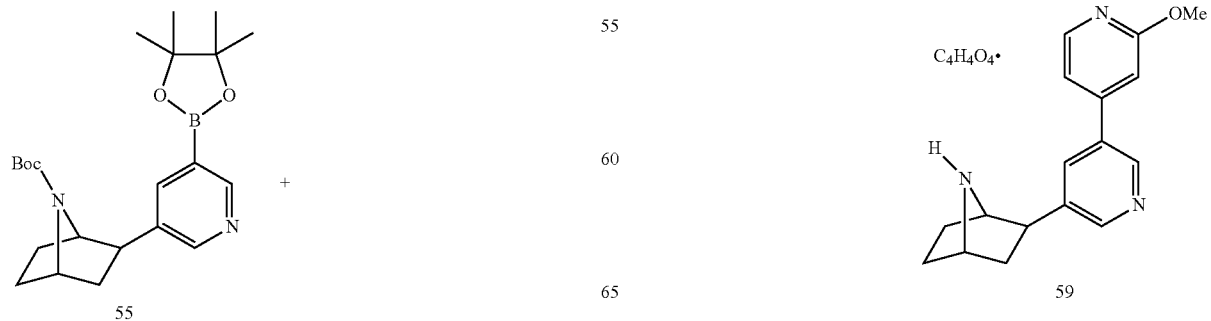

Experimental Procedure

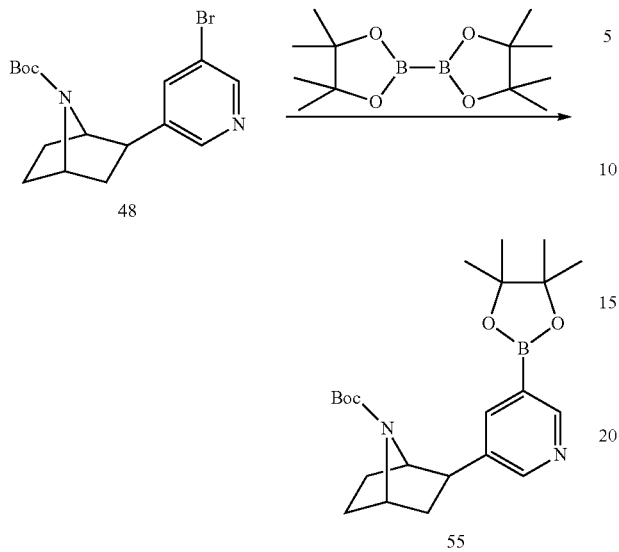

48

55

7-tert-Butoxycarbonyl-2-exo-[5'-(4,4,5,5-tetramethyl-1,3,2-dioxaborolan-2-yl)-3'-pyridinyl]-7-azabicyclo[2.2.1]heptane (55)

To a resealable reaction pressure vessel under nitrogen was added a solution of 48 (7-tert-butoxycarbonyl-2-exo-(3'-bromo-5'-pyridinyl)-7-azabicyclo[2.2.1]heptane) (209 mg, 0.5904 mmol, 1.0 equiv), $PdCl_2(dppf)$ (22 mg, 0.0295 mmol, 5 mol %), and KOAC (180 mg, 1.83 mmol, 3.0 equiv) in dioxane (10 mL). The mixture was degassed through bubbling nitrogen for 40 min then heated at 110° C. for 24 h. After cooling to room temperature the reaction was diluted in EtOAc and filtered through a plug of Celite and anhydrous sodium sulfate. The solvent was removed in vacuo and the residue was purified by flash chromatography (EtAOc) to provide 199 mg (84%) of 55 as a brownish oil.

7-tert-Butoxycarbonyl-2-exo-[3'-(2-aminopyridin-4-yl)-5'-pyridinyl]-7-azabicyclo[2.2.1]heptane (56)

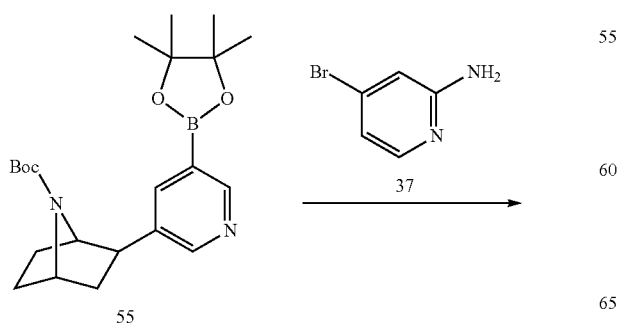

55    37

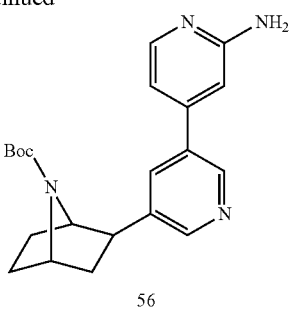

56

To a resealable reaction pressure vessel under nitrogen was added 1.0 equiv of 55 (265 mg, 0.662 mmol), $Pd(PPh_3)_4$ (38 mg, 0.033 mmol, 5 mol %), $K_2CO_3$ (184 mg, 1.324 mmol, 2.0 equiv), 2-amino-4-bromopyridine (137 mg, 0.794 mmol, 1.2 equiv), dioxane (12 mL) and water (1 mL). The mixture was degassed through bubbling nitrogen for 40 min and heated at 110° C. for 20 h. After cooling to room temperature, water (10 mL) was added and the organic product was extracted using EtOAc (3×30 mL). The combined organic layers were dried over $MgSO_4$, filtered through Celite and the solvent removed in vacuo. The residual was purified by flash chromatography to provide 180 mg (74%) of 56 as colorless oil. $^1H$ NMR (300 MHz, $CDCl_3$) δ 1.43 (br s, 9H), 1.53-1.66 (m, 2H), 1.80-1.91 (m, 3H), 2.01-2.08 (m, 1H), 2.94-2.98 (m, 1H), 4.27 (s, 1H), 4.41 (br s, 1H), 4.76 (s, 2 NH), 6.70 (s, 1H), 6.85 (d, J=4.3 Hz, 1H), 7.85 (s, 1H), 8.13 (d, J=5.3 Hz, 1H), 8.52 (d, J=1.7 Hz, 1H), 8.67 (d, J=1.2 Hz, 1H); $^{13}C$ NMR ($CDCl_3$) δ 28.3 (3C), 28.8, 29.8, 40.4, 45.5, 55.9, 61.8, 79.8, 106.2, 112.3, 132.5, 134.2, 141.2, 145.9, 147.1, 148.8, 149.1, 154.9, 159.1; MS (ESI) m/z 367.6 (M+H)$^+$.

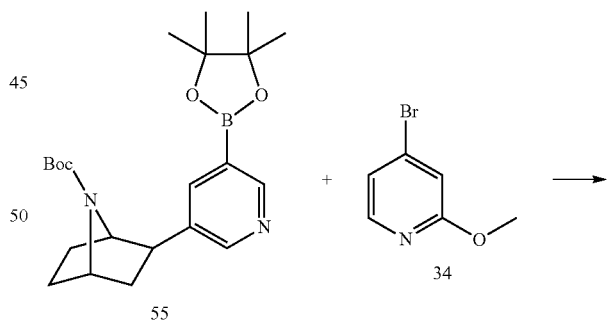

55    34

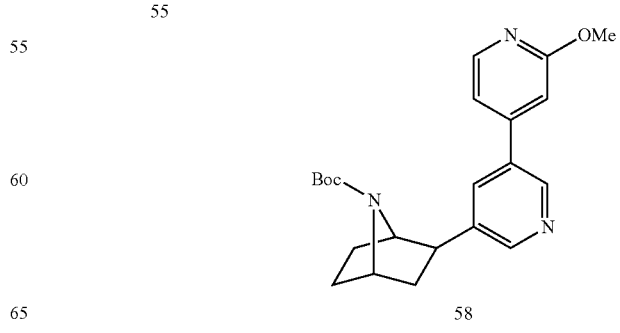

58

7-tert-Butoxycarbonyl-2-exo-[3'-(2-aminopyridin-4-yl)-5'-pyridinyl]-7-azabicyclo[2.2.1]heptane (58)

To a resealable reaction pressure vessel under nitrogen was added 1.0 equiv of 55 (266 mg, 0.665 mmol), Pd(PPh$_3$)$_4$ (38 mg, 0.033 mmol, 5 mol %), K$_2$CO$_3$ (184 mg, 1.33 mmol, 2.0 equiv), 2-methoxy-4-bromopyridine (137 mg, 0.732 mmol, 1.1 equiv), dioxane (20 mL) and water (2 mL). The mixture was degassed through bubbling nitrogen for 40 min and heated at 110° C. overnight. After cooling to room temperature, water (20 mL) was added and the organic product was extracted using EtOAc (3×30 mL). The combined organic layers were dried over MgSO$_4$, filtered through Celite and the solvent removed in vacuo. The residual was purified by flash chromatography to provide 160 mg (63%) of 58 as colorless oil. $^1$H NMR (300 MHz, CDCl$_3$) δ 1.42 (br s, 9H), 1.49-1.63 (m, 2H), 1.86-1.98 (m, 3H), 2.00-2.07 (m, 1H), 2.96-3.01 (m, 1H), 3.92 (s, 3H), 4.30 (s, 1H), 4.42 (br s, 1H), 6.81 (dd, J=5.7, 2.4 Hz, 1H), 7.25 (d, J=2.2 Hz, 1H), 8.22 (t, J=1.9 Hz, 1H), 8.53 (d, J=5.7 Hz, 1H), 8.56 (d, J=2.0 Hz, 1H), 9.00 (d, J=2.0 Hz, 1H); $^{13}$C NMR (CDCl$_3$) δ 28.3 (3C), 28.8, 29.9, 40.2, 45.8, 55.9, 61.8, 79.7, 107.2, 108.6, 132.9, 134.7, 140.9, 146.2, 149.1, 151.1, 155.0, 156.7 166.5; MS (ESI) m/z 382.7 (M+H)$^+$.

General Procedure for Boc Removal in the Synthesis of Analogues 56 and 58.

A solution of the Boc protected analog in CH$_2$Cl$_2$ (5 mL) and TFA (1 mL) was stirred at rt for between 1 and 3 h. The solvent was removed under reduced pressure and the residual was and treated with a 20 mL solution of NH$_4$OH/ H$_2$O (3:1). The organic product was extracted with CHCl$_3$ (3×30 mL), dried over anhydrous sodium sulfate, filtered through Celite and concentrated in vacuo. Purification of the residual by flash chromatography through an ISCO column provided the amine analogues 44 and 45 in good yields as colorless oils.

2-exo-[3'-(2-Aminopyridin-4-yl)-5'-pyridinyl]-7-azabicyclo[2.2.1]heptane (44)

$^1$H NMR (300 MHz, CDCl$_3$) δ 1.50-1.76 (m, 6H), 1.86 (br s, 1H) 1.92-1.99 (dd, J=9.0, 11.2 Hz, 1H), 2.84-2.88 (dd, J=3.9, 6.9 Hz, 1H), 3.64 (s, 1H), 3.83 (br s 1H), 4.69 (br s, 2H) 6.70 (s, 1H), 6.85 (dd, J=1.1, 5.3 Hz, 1H), 7.85 (d, J=1.7 Hz, 1H), 8.13 (d, J=5.3 Hz, 1H), 8.55 (d, J=1.8 Hz, 1H), 8.65 (d, J=2.0 Hz, 1H); $^{13}$C NMR (CDCl$_3$) δ 30.2, 31.5, 40.4, 45.2, 56.5, 62.8, 106.2, 112.5, 132.9, 134.1, 142.2, 145.6, 147.4, 148.9, 149.3, 159.1; MS (ESI) m/z 267.1 (M+H)$^+$.

2-exo-[3'-(2-Methoxypyridin-4-yl)-5'-pyridinyl]-7-azabicyclo[2.2.1]heptane (45)

$^1$H NMR (300 MHz, CDCl$_3$) δ 1.50-1.76 (m, 6H), 1.86 (br s, 1H) 1.92-1.99 (dd, J=9.0, 11.2 Hz, 1H), 2.84-2.88 (dd, J=3.9, 6.9 Hz, 1H), 3.64 (s, 1H), 3.83 (br s 1H), 4.69 (br s, 2H) 6.70 (s, 1H), 6.85 (dd, J=1.1, 5.3 Hz, 1H), 7.85 (d, J=1.7 Hz, 1H), 8.13 (d, J=5.3 Hz, 1H), 8.55 (d, J=1.8 Hz, 1H), 8.65 (d, J=2.0 Hz, 1H); $^{13}$C NMR (CDCl$_3$) δ 30.0, 31.3, 40.2, 45.5, 55.2, 56.5, 62.8, 107.3, 108.4, 133.1, 134.6, 141.8, 145.8, 149.4, 151.2, 156.8, 166.4; MS (ESI) m/z 282.5 (M+H)$^+$.

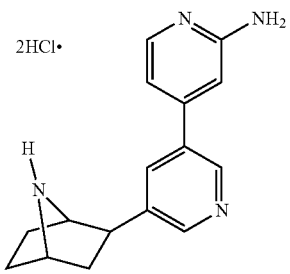

2-exo-3'-(2''-Amino-4''-pyridinyl)deschloroepibatidine Hydrochloride (57)

Prepared using HCl in diethyl ether and recrystallized from MeOH/ diethyl ether to provide 66% yield of the salt as a purplish solid. Mp. 209-214° C. $^1$H NMR (300 MHz, CD$_3$OD) δ 1.90-2.0 (m, 4H), 2.10-2.34 (m, 1H), 2.52-2.60 (dd, J=9.0, 11.2 Hz, 1H), 3.64-3.69 (dd, J=3.9, 6.9 Hz, 1H), 4.42 (s, 1H), 4.70 (br s 1H), 7.38 (dd, J=1.6, 6.8 Hz, 1H), 7.49 (s, 1H), 8.01 (d, J=6.7 Hz, 1H), 8.49 (s, 1H), 8.82 (s, 1H), 8.96 (s, 1H); $^{13}$CNMR (CD$_3$OD) δ 26.8, 28.9, 37.4, 43.9, 60.5, 64.0, 112.5, 112.7, 137.3, 137.4, 140.3, 145.9, 149.9, 153.2; MS (ESI) m/z 267.2 [(M−HCl)$^+$, M=C$_{16}$H$_{18}$N$_4$.2HCl]; Anal. (C$_{16}$H$_{20}$Cl$_2$N$_4$.1.5H$_2$O), C, H, N.

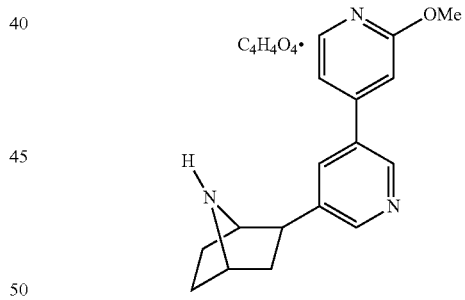

2-exo-(2''-Methoxy-4''-pyridinyl)deschloroepibatidine fumarate (59)

Mp. 160-164° C.; $^1$H NMR (300 MHz, METHANOL-d$_4$) δ 8.99 (d, J=1.74 Hz, 1H) 8.60 (d, J=1.71 Hz, 1H), 8.51 (d, J=5.85 Hz, 1H), 7.52 (d, J=1.8 Hz, 1H), 7.04 (dd, J=2.4, 5.82 Hz, 1H), 6.68 (s, 1H), 4.60 (d, J=2.0 Hz, 1H), 4.37 (br s, 1H), 3.98 (s, 3H), 3.57 (dd, J=3.3, 9.3 Hz, 1H), 2.45-2.53 (m, 1H), 1.86-2.26 (m, 6H); $^{13}$C NMR (300 MHz, METHANOL-d$_4$) δ 26.99, 28.84, 37.33, 43.91, 56.32, 60.33, 64.15, 109.52, 110.58, 134.72, 135.87, 138.97, 147.41, 149.72, 152.18, 157.20, 170.89; MS (ESI) m/z 282.4 [(M-fumarate)$^+$, M=C$_{16}$H$_{16}$FN$_3$.C$_4$H$_4$O$_4$]. Anal. (C$_{20}$H$_{20}$FN$_3$O$_4$.0.5H$_2$O), C, H, N.

Example 6

Synthesis of Epibatidine Analogues-2'-Pyrimidinedeschloroepibatidine and 2'-Pyridazine Analogues

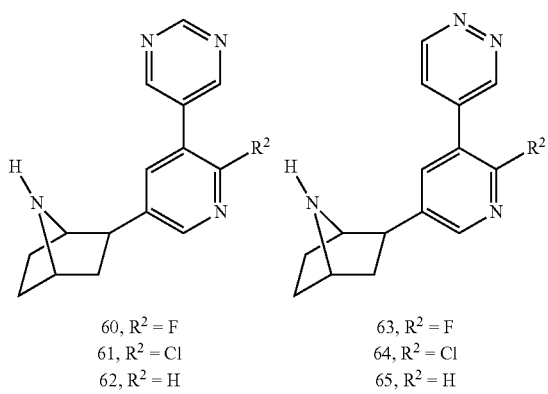

60, R² = F
61, R² = Cl
62, R² = H

63, R² = F
64, R² = Cl
65, R² = H

The exemplary procedures discussed below outline the routes to the synthesis of the pyrimidine analogues 60, 61 and 62.

The synthesis of all the analogues started with the Heck cross-coupling of olefin 4 with either 3,5-dibromopyridine or 2-amino-5-iodopyridine in the presence of Pd(OAc)$_2$, n-Bu$_4$NCl and potassium formate, heated in DMF at 100° C. for 2 or 4 days to provide 6 or 48 respectively. Bromination of 6 was accomplished through the use of bromine in the presence of glacial acetic acid to provide 7 (Scheme 14).

The synthesis of the pyrimidine analogues 60 and 61 commenced with the cross-coupling of pyrimidine boronic acid with either of the bromo intermediates 7 or 48. Suzuki cross-coupling of either 7 or 48 with pyrimidine boronic acid in the presence of Pd(PPh$_3$)$_4$, Na$_2$CO$_3$, DME and water, heated at 100° C. for 24 h provided the pyrimidine substituted compounds 66 or 69 respectively (see Schemes 15 and 17). For the synthesis of the 2'-fluorinated analogue 60, as illustrated in Scheme 15, the diazotization of the amino functional group in compound 66 using 70% HF in pyridine provided the desired 2'-fluorinated amine 60 and this was subsequently converted to the fumarate salt 67. On the other hand, diazotization of 66 using HCl and NaNO$_2$ provided the 2'-chlorinated analogue 61, which was subsequently converted to the Fumarate salt 68 as shown in Scheme 16. The cross-coupled product 69 as outlined in Scheme 17 was treated with TFA for the removal of the Boc protecting group to provide analogue 62 that was converted to the fumarate salt 70.

Scheme 15.

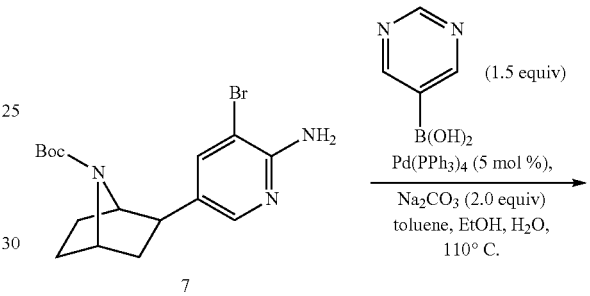

Scheme 14.

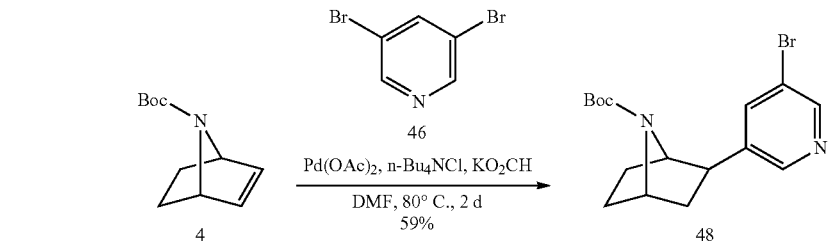

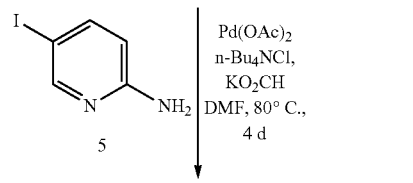

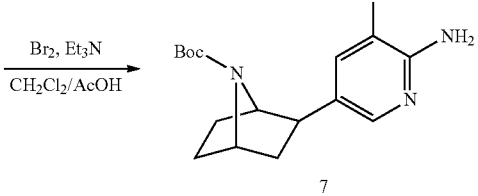

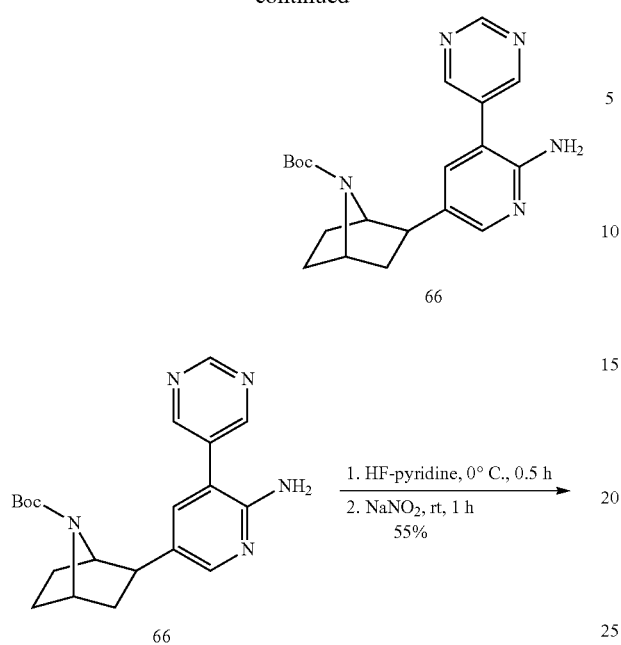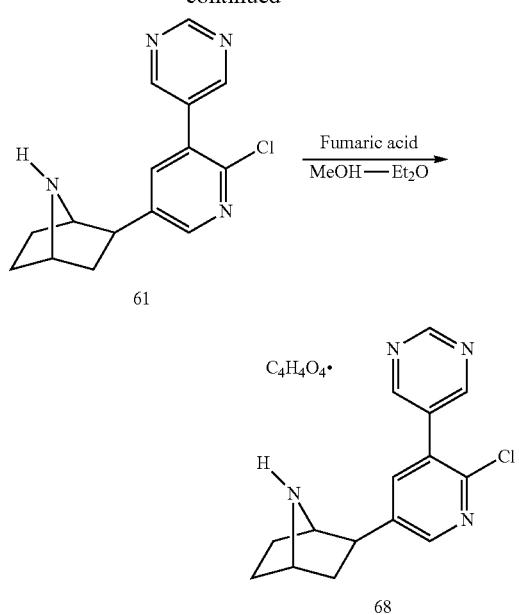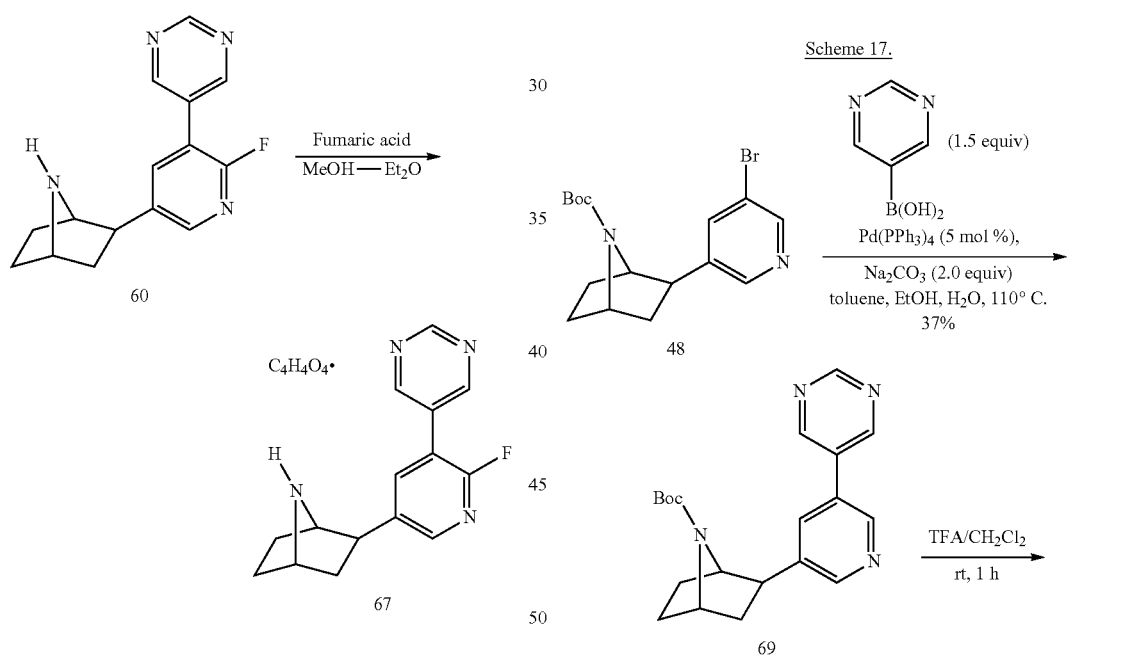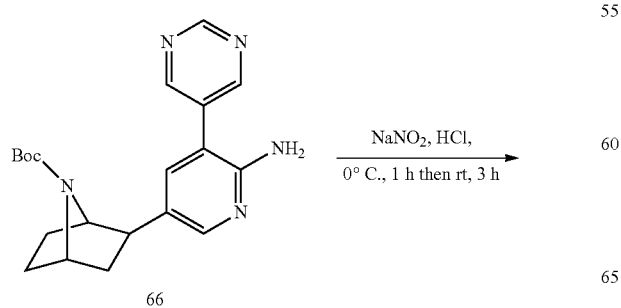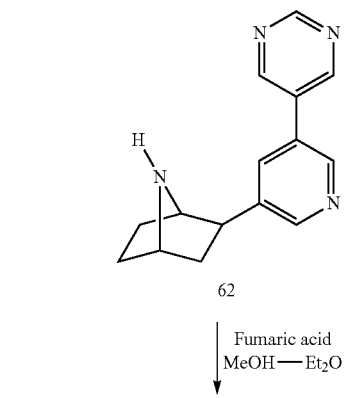

-continued

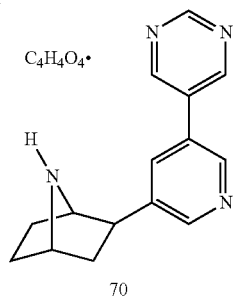

70

Experimental Procedure 7-tert-Butoxycarbonyl-2-exo-[2'-amino-3'-(pyrimidin-3-yl)-5'-pyridinyl]-7-azabicyclo[2.2.1]heptane (66)

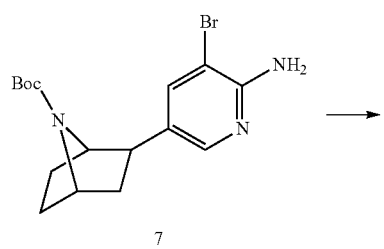

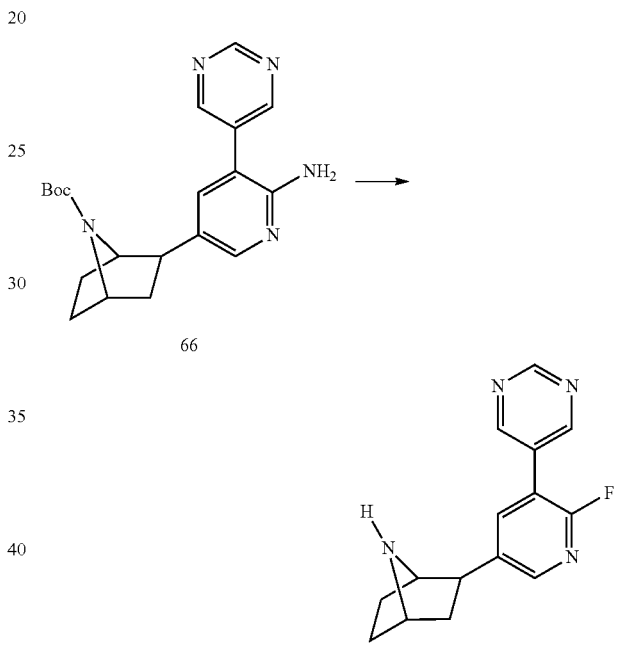

To a resealable reaction pressure vessel under nitrogen was added 7 (827, 2.25 mmol, 1.0 equiv), Pd(PPh$_3$)$_4$ (130, 0.112 mmol, 5 mol %), Na$_2$CO$_3$ (476 mg, 4.49 mmol, 2.0 equiv), pyrimidine boronic acid (362 mg, 2.92 mmol, 1.3 equiv), DME (12 mL), and water (1.5 mL). The mixture was degassed through bubbling nitrogen for 40 min and heated at 100° C. for 24 h. After cooling to room temperature the mixture was poured into 30 mL of H$_2$O and extracted with CHCl$_3$ (3×40 mL). The combined organic layers were dried over MgSO$_4$, filtered through Celite and the solvent removed in vacuo. The resultant residue was purified by flash chromatography using hexanes/EtOAc to furnish 585 mg (71%) of 66 as yellowish oil. $^1$H NMR (300 MHz, CDCl$_3$) δ 1.44 (br s, 9H), 1.49-1.62 (m, 3H), 1.81-1.85 (m, 3H), 1.95-2.02 (m, 1H), 2.80-2.84 (dd, J=9.0 Hz, 1H), 4.16 (s, 1H), 4.35 (br s, 1H), 7.37 (d, J=1.7 Hz, 1H), 8.01 (d, J=2.0 Hz, 1H) 8.86 (s, 2H), 9.18 (s, 1H); $^{13}$C NMR (CDCl$_3$) 6; 28.2 (3C), 28.7, 29.6, 40.2, 44.7, 55.8, 62.1, 79.5, 114.3, 132.1, 132.4, 137.0, 147.5, 154.6, 154.9, 156.6, 157.5; MS (ESI) m/z 368.4 (M+H)$^+$.

2-exo-[2'-Fluoro-3'-(pyrimidin-3-yl)-5'-pyridinyl]-7-azabicyclo[2.2.1]heptane (60)

A solution of 66 (353 mg, 0.961 mmol, 1.0 equiv) in 70% HF-pyridine (3 mL) in a plastic reaction vessel was stirred at 0° C. for 30 min. Sodium nitrite (663 mg, 9.61 mmol, 10 equiv) was then added in small portions and the mixture stirred at room temperature for 1 h. The mixture was then poured into a solution of 1:1 NH$_4$OH/H$_2$O (40 mL) and extracted with CHCl$_3$ (3×50 mL). The combined organic layers were dried over MgSO$_4$, filtered through Celite and concentrated in vacuo. The residue was purified by flash chromatography using CHCl$_3$/MeOH (10:1) to provide 126 mg (48%) of 60 as a colorless oil. $^1$H NMR (300 MHz, CDCl$_3$) δ 1.55-1.81 (m, 6H), 1.92-1.99 (m, 1H), 2.83-2.87 (dd, J=3.8, 5.0 Hz, 1H), 4.16 (s, 1H), 3.61 (br s, 1H), 3.83 (s, 1H), 8.14-8.20 (s, 2H), 8.98 (s, 2H), 9.24 (s, 1H); $^{13}$C NMR (CDCl$_3$) δ 30.4, 31.5, 40.7, 44.3, 56.3, 62.9, 116.6, 128.5, 139.5, 141.6, 146.7, 156.2, 158.0, 160.5; MS (ESI) m/z 271.6 (M+H)$^+$.

7-tert-Butoxycarbonyl-2-exo-[2'-chloro-3'-(pyrimidin-5-yl)-5'-pyridinyl]-7-azabicyclo[2.2.1]heptane (61)

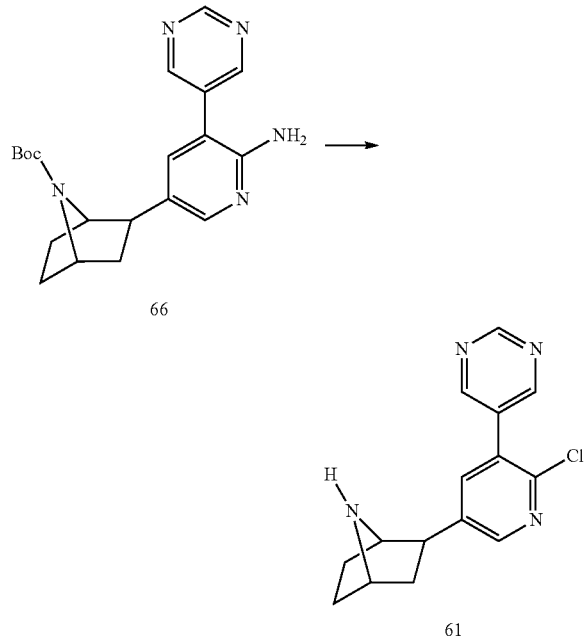

To a solution of 66 (390 mg, 1.06 mmol, 1.0 equiv) in HCl (10 mL) at 0° C. was added slowly NaNO$_2$ (1.47 g, 21.23 mmol, 20 equiv). The mixture was stirred at 0° C. for 1 h then at rt for an additional 3 h. The reaction was quenched with 20 mL NH$_4$OH/ H$_2$O (3:1) solution and extracted with CHCl$_3$ (3×30 mL). The combined organic layers were dried over MgSO$_4$, filtered through Celite and concentrated in vacuo. The residue obtained was purified by flash chromatography through an ISCO column using CHCl$_3$/MeOH (10:1) to provide 213 mg (70%) of the 61 as a colorless thick oil. $^1$H NMR (300 MHz, CDCl$_3$) δ 1.54-1.74 (m, 6H), 1.92-1.99 (m, 1H), 2.81-2.85 (dd, J=3.8, 5.0 Hz, 1H), 3.61 (s, 1H), 3.82 (br s, 1H), 7.93 (d, J=2.3 Hz, 1H) 8.40 (d, J=2.3 Hz, 1H), 8.88 (s, 2H), 9.26 (s, 1H); $^{13}$C NMR (CDCl$_3$) δ 30.4, 31.5, 40.5, 44.3, 56.3, 62.8, 123.8, 129.6, 131.8, 142.4, 147.0, 149.1, 156.7, 158.0; MS (ESI) m/z 287.3 (M+H)$^+$.

7-tert-Butoxycarbonyl-2-exo-[3'-(pyrimidin-5-yl)-5'-pyridinyl]-7-azabicyclo[2.2.1]heptane (69)

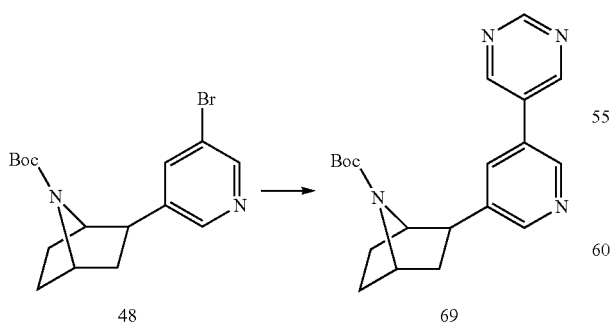

To a resealable reaction pressure vessel under nitrogen was added 48 (316 mg, 0.895 mmol, 1.0 equiv), Pd(PPh$_3$)$_4$ (52 mg, 0.045 mmol, 0.1 equiv), Na$_2$CO$_3$ (190 mg, 1.79 mmol, 2.0 equiv), pyrimidine boronic acid (144 mg, 1.16 mmol, 1.3 equiv), DME (16 mL), and water (1.5 mL). The mixture was degassed through bubbling nitrogen for 40 min and heated at 100° C. for 24 h. After cooling to room temperature the mixture was poured into 30 mL of H$_2$O and extracted with CHCl$_3$ (3×40 mL). The combined organic layers were dried over MgSO$_4$, filtered through Celite and the solvent removed in vacuo. The resultant residue was purified by flash chromatography using hexanes/EtOAc to furnish 285 mg (90%) of 69 as a colorless oil. $^1$H NMR (300 MHz, CDCl$_3$) δ 1.44 (br s, 9H), 1.58-1.69 (m, 3H), 1.87-1.94 (m, 3H), 2.05-2.12 (m, 1H), 2.99-3.04 (dd, J=9.0 Hz, 1H), 4.30 (s, 1H), 4.43 (br s, 1H), 7.91 (t, J=1.9 Hz, 1H), 8.61 (d, J=1.7 Hz, 1H), 8.70 (d, J=2.0 Hz, 1H) 8.98 (s, 2H), 9.27 (s, 1H); $^{13}$C NMR (CDCl$_3$) δ; 28.4 (3C), 29.0, 29.8, 40.6, 45.5, 56.2, 61.9, 80.1, 130.1, 131.7, 132.7, 141.9, 145.9, 149.7, 155.2, 158.2; MS (ESI) m/z 353.5 (M+H)$^+$.

Procedure for Boc Removal in the Synthesis of Analogue 62.

A solution of the Boc protected analogue 69 in CH$_2$Cl$_2$ (5 mL) and TFA (1 mL) was stirred at rt for 1 h. The solvent was removed under reduced pressure and the residual was and treated with a 20 mL aqueous solution of NH$_4$OH/ H$_2$O (3:1). The organic product was extracted with CHCl$_3$ (3×30 mL). The combined organic layers were dried over anhydrous sodium sulfate, filtered through Celite and concentrated in vacuo. Purification of the residual by flash chromatography through an ISCO column provided the analogue 62 in good yields as a colorless oil.

2-exo-[3'-(Pyrimidin-5-yl)-5'-pyridinyl]-7-azabicyclo[2.2.1]heptane (62)

$^1$H NMR (300 MHz, CDCl$_3$) δ 1.57-1.78 (m, 7H), 1.94-2.01 (dd, J=9.0, 11.2 Hz, 1H), 2.87-2.91 (dd, J=3.9, 6.9 Hz, 1H), 3.66 (s, 1H), 3.82 (br s 1H), 8.06 (t, J=2.1 Hz, 1H), 8.65 (d, J=2.0 Hz, 1H), 8.67 (d, J=2.0 Hz, 1H), 8.99 (s, 2H) 9.25 (s, 1H); $^{13}$C NMR (CDCl$_3$) δ 30.3, 31.5, 40.4, 45.1, 56.4, 62.8, 129.8, 131.7, 133.0, 142.8, 145.4, 149.7, 154.9, 157.9; MS (ESI) m/z 253.3 (M+H)$^+$.

General Procedure for the Fumarate Salt Formation (Compounds 67, 68 and 70)

A solution of the respective amine (60, 61 or 62) in chloroform (2 mL) was treated with a solution of fumaric acid (1.2 equivalents) in MeOH (0.65M). The mixture was allowed to stand in refrigerator overnight. Filtration and washing of the filter cake with ether, followed by recrystallization from MeOH-ether provided the desired fumarates as white solids.

2-exo-2'-Fluoro-3'-(pyrimidin-5-yl)deschloroepibatidine fumarate (67)

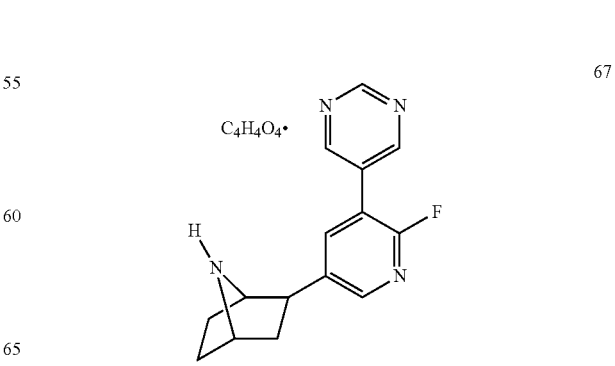

Mp. 160-163° C.; $^1$H NMR (500 MHz, METHANOL-d$_4$) δ 9.22 (s, 1H), 9.10 (s, 2H), 8.25-8.32 (m, 1H), 8.21 (dd, J=2.66, 9.20 Hz, 1H), 6.66 (s, 2H), 4.58 (d, J=3.68 Hz, 1H), 4.32-4.39 (br s, 1H), 3.53 (m, 1H), 2.48 (dd, J=2.50, 9.81 Hz, 1H), 2.14-2.24 (m, 1H), 1.99-2.14 (m, 3H), 1.85-1.96 (m, 1H); $^{13}$C NMR (500 MHz, METHANOL-d$_4$) δ 27.0, 28.95, 37.58, 43.41, 60.18, 63.83, 133.15, 136.10, 138.88, 140.18, 150.11, 158.27, 158.96, 171.15; MS (ESI) m/z 287.3 [(M-fumarate)$^+$, M=C$_{15}$H$_{15}$FN$_4$.C$_4$H$_4$O$_4$]. Anal. (C$_{19}$H$_{19}$FN$_4$O$_4$.1.25H$_2$O), C, H, N.

2-exo-2'-Chloro-3'-(pyrimidin-5-yl)deschloroepibatidine fumarate (68)

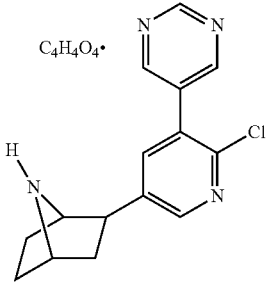

68

Mp. 199-203° C.; $^1$H NMR (300 MHz, METHANOL-d$_4$) δ 9.23 (s, 1H), 8.98 (s, 2H), 8.47 (d, J=2.13 Hz, 1H), 7.98 (d, J=2.13 Hz, 1H), 6.63 (s, 2H), 4.57 (d, J=2.2 Hz, 1H), 4.33 (br s, 1H), 3.45-3.54 (m, 1H), 2.43-2.51 (dd, J=3.7, 9.70 Hz, 1H), 1.84-2.18 (m, 5H); $^{13}$C NMR (300 MHz, METHANOL-d$_4$) δ 27.0, 28.95, 37.58, 43.41, 60.18, 63.83, 133.15, 136.10, 138.88, 140.18, 150.11, 158.27, 158.96, 171.15; MS (ESI) m/z 287.3 [(M-fumarate)$^+$, M=C$_{15}$H$_{15}$ClN$_4$.C$_4$H$_4$O$_4$]. Anal. (C$_{19}$H$_{19}$ClN$_4$O$_4$.0.25H$_2$O), C, H, N.

2-exo-3'-(Pyrimidin-5-yl)deschloroepibatidine fumarate (70)

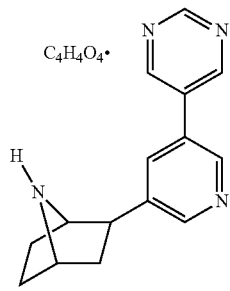

70

Mp. 172-176° C.; $^1$H NMR (500 MHz, METHANOL-d$_4$) δ 9.22 (s, 1H), 9.17-9.19 (m, 2H), 8.84 (d, J=2.04 Hz, 1H), 8.65 (d, J=2.86 Hz, 1H), 8.20-8.22 (m, 1H), 6.64 (s, 2H), 4.62 (d, J=3.68 Hz, 1H), 4.36 (br s, 1H), 3.55-3.57 (dd, J=5.72, 6.13 Hz, 1H), 2.43-2.52 (dd, J=3.7, 9.40 Hz, 1H), 2.16-2.25 (m, 1H), 1.98-2.15 (m, 3H), 1.87-1.98 (m, 1H); $^{13}$C NMR (500 MHz, METHANOL-d$_4$) δ 27.08, 29.06, 37.75, 44.03, 60.39, 63.98, 132.02, 135.03, 136.21, 139.74, 147.16, 150.01, 156.67, 159.02, 171.11; MS (ESI) m/z 253.3 [(M-fumarate)$^+$, M=C$_{15}$H$_{16}$N$_4$.C$_4$H$_4$O$_4$]. Anal. (C$_{39}$H$_{20}$N$_4$O$_4$.0.75H$_2$O), C, H, N.

Example 7

Synthesis of 2'-Fluoro-3'-(substituted thiophenyl)Epibatidine Analogues

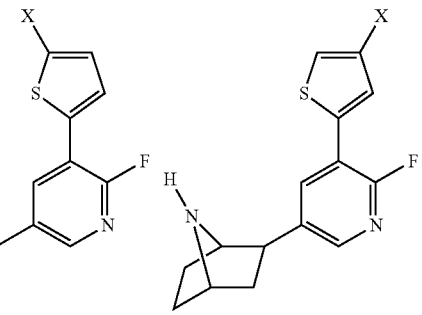

71a, X = H
71b, X = F
71c, X = Cl
71d, X = NH$_2$
71f, X = OMe

72a, X = H
72b, X = F
72c, X = Cl
72d, X = NH$_2$
72f, X = OMe

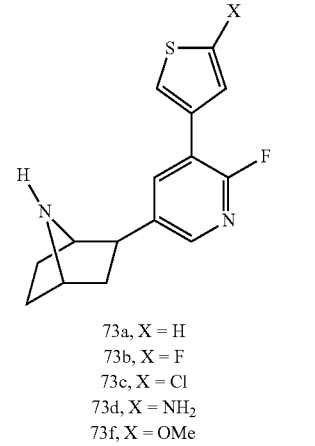

73a, X = H
73b, X = F
73c, X = Cl
73d, X = NH$_2$
73f, X = OMe

Synthesis of Analogue 71a

The synthesis of the thiophenyl substituted analogues commenced with the Heck cross coupling of 7-tert-butoxycarbonylazabicyclo[2.2.1]heptene 4 and 2-amino-5-iodopyridine, 5, in the presence of Pd(OAc)$_2$, n-Bu$_4$NCl and potassium formate, heated in DMF at 100° C. for 4 days intermediate 6, which was subsequently subjected to a bromination reaction as discussed in other examples above to provide bromo compound 7. Suzuki cross-coupling with the respective thiophenyl boronic acid in the presence of Pd(PPh$_3$)$_4$ as the catalytic system, Na$_2$CO$_3$ as the base, DMF as solvent and a catalytic amount of water, heated at 80° C. for 5 h, furnished cross-coupled product 74 as shown in Scheme 18 below. Diazotization reaction in the presence of HF-pyridine provided analogue 71a in a modest yield.

Scheme 18.

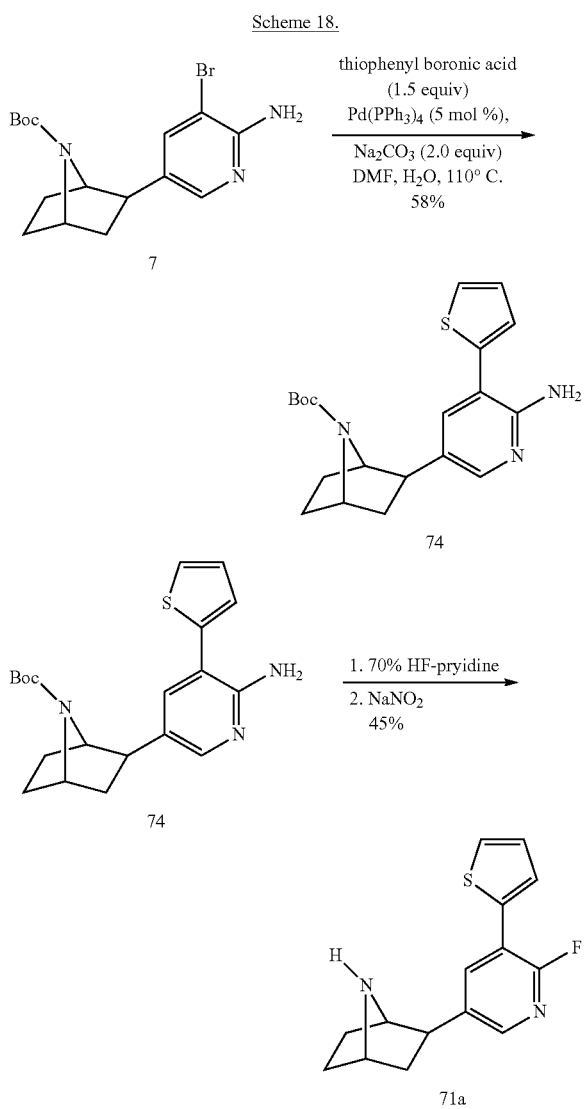

Example 8

Radioligand Binding and Pharmacology for Certain Compounds of the Present Invention

[$^3$]Epibatidine Binding Assay. The [$^3$H]Epibatidine binding assay is used to determine the affinity ($K_i$) of the test compound for heteromeric nAChRs containing alpha and beta subunits. The alpha4 beta2 subtype is the predominant nAChR present in brain tissue used in this assay. [$^{125}$I]Iodo-MLA is a radioligand that is selective for homomeric nAChRs containing the alpha7 subunit. Thus, this assay is used to determine the affinity ($K_i$) of the test compound for this nAChR and results used to calculate the selectivity of the compounds for hetero- and homomeric nAChRs.

Adult male rat cerebral cortices (Pelfreeze Biological, Rogers, Ak.) were homogenized in 39 volumes of ice-cold 50 mM Tris buffer (pH 7.4 at 4° C.) containing 120 mM NaCl, 5 mM KCl, 2 mM $CaCl_2$, and 1 mM $MgCl_2$ and sedimented at 37,000 g for 10 min at 4° C. The supernatant was discarded, the pellet resuspended in the original volume of buffer, and the wash procedure repeated twice more. After the last centrifugation, the pellet was resuspended in 1/10 its original homogenization volume and stored at −80° C. until needed. In a final volume of 0.5 mL, each assay tube contained 3 mg wet weight male rat cerebral cortex homogenate (added last), 0.5 nM [$^3$H]epibatidine (NEN Life Science Products, Wilmington, Del.) and one of 10-12 different concentrations of test compound dissolved in buffer (pH 7.4 at room temperature) containing 10% DMSO resulting in a final DMSO concentration of 1%. Total and nonspecific bindings were determined in the presence of vehicle and 300 μM (−)-nicotine, respectively. After a 4-h incubation period at room temperature, the samples were vacuum-filtered over GF/B filter papers presoaked in 0.03% polyethylenimine using a Brandel 48-well harvester and washed with 6 mL of ice-cold buffer. The amount of radioactivity trapped on the filter was determined by standard liquid scintillation techniques in a TriCarb 2200 scintillation counter (Packard Instruments, Meriden, Conn.) at approximately 50% efficiency. The binding data were fit using the nonlinear regression analysis routines in Prism (Graphpad, San Diego, Calif.). The $K_i$ values for the test compounds were calculated from their respective $IC_{50}$ values using the Cheng-Prusoff equation.

[$^{125}$I] Iodo-MLA Binding Assay. Adult male rat cerebral cortices (Pel-Freez Biologicals, Rogers, Ak.) were homogenized (polytron) in 39 volumes of ice-cold 50 mM Tris buffer (assay buffer; pH 7.4 at 4° C.) containing 120 mM NaCl, 5 mM KCl, 2 mM $CaCl_2$, and 1 mM $MgCl_2$. The homogenate was centrifuged at 35,000 g for 10 min at 4° C. and the supernatant discarded. The pellet was resuspended in the original volume of buffer and the wash procedure repeated twice more. After the last centrifugation step, the pellet was resuspended in one-tenth the original homogenization volume and stored at −80° C. until needed. Triplicate samples were run in 14-mL polypropylene tubes (Matrix Technologies Corporation, Hudson, N.H.). Briefly, in a final volume of mL, each assay sample contained 3 mg wet weight rat cerebral cortex (added last), 40-50 μM [$^{125}$I]MLA and 50 nM final concentration of test compound dissolved in buffer containing 10% DMSO, giving a final DMSO concentration of 1%. Total and nonspecific binding were determined in the presence of vehicle and 300 μM (−)-nicotine, respectively. After a 2-h incubation period on ice, the samples were vacuum-filtered using a Multimate 96-well harvester (Packard Instruments, Meriden, Conn.) onto GF/B filters presoaked for at least 30 min in assay buffer containing 0.15% bovine serum albumin. Each well was then washed with approximately 3.0 mL of ice-cold buffer. The filter plates were dried, and 30 μL of Microscint20 (Packard) was added to each well. The amount of radioligand remaining on each filter was determined using a TopCount 12-detector (Packard) microplate scintillation counter at approximately 70% efficiency.

Tail-Flick Test. Antinociception was assessed by the tail-flick method of F. E. D'Amour and D. L. Smith (*J. Pharmacol. Exp. Ther.* 1941, 72, 74-79). A control response (2-4 sec) was determined for each mouse before treatment, and a test latency was determined after drug administration. In order to minimize tissue damage, a maximum latency of 10 sec was imposed. Antinociceptive response was calculated as percent maximum possible effect (% MPE), where % MPE=[(test−control)/(10−control)]×100. Groups of eight to twelve animals were used for each dose and for each treatment. The mice were tested 5 min after s.c. injections of epibatidine analogues for the dose-response evaluation. Eight to twelve mice were treated per dose and a minimum of four doses were performed for dose-response curve determination.

Hot-Plate Test. Mice were placed into a 10 cm wide glass cylinder on a hot plate (Thermojust Apparatus) maintained at 55.0° C. Two control latencies at least 10 min apart were determined for each mouse. The normal latency (reaction time) was 8 to 12 sec. Antinociceptive response was calculated as percent maximum possible effect (% MPE), where % MPE=[(test−control)/40−control)×100]. The reaction time was scored when the animal jumped or licked its paws. Eight mice per dose were injected s.c. with epibatidine analogues and tested 5 min thereafter in order to establish a dose-response curve.

Locomotor Activity. Mice were placed into individual Omnitech photocell activity cages (28×16.5 cm) 5 min after s.c. administration of either 0.9% saline or epibatidine analogues. Interruptions of the photocell beams (two banks of eight cells each) were then recorded for the next 10 min. Data were expressed as number of photocell interruptions.

Body Temperature. Rectal temperature was measured by a thermistor probe (inserted 24 mm) and digital thermometer (Yellow Springs Instrument Co., Yellow Springs, Ohio). Readings were taken just before and 30 min at different times after the s.c. injection of either saline or epibatidine analogues. The difference in rectal temperature before and after treatment was calculated for each mouse. The ambient temperature of the laboratory varied from 21-24° C. from day to day.

Table 6 provides data for a number of compounds of the invention that were tested according to the assays described above. The nicotine acetylcholine receptor (nAChR) binding affinities and activities in nAChR animal assays of several compounds that are a part of this application were compared to varenicline (Chantix®), a drug on the market for helping smokers quit smoking Varenicline aided depressive affect in depressed smokers and also showed activity in animal models of depression. Varenicline also shows reduction of ethanol consumption and seeking in rat tests. All of the compounds like varenicline have very high affinity for nAChR as judged by inhibition of [$^3$H]epibatidine binding. The $K_i$ values ranged from 0.04 nM to 1.18 nM compared to 0.12 nM for varenicline. Like varenicline, all the compounds except one were functional antagonists in the tail-flick test. In addition, like varenicline, the compounds showed activity in one or more of the functional agonist tests and thus are partial agonists.

TABLE 6

Radioligand Binding and Pharmacology Data for 2'-Fluoro-3'-(substituted pyridine) Deschloroepibatidine Analogs

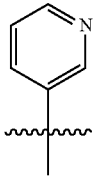

| | αβ [$^3$H] Epibatidine ($K_i$, nM) (hill slope) | α$_7$ [$^{125}$I] iodoMLA ($K_i$, nM) (hill slope) | mg/kg ED$_{50}$ Tail Flick | ED$_{50}$ Hot Plate | ED$_{50}$ Hypo-thermia | ED$_{50}$ Spontaneous Activity | AD$_{50}$ (µg/kg) Tail Flick | Hot Plate |
|---|---|---|---|---|---|---|---|---|
| Comparative compounds | | | | | | | | |
| Nicotine | 1.50 ± 0.30 | | 1.3 (0.5-1.8) | 0.65 (0.25-0.85) | 1.0 (0.6-2.1) | 0.5 (0.15-0.78) | | |
| (−)-epibatidine | 0.018 ± 0.001 | | 0.006 (0.001-0.01) | 0.004 (0.001-0.008) | 0.004 (0.002-0.008) | 0.001 (0.0005-0.005) | | |
| varenicline | 0.12 ± 0.02 | 32.5 ± 1.3 | 11% @ 10 | 10% @ 10 | 2.8 | 2.1 | 0.2 | 470 |
| Inventive compounds | | | | | | | | |
| R$_1$ = 3-pyridyl | 0.35 ± 0.038 | 5500 ± 1420 | 4.9 (3.6-6.7) | 5 (3.7-6.7) | 3.7 (2.9-4.5) | 0.69 (0.4-12.8) | 3 (0.5-24) | 10% @ 1000 |

TABLE 6-continued

Radioligand Binding and Pharmacology Data for 2'-Fluoro-3'-(substituted pyridine) Deschloroepibatidine Analogs

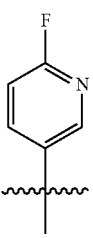

| R₁ | αβ [$^3$H] Epibatidine ($K_i$, nM) (hill slope) | α₇ [$^{125}$I] iodoMLA ($K_i$, nM) (hill slope) | mg/kg | | | | AD$_{50}$ (μg/kg) | |
|---|---|---|---|---|---|---|---|---|
| | | | ED$_{50}$ Tail Flick | ED$_{50}$ Hot Plate | ED$_{50}$ Hypo-thermia | ED$_{50}$ Spontaneous Activity | Tail Flick | Hot Plate |
| 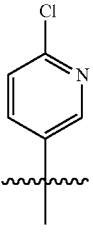 F | 0.049 ± 0.02 | 4850 ± 1800 | 3.6 (2.7-4.7) | 3.27 (2.1-5.3) | 0.68 (0.52-1.1) | 0.38 (0.13-1.1) | 1% @ 100 | 1% @ 100 |
| 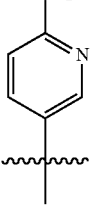 Cl | 0.063 ± 0.08 | 6600 ± 731 | 10% @ 10 | 27% @ 10 | 3.11 (1.5-5.1) | 1.58 (0.5-4.4) | 9 (2-38) | 2001 (297-3610) |
| 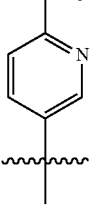 NH₂ | 0.25 ± 0.033 | 1470 ± 203 | 5% @ 10 | 8% @ 10 | 2.8 (2-3.8) | 1.84 (0.5-6.3) | 30 (3-35) | 50% @ 10 |
| 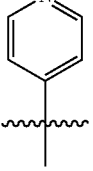 OCH₃ | 0.13 ± 0.027 | 524 ± 110 | 4.22 (3-5.3) | 1.72 (0.9-3.4) | 0.77 (0.51-1.2) | 0.53 (0.19-1.1) | 21 (3-125) | 0% @ 100 |
| N (pyridyl) | 0.12 ± 0.03 | 9700 ± 2400 | 13% @ 10 | 40% @ 10 | 1.69 (1.1-2.6) | 0.38 (0.2-2.7) | 12 (10-172) | 290 (19-991) |

TABLE 6-continued
Radioligand Binding and Pharmacology Data for 2'-Fluoro-3'-(substituted pyridine) Deschloroepibatidine Analogs
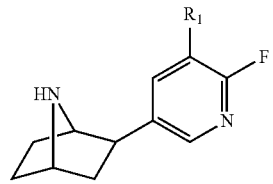
| | αβ [³H] Epibatidine (K$_i$, nM) (hill slope) | α$_7$ [¹²⁵I] iodoMLA (K$_i$, nM) (hill slope) | mg/kg | | | | AD$_{50}$ (μg/kg) | |
|---|---|---|---|---|---|---|---|---|
| | | | ED$_{50}$ Tail Flick | ED$_{50}$ Hot Plate | ED$_{50}$ Hypo- thermia | ED$_{50}$ Spontaneous Activity | Tail Flick | Hot Plate |
| 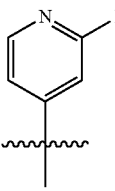 | 0.067 ± 0.01 | 7300 ± 150 | 5% @ 10 | 18% @ 10 | 1.58 (0.97-2.1) | 0.17 (0.08-1.5) | 4 (0.1-70) | 117 (110-1100) |
| 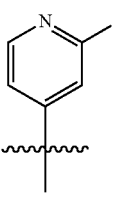 | 1.18 ± 0.14 | >10,000 | 11% @ 10 | 19% @ 10 | 2.74 (1.89-3.5) | 1.01 (0.27-3.7) | 320 (45-3262) | 1370 (180-1430) |
| 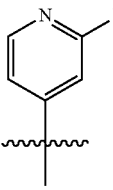 | 0.13 ± 0.005 | 719 ± 101 | 11% @ 10 | 12% @ 10 | 1.87 (0.1-3.5) | 0.61 (0.04-9.1) | 9 (0.4-19) | 10% @ 10,000 |
| 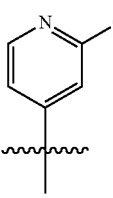 | 0.04 ± 0.012 | 7900 ± 1080 | | | | | | |

Table 7 provides some additional data for additional compounds of the invention wherein $R_1$ is pyrimidine and where the X substituent on the pyridine ring is varied. As with the compounds of Table 6, these compounds were tested according to the assays described above.

TABLE 7

Radioligand binding and antinociception profile data for 3'-(pyrimidine)epibatidine analogs

[Structure of compound shown]

| | αβ [$^3$H] Epibatidine ($K_i$, nM) (hill slope) | α$_7$ [$^{125}$I] iodoMLA ($K_i$, nM) (hill slope) | mg/kg | | | | AD$_{50}$ (μg/kg) | |
|---|---|---|---|---|---|---|---|---|
| | | | ED$_{50}$ Tail Flick | ED$_{50}$ Hot Flick | ED$_{50}$ Hypothermia | ED$_{50}$ Spontaneous Activity | Tail Flick | Hot Plate |
| Comparative compounds | | | | | | | | |
| Nicotine | 1.50 ± 0.30 | | 1.3 (0.5-1.8) | 0.65 (0.25-0.85) | 1.0 (0.6-2.1) | 0.5 (0.15-0.78) | | |
| (-)-epibatidine | 0.018 ± 0.001 | | 0.006 (0.001-0.01) | 0.004 (0.001-0.008) | 0.004 (0.002-0.008) | 0.001 (0.0005-0.005) | | |
| varenicline | 0.12 ± 0.02 | 32.5 ± 1.3 | 11% @ 10 | 10% @ 10 | 2.8 | 2.1 | 0.2 | 470 |
| Inventive compounds | | | | | | | | |
| X | | | | | | | | |
| H | 0.12 ± 0.02 | 32.5 ± 1.3 | 1.5 (1.2-2) | 1.63 (1-2.6) | 0.6 (0.16-2) | 0.32 (0.2-0.5) | 15% @ 100 | 0% @ 100 |
| F | 0.84 ± 0.08 | 1927 n = 1 | 2.15 (1.7-2.7) | 1.2 (0.8-1.7) | 0.25 (0.13-0.47) | 0.15 (0.03-0.57) | 0.24 (0.13-0.43) | 33% @ 100 |
| Cl | 0.32 ± 0.09 | 170 ± 64 n = 2* | 0.28 (0.17-0.45) | 0.25 (0.15-0.43) | 0.03 (0.02-0.035) | 0.027 (0.01-0.04) | 5% @ 100 | 2% @ 100 |

That which is claimed:

1. A compound according to the structure:

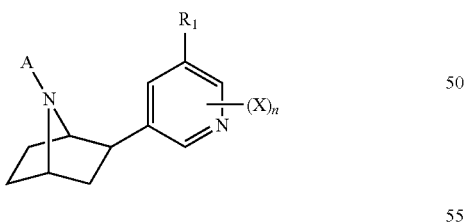

wherein:

A is —R, —N(R)$_2$, —C(=NR)N(R)$_2$, or —OR;

each R is, independently, H, alkyl, alkenyl, alkynyl, aryl, or aralkyl;

each X is, independently, H, halo, alkyl, alkenyl, alkynyl, aralkyl, —OR, —CH$_2$—CO$_2$R, —C(O)R, —CO$_2$R, —N(R)$_2$, —NR—C(O)R, —C(O)N(R)$_2$, —NR—CO$_2$R, —SO$_3$CF$_3$, —NO$_2$, —N$_3$, —CF$_3$, —CH=CHY, or —CN;

Y is halo;

n is an integer from 0-3; and $R_1$ is an optionally substituted heteroaryl selected from thiophene and pyrimidine;

or a pharmaceutically acceptable salt or stereoisomer thereof.

2. A compound of claim 1, wherein the compound has the following structure:

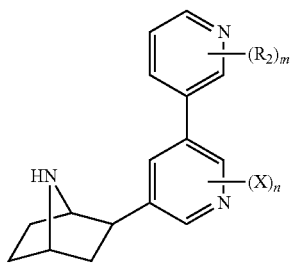

wherein:

each $R_2$ is independently selected from the group consisting of H, C1-6 alkoxy, amino, halo, hydroxyl, amide, CN, CH$_3$SO$_2$, and CF$_3$SO$_2$;

each X is independently H or halo; and p is an integer from 0-3;

or a pharmaceutically acceptable salt or stereoisomer thereof.

3. A compound of claim 1, wherein the compound has the following structure:

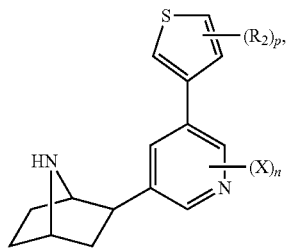

wherein:
each $R_2$ is independently selected from the group consisting of H, C1-6 alkoxy, amino, halo, hydroxyl, amide, CN, $CH_3SO_2$, and $CF_3SO_2$;
each X is independently H or halo; and
p is an integer from 0-3;
or a pharmaceutically acceptable salt or stereoisomer thereof.

4. A compound according to claim 1 selected from the group consisting of:
2-exo- [2'-Fluoro-3'-(pyrimidin-3-yl)-5'-pyridinyl]-7-azabicyclo [2.2.1]heptane;
2-exo-[2'-Chloro-3'-(pyrimidin-5-yl)-5'-pyridnyl]-7-azabicyclo [2.2.1]heptane;
2-exo[3'-(Pyrimidin-5-yl)-5'-pyridnyl]-7-azabicyclo [2.2.1]heptane;
2-exo-[2'-Fluoro-3'-(thiophen-2-yl)-5'-pyridinyl]-7-azabicyclo [2.2.1]heptane;
2-exo- [2'-Fluoro-3'-(5-fluorothiophen-2-yl)-5'-pyridinyl]-7-azabicyclo [2.2.1]heptane;
2-exo- [2'-Fluoro-3-chlorothiophen-2-yl)-5'-pyridinyl]-7-azabicyclo [2.2.1]heptane;
2-exo-[2'-Fluoro-3'-(5-aminothiophen-2-yl)-5'-pyridinyl]-7-azabicyclo [2.2.1]heptane;
2-exo-[2'-Fluoro-3'-(5-methoxythiophen-2-yl)-5'-pyridinyl]-7-azabicyclo [2.2.1]heptane;
2-exo- [2'-Fluoro-3'-(4-fluorothiophen-2-yl)-5'-pyridinyl]-7-azabicyclo [22.1]heptane;
2-exo- [2'-Fluoro-3'-(4-chlorothiophen-2-yl)-5'-pyridinyl]-7-azabicyclo [2.2.1]heptane;
2-exo- [2'-Fluoro-3'-(4-aminothiophen-2-yl)-5'-pyridinyl]-7-azabicyclo [2.2.1]heptane;
2-exo- [2'-Fluoro-3'-(4-methoxythiophen-2-yl)-5'-pyridinyl]-7-azabicyclo [2.2.1]heptane;
2-exo-[2'-Fluoro-3'-(thiophen-3-yl)-5'-pyridinyl]-7-azabicyclo [2.2.1]heptane;
2-exo-[2'-Fluoro-3'-(5-fluorothiophen- 3-yl)-5'-pyridinyl]-7-azabicyclo [2.2.1]heptane;
2-exo-[2'-Fluoro-3'-(5-chlorothiophen-3-yl)-5'-pyridinyl]-7-azabicyclo [2.2.1]heptane;
2-exo-[2'-Fluoro-3'-(5-aminothiophen- 3-yl)-5 '-pyridinyl]-7-azabicyclo [2.2.1]heptane; and
2-exo-[2'-Fluoro-3-methoxythiophen-3-yl)-5'-pyridinyl]-7-azabicyclo [2.2.1]heptane.

5. A pharmaceutical composition comprising a compound of claim 1 and one or more phaimaceutically acceptable carriers.

6. The compound of claim 1, wherein $R_1$ is optionally substituted pyrimidine.

7. The compound of claim 6, wherein X is halo, n=1, and A is H.

8. The compound of claim 1, wherein the optionally substituted heteroaryl has one or more substituents selected from the group consisting of amino, amido, alkyl, halo, $R_{12}R_{13}NSO_2$, and alkoxy substituents, wherein $R_{12}$ and $R_{13}$ are each independently selected from H and C1-10 alkyl.

9. The compound of claim 1, wherein the optionally substituted heteroaryl is substituted with one or more substituents independently selected from the group consisting of C1-6 alkoxy, amino, halo, hydroxyl, amide, CN, $CH_3SO_2$, and $CF_3SO_2$.

10. The compound of claim 6, wherein the optionally substituted pyrimidine is substituted with one or more substituents independently selected from the group consisting of C1-6 alkoxy, amino, halo, hydroxyl, amide, CN, $CH_3SO_2$, and $CF_3SO_2$.

* * * * *

UNITED STATES PATENT AND TRADEMARK OFFICE
CERTIFICATE OF CORRECTION

PATENT NO.        : 8,981,102 B2
APPLICATION NO.   : 13/817697
DATED             : March 17, 2015
INVENTOR(S)       : Frank Ivy Carroll and Pauline Wanjiku Ondachi It is certified that error appears in the above-identified patent and that said Letters Patent is hereby corrected as shown below:

Claims

In the chemical structure recited in Claim 2, which appears at Column 92, Lines 46-58, there is an error: the recited structure should be:

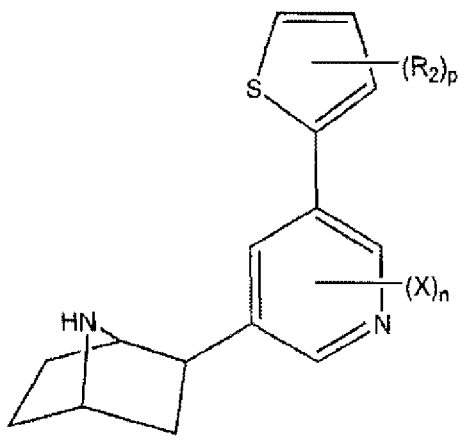

as shown in the listing of claims in the amendment filed October 20, 2014. Please replace the recited chemical structure, which appears at Column 92, Lines 46-58 with the above-referenced structure.

Please correct the portion of the text of Claim 4, which appears in Column 94, Lines 1-2 to read as follows:

2-*exo*-[2'-Fluoro-3'-(4-fluorothiophen-2-yl)-5'-pyridinyl]-7-azabicyclo[2.2.1]heptane;

Signed and Sealed this
Tenth Day of November, 2015

Michelle K. Lee
*Director of the United States Patent and Trademark Office*